United States Patent
Yarnell et al.

(10) Patent No.: US 11,714,090 B2
(45) Date of Patent: Aug. 1, 2023

(54) NON-ANTIBODY LIGANDS FOR DETECTING TARGET PROTEINS

(71) Applicant: Syngenta Participations AG, Basel (CH)

(72) Inventors: Michele Yarnell, Research Triangle Park, NC (US); Anne Chevrel, Nantes (FR); Olivier Kitten, Nantes (FR); Scott Young, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 367 days.

(21) Appl. No.: 16/771,302

(22) PCT Filed: Dec. 13, 2018

(86) PCT No.: PCT/US2018/065440
§ 371 (c)(1),
(2) Date: Jun. 10, 2020

(87) PCT Pub. No.: WO2019/118721
PCT Pub. Date: Jun. 20, 2019

(65) Prior Publication Data
US 2021/0181204 A1  Jun. 17, 2021

Related U.S. Application Data

(60) Provisional application No. 62/599,289, filed on Dec. 15, 2017.

(51) Int. Cl.
*C07K 14/00* (2006.01)
*G01N 33/569* (2006.01)
*G01N 33/68* (2006.01)

(52) U.S. Cl.
CPC .............. *G01N 33/68* (2013.01); *C07K 14/00* (2013.01); *G01N 33/56961* (2013.01); *G01N 2333/415* (2013.01)

(58) Field of Classification Search
CPC .............. G01N 33/68; G01N 33/56961; G01N 2333/415; C07K 14/00
See application file for complete search history.

(56) References Cited

U.S. PATENT DOCUMENTS

| 7,927,598 B2 | 4/2011 | Malvar et al. |
| 8,309,516 B2 * | 11/2012 | Hart .................. C12N 15/8286 514/4.5 |
| 9,090,892 B2 | 7/2015 | Jones |
| 9,422,548 B2 | 8/2016 | Pecorari et al. |

FOREIGN PATENT DOCUMENTS

WO    2017161096 A1    9/2017

OTHER PUBLICATIONS

Walters et al. "Lepidopteran-Active Variable-Region Sequence Imparts Coleopteran Activity in eCry3.1Ab, an Engineered Bacillus thuringiensis Hybrid Insecticidal Protein" 2010 Applied & Enviro. Micro. 76(10):3082-3088). (Year: 2010).*
Behar et al. "Tolerance of the archaeal Sac7d scaffold protein to alternative library designs: characterization of anti-immunoglobulin G Affitins" 2013 Protein Engineering Design & Selection 26(4): 267-275 (Year: 2013).*
Crespo et al."Comparison and Validation of MEthods to Quantify Cry1AB Toxin from Bacillus Thuringiensis for Standardization of Insect Bioassays," Applied and Environmental Microbiology, Nov. 2, 2007, vol. 74, No. 1, pp. 130-135.
Jin et al., "A Novel Impedimetric Microfludic Analysis System for Transgenic Protein Cry1Ab Detection," Scientific Reports, Mar. 2, 2017, vol. 7, No. 43175, pp. 1-8.
Wang et al., "Isolation of a peptide from Ph.D.-C7C phage display library for detection of Cry1Ab," Analytical Biochemistry, Mar. 6, 2017, vol. 539, pp. 29-32.
Ferrigno P.K., "Non-antibody protein-based biosensors," Essays in Biochemistry, Jun. 30, 2016, vol. 60, pp. 19-25.
Qui et al., "Proteomic analysis of Cry2Aa-binding proteins and their receptro function in Spodoptera exigua", Scientific Reports. Jan. 9, 2017, vol. 7, No. 40222, pp. 1-10.
International Search Report cited in Application No. PCT/US2018/065440 dated Dec. 13, 2018.
Malik et al., "Protein-Based Detection Methods for Genetically Modified Crops", obtained from website http://dx.doi.org/10.5772/Intechopen.75520, pp. 47-65.
Extended ESR for PCT/US2018065440, dated Aug. 9, 2021.
Mouratou, B. et al.: "Remodeling a DNA-binding protein as a specific in vivo inhibitor of bacterial secretin PuID", Proceedings of the National Academy of Sciences, vol. 104, No. 46, Nov. 1, 2007, pp. 17983-17988, XP055000032, US, ISSN: 0027-8424, DOI: 10.1073/pnas.0702963104.
Dias, Ana M.G.C. et al.: "The future of protein scaffolds as affinity reagents for purification: The Future of Protein Scaffolds", Biotechnology and Bioengineering, vol. 114, No. 3, Mar. 1, 2017, pp. 481-491, XP055530301, US, ISSN: 0006-3592, DOI: 10.1002/bit.26090.

(Continued)

*Primary Examiner* — Matthew R Keogh
*Assistant Examiner* — Rebecca Stephens
(74) *Attorney, Agent, or Firm* — Katherine Seguin

(57) ABSTRACT

The invention relates generally to synthetic non-antibody protein scaffolds (synNAPS) that differentially detect or quantitate a target insecticidal protein in a complex biological matrix comprising the target protein and a non-target insecticidal protein and to methods of using the synNAPS in immunoassays, and more particularly to monoclonal antibodies and immunoassays for the differential detection and quantitation of a wild-type crystal protein, such as a wild-type-Cry1Ab, from *Bacillus thuringiensis* and hybrid crystal proteins, which comprise all or a significant portion of the wild-type Cry protein in complex biological samples comprising both the wild-type Cry protein and one or more of the hybrid Cry proteins.

5 Claims, No Drawings

Specification includes a Sequence Listing.

(56) References Cited

OTHER PUBLICATIONS

Miranda, Frederico F. et al.: "Reagentless fluorescent biosensors from artificial families of antigen binding proteins", Biosensors and Bioelectronics, Apr. 1, 2011, XP055000030, ISSN: 0956-5663, DOI: 10.1016/j.bios.2011.04.030.

\* cited by examiner

SEQUENCE LISTING

<160> NUMBER OF SEQ ID NOS: 98

<210> SEQ ID NO 1
<211> LENGTH: 615
<212> TYPE: PRT
<213> ORGANISM: Bacillus thuringiensis

<400> SEQUENCE: 1

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Gly Ser Ile Arg Ser Pro His Leu Met Asp Ile Leu Asn Ser Ile Thr
            290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
```

```
            420                 425                 430
Val Ser Met Phe Arg Ser Gly Phe Ser Asn Ser Val Ser Ile Ile
        435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
        530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
                580                 585                 590

Ser Gly Asn Glu Val Tyr Ile Asp Arg Ile Glu Phe Val Pro Ala Glu
            595                 600                 605

Val Thr Phe Glu Ala Glu Tyr
        610                 615

<210> SEQ ID NO 2
<211> LENGTH: 653
<212> TYPE: PRT
<213> ORGANISM: Artificial Sequence
<220> FEATURE:
<223> OTHER INFORMATION: Hybrid toxin.

<400> SEQUENCE: 2

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160

Leu Thr Thr Tyr Ala Gln Ala Ala Asn Thr His Leu Phe Leu Leu Lys
```

```
              165                 170                 175
Asp Ala Gln Ile Tyr Gly Glu Glu Trp Gly Tyr Glu Lys Glu Asp Ile
            180                 185                 190
Ala Glu Phe Tyr Lys Arg Gln Leu Lys Leu Thr Gln Glu Tyr Thr Asp
            195                 200                 205
His Cys Val Lys Trp Tyr Asn Val Gly Leu Asp Lys Leu Arg Gly Ser
            210                 215                 220
Ser Tyr Glu Ser Trp Val Asn Phe Asn Arg Tyr Arg Glu Met Thr
225                 230                 235                 240
Leu Thr Val Leu Asp Leu Ile Ala Leu Phe Pro Leu Tyr Asp Val Arg
                245                 250                 255
Leu Tyr Pro Lys Glu Val Lys Thr Glu Leu Thr Arg Asp Val Leu Thr
                260                 265                 270
Asp Pro Ile Val Gly Val Asn Asn Leu Arg Gly Tyr Gly Thr Thr Phe
                275                 280                 285
Ser Asn Ile Glu Asn Tyr Ile Arg Lys Pro His Leu Phe Asp Tyr Leu
            290                 295                 300
His Arg Ile Gln Phe His Thr Arg Phe Gln Pro Gly Tyr Tyr Gly Asn
305                 310                 315                 320
Asp Ser Phe Asn Tyr Trp Ser Gly Asn Tyr Val Ser Thr Arg Pro Ser
                325                 330                 335
Ile Gly Ser Asn Asp Ile Ile Thr Ser Pro Phe Tyr Gly Asn Lys Ser
                340                 345                 350
Ser Glu Pro Val Gln Asn Leu Glu Phe Asn Gly Glu Lys Val Tyr Arg
            355                 360                 365
Ala Val Ala Asn Thr Asn Leu Ala Val Trp Pro Ser Ala Val Tyr Ser
            370                 375                 380
Gly Val Thr Lys Val Glu Phe Ser Gln Tyr Asn Asp Gln Thr Asp Glu
385                 390                 395                 400
Ala Ser Thr Gln Thr Tyr Asp Ser Lys Arg Asn Val Gly Ala Val Ser
                405                 410                 415
Trp Asp Ser Ile Asp Gln Leu Pro Pro Glu Thr Thr Asp Glu Pro Leu
                420                 425                 430
Glu Lys Gly Tyr Ser His Gln Leu Asn Tyr Val Met Cys Phe Leu Met
            435                 440                 445
Gln Gly Ser Arg Gly Thr Ile Pro Val Leu Thr Trp Thr His Lys Ser
            450                 455                 460
Val Asp Phe Phe Asn Met Ile Asp Ser Lys Lys Ile Thr Gln Leu Pro
465                 470                 475                 480
Leu Thr Lys Ser Thr Asn Leu Gly Ser Gly Thr Ser Val Val Lys Gly
                485                 490                 495
Pro Gly Phe Thr Gly Gly Asp Ile Leu Arg Arg Thr Ser Pro Gly Gln
                500                 505                 510
Ile Ser Thr Leu Arg Val Asn Ile Thr Ala Pro Leu Ser Gln Arg Tyr
            515                 520                 525
Arg Val Arg Ile Arg Tyr Ala Ser Thr Thr Asn Leu Gln Phe His Thr
            530                 535                 540
Ser Ile Asp Gly Arg Pro Ile Asn Gln Gly Asn Phe Ser Ala Thr Met
545                 550                 555                 560
Ser Ser Gly Ser Asn Leu Gln Ser Gly Ser Phe Arg Thr Val Gly Phe
                565                 570                 575
Thr Thr Pro Phe Asn Phe Ser Asn Gly Ser Ser Val Phe Thr Leu Ser
                580                 585                 590
```

```
Ala His Val Phe Asn Ser Gly Asn Glu Val Tyr Ile Asp Arg Ile Glu
        595                 600                 605

Phe Val Pro Ala Glu Val Thr Phe Glu Ala Glu Tyr Asp Leu Glu Arg
610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
                645                 650

<210> SEQ ID NO 3
<211> LENGTH: 598
<212> TYPE: PRT
<213> ORGANISM: Artificial Sequnece
<220> FEATURE:
<223> OTHER INFORMATION: modified Cry3A

<400> SEQUENCE: 3

Met Thr Ala Asp Asn Asn Thr Glu Ala Leu Asp Ser Ser Thr Thr Lys
1               5                   10                  15

Asp Val Ile Gln Lys Gly Ile Ser Val Val Gly Asp Leu Leu Gly Val
                20                  25                  30

Val Gly Phe Pro Phe Gly Gly Ala Leu Val Ser Phe Tyr Thr Asn Phe
            35                  40                  45

Leu Asn Thr Ile Trp Pro Ser Glu Asp Pro Trp Lys Ala Phe Met Glu
50                  55                  60

Gln Val Glu Ala Leu Met Asp Gln Lys Ile Ala Asp Tyr Ala Lys Asn
65                  70                  75                  80

Lys Ala Leu Ala Glu Leu Gln Gly Leu Gln Asn Asn Val Glu Asp Tyr
                85                  90                  95

Val Ser Ala Leu Ser Ser Trp Gln Lys Asn Pro Ala Ala Pro Phe Arg
            100                 105                 110

Asn Pro His Ser Gln Gly Arg Ile Arg Glu Leu Phe Ser Gln Ala Glu
        115                 120                 125

Ser His Phe Arg Asn Ser Met Pro Ser Phe Ala Ile Ser Gly Tyr Glu
    130                 135                 140

Val Leu Phe Leu Thr Thr Tyr Ala Gln Ala Ala Asn Thr His Leu Phe
145                 150                 155                 160

Leu Leu Lys Asp Ala Gln Ile Tyr Gly Glu Glu Trp Gly Tyr Glu Lys
                165                 170                 175

Glu Asp Ile Ala Glu Phe Tyr Lys Arg Gln Leu Lys Leu Thr Gln Glu
            180                 185                 190

Tyr Thr Asp His Cys Val Lys Trp Tyr Asn Val Gly Leu Asp Lys Leu
        195                 200                 205

Arg Gly Ser Ser Tyr Glu Ser Trp Val Asn Phe Asn Arg Tyr Arg Arg
    210                 215                 220

Glu Met Thr Leu Thr Val Leu Asp Leu Ile Ala Leu Phe Pro Leu Tyr
225                 230                 235                 240

Asp Val Arg Leu Tyr Pro Lys Glu Val Lys Thr Glu Leu Thr Arg Asp
                245                 250                 255

Val Leu Thr Asp Pro Ile Val Gly Val Asn Asn Leu Arg Gly Tyr Gly
            260                 265                 270

Thr Thr Phe Ser Asn Ile Glu Asn Tyr Ile Arg Lys Pro His Leu Phe
        275                 280                 285

Asp Tyr Leu His Arg Ile Gln Phe His Thr Arg Phe Gln Pro Gly Tyr
    290                 295                 300
```

Tyr Gly Asn Asp Ser Phe Asn Tyr Trp Ser Gly Asn Tyr Val Ser Thr
305                 310                 315                 320

Arg Pro Ser Ile Gly Ser Asn Asp Ile Ile Thr Ser Pro Phe Tyr Gly
            325                 330                 335

Asn Lys Ser Ser Glu Pro Val Gln Asn Leu Glu Phe Asn Gly Glu Lys
        340                 345                 350

Val Tyr Arg Ala Val Ala Asn Thr Asn Leu Ala Val Trp Pro Ser Ala
    355                 360                 365

Val Tyr Ser Gly Val Thr Lys Val Glu Phe Ser Gln Tyr Asn Asp Gln
370                 375                 380

Thr Asp Glu Ala Ser Thr Gln Thr Tyr Asp Ser Lys Arg Asn Val Gly
385                 390                 395                 400

Ala Val Ser Trp Asp Ser Ile Asp Gln Leu Pro Pro Glu Thr Thr Asp
                405                 410                 415

Glu Pro Leu Glu Lys Gly Tyr Ser His Gln Leu Asn Tyr Val Met Cys
            420                 425                 430

Phe Leu Met Gln Gly Ser Arg Gly Thr Ile Pro Val Leu Thr Trp Thr
        435                 440                 445

His Lys Ser Val Asp Phe Phe Asn Met Ile Asp Ser Lys Lys Ile Thr
    450                 455                 460

Gln Leu Pro Leu Val Lys Ala Tyr Lys Leu Gln Ser Gly Ala Ser Val
465                 470                 475                 480

Val Ala Gly Pro Arg Phe Thr Gly Gly Asp Ile Ile Gln Cys Thr Glu
                485                 490                 495

Asn Gly Ser Ala Ala Thr Ile Tyr Val Thr Pro Asp Val Ser Tyr Ser
            500                 505                 510

Gln Lys Tyr Arg Ala Arg Ile His Tyr Ala Ser Thr Ser Gln Ile Thr
        515                 520                 525

Phe Thr Leu Ser Leu Asp Gly Ala Pro Phe Asn Gln Tyr Tyr Phe Asp
    530                 535                 540

Lys Thr Ile Asn Lys Gly Asp Thr Leu Thr Tyr Asn Ser Phe Asn Leu
545                 550                 555                 560

Ala Ser Phe Ser Thr Pro Phe Glu Leu Ser Gly Asn Asn Leu Gln Ile
                565                 570                 575

Gly Val Thr Gly Leu Ser Ala Gly Asp Lys Val Tyr Ile Asp Lys Ile
            580                 585                 590

Glu Phe Ile Pro Val Asn
        595

<210> SEQ ID NO 4
<211> LENGTH: 1176
<212> TYPE: PRT
<213> ORGANISM: Bacillus thuringiensis

<400> SEQUENCE: 4

Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val

-continued

```
            65                  70                  75                  80
Glu Gln Leu Ile Asn Gln Arg Ile Ala Glu Ala Val Arg Asn Thr Ala
                    85                  90                  95
Ile Gln Glu Leu Glu Gly Met Ala Arg Val Tyr Arg Thr Tyr Ala Thr
                100                 105                 110
Ala Phe Ala Glu Trp Glu Lys Ala Pro Asp Pro Glu Leu Arg Glu
                115                 120                 125
Ala Leu Arg Thr Gln Phe Thr Ala Thr Glu Thr Tyr Ile Ser Gly Arg
            130                 135                 140
Ile Ser Val Leu Lys Ile Gln Thr Phe Glu Val Gln Leu Leu Ser Val
145                 150                 155                 160
Phe Ala Gln Ala Ala Asn Leu His Leu Ser Leu Leu Arg Asp Val Val
                165                 170                 175
Phe Phe Gly Gln Arg Trp Gly Phe Ser Thr Thr Thr Val Asn Asn Tyr
                180                 185                 190
Tyr Asn Asp Leu Thr Glu Gly Ile Ser Thr Tyr Thr Asp Tyr Ala Val
                195                 200                 205
Arg Trp Tyr Asn Thr Gly Leu Glu Arg Val Trp Gly Pro Asp Ser Arg
            210                 215                 220
Asp Trp Val Arg Tyr Asn Gln Phe Arg Arg Glu Leu Thr Leu Thr Val
225                 230                 235                 240
Leu Asp Ile Val Ala Leu Phe Ser Asn Tyr Asp Ser Arg Arg Tyr Pro
                245                 250                 255
Ile Arg Thr Val Ser Gln Leu Thr Arg Glu Ile Tyr Thr Asn Pro Val
                260                 265                 270
Leu Glu Asn Phe Asp Gly Ser Phe Arg Gly Met Ala Gln Arg Ile Glu
            275                 280                 285
Gln Asn Ile Arg Gln Pro His Leu Met Asp Ile Leu Asn Ser Ile Thr
            290                 295                 300
Ile Tyr Thr Asp Val His Arg Gly Phe Asn Tyr Trp Ser Gly His Gln
305                 310                 315                 320
Ile Thr Ala Ser Pro Val Gly Phe Ser Gly Pro Glu Phe Ala Phe Pro
                325                 330                 335
Leu Phe Gly Asn Ala Gly Asn Ala Ala Pro Pro Val Leu Val Ser Leu
                340                 345                 350
Thr Gly Leu Gly Ile Phe Arg Thr Leu Ser Ser Pro Leu Tyr Arg Arg
            355                 360                 365
Ile Ile Leu Gly Ser Gly Pro Asn Asn Gln Glu Leu Phe Val Leu Asp
            370                 375                 380
Gly Thr Glu Phe Ser Phe Ala Ser Leu Thr Thr Asn Leu Pro Ser Thr
385                 390                 395                 400
Ile Tyr Arg Gln Arg Gly Thr Val Asp Ser Leu Asp Val Ile Pro Pro
                405                 410                 415
Gln Asp Asn Ser Val Pro Pro Arg Ala Gly Phe Ser His Arg Leu Ser
            420                 425                 430
His Val Thr Met Leu Ser Gln Ala Ala Gly Ala Val Tyr Thr Leu Arg
            435                 440                 445
Ala Pro Thr Phe Ser Trp Gln His Arg Ser Ala Glu Phe Asn Asn Ile
            450                 455                 460
Ile Pro Ser Ser Gln Ile Thr Gln Ile Pro Leu Thr Lys Ser Thr Asn
465                 470                 475                 480
Leu Gly Ser Gly Thr Ser Val Val Lys Gly Pro Gly Phe Thr Gly Gly
                485                 490                 495
```

-continued

Asp Ile Leu Arg Arg Thr Ser Pro Gly Gln Ile Ser Thr Leu Arg Val
            500                 505                 510

Asn Ile Thr Ala Pro Leu Ser Gln Arg Tyr Arg Val Arg Ile Arg Tyr
            515                 520                 525

Ala Ser Thr Thr Asn Leu Gln Phe His Thr Ser Ile Asp Gly Arg Pro
530                 535                 540

Ile Asn Gln Gly Asn Phe Ser Ala Thr Met Ser Ser Gly Ser Asn Leu
545                 550                 555                 560

Gln Ser Gly Ser Phe Arg Thr Val Gly Phe Thr Thr Pro Phe Asn Phe
                565                 570                 575

Ser Asn Gly Ser Ser Val Phe Thr Leu Ser Ala His Val Phe Asn Ser
            580                 585                 590

Gly Asn Glu Val Tyr Ile Asp Arg Ile Glu Phe Val Pro Ala Glu Val
            595                 600                 605

Thr Phe Glu Ala Glu Tyr Asp Leu Glu Arg Ala Gln Lys Ala Val Asn
            610                 615                 620

Glu Leu Phe Thr Ser Ser Asn Gln Ile Gly Leu Lys Thr Asp Val Thr
625                 630                 635                 640

Asp Tyr His Ile Asp Gln Val Ser Asn Leu Val Glu Cys Leu Ser Asp
                645                 650                 655

Glu Phe Cys Leu Asp Glu Lys Gln Glu Leu Ser Glu Lys Val Lys His
            660                 665                 670

Ala Lys Arg Leu Ser Asp Glu Arg Asn Leu Leu Gln Asp Pro Asn Phe
        675                 680                 685

Arg Gly Ile Asn Arg Gln Leu Asp Arg Gly Trp Arg Gly Ser Thr Asp
690                 695                 700

Ile Thr Ile Gln Gly Gly Asp Asp Val Phe Lys Glu Asn Tyr Val Thr
705                 710                 715                 720

Leu Leu Gly Thr Phe Asp Glu Cys Tyr Pro Thr Tyr Leu Tyr Gln Lys
                725                 730                 735

Ile Asp Glu Ser Lys Leu Lys Ala Tyr Thr Arg Tyr Gln Leu Arg Gly
            740                 745                 750

Tyr Ile Glu Asp Ser Gln Asp Leu Glu Ile Tyr Leu Ile Arg Tyr Asn
            755                 760                 765

Ala Lys His Glu Thr Val Asn Val Pro Gly Thr Gly Ser Leu Trp Pro
770                 775                 780

Leu Ser Ala Gln Ser Pro Ile Gly Lys Cys Gly Glu Pro Asn Arg Cys
785                 790                 795                 800

Ala Pro His Leu Glu Trp Asn Pro Asp Leu Asp Cys Ser Cys Arg Asp
                805                 810                 815

Gly Glu Lys Cys Ala His His Ser His His Phe Ser Leu Asp Ile Asp
            820                 825                 830

Val Gly Cys Thr Asp Leu Asn Glu Asp Leu Gly Val Trp Val Ile Phe
            835                 840                 845

Lys Ile Lys Thr Gln Asp Gly His Ala Arg Leu Gly Asn Leu Glu Phe
        850                 855                 860

Leu Glu Glu Lys Pro Leu Val Gly Glu Ala Leu Ala Arg Val Lys Ile
865                 870                 875                 880

Ala Glu Lys Lys Trp Arg Asp Lys Arg Glu Lys Leu Glu Trp Glu Thr
                885                 890                 895

Asn Ile Val Tyr Lys Glu Ala Lys Glu Ser Val Asp Ala Leu Phe Val
            900                 905                 910

```
Asn Ser Gln Tyr Asp Gln Leu Gln Ala Asp Thr Asn Ile Ala Met Ile
        915                 920                 925

His Ala Ala Asp Lys Arg Val His Ser Ile Arg Glu Ala Tyr Leu Pro
    930                 935                 940

Glu Leu Ser Val Ile Pro Gly Val Asn Ala Ala Ile Phe Glu Glu Leu
945                 950                 955                 960

Glu Gly Arg Ile Phe Thr Ala Phe Ser Leu Tyr Asp Ala Arg Asn Val
                965                 970                 975

Ile Lys Asn Gly Asp Phe Asn Asn Gly Leu Ser Cys Trp Asn Val Lys
            980                 985                 990

Gly His Val Asp Val Glu Glu Gln  Asn Asn Gln Arg Ser  Val Leu Val
        995                 1000                1005

Val Pro  Glu Trp Glu Ala Glu  Val Ser Gln Glu Val  Arg Val Cys
    1010                1015                1020

Pro Gly  Arg Gly Tyr Ile Leu  Arg Val Thr Ala Tyr  Lys Glu Gly
    1025                1030                1035

Tyr Gly  Glu Gly Cys Val Thr  Ile His Glu Ile Glu  Asn Asn Thr
    1040                1045                1050

Asp Glu  Leu Lys Phe Ser Asn  Cys Val Glu Glu Glu  Ile Tyr Ser
    1055                1060                1065

Asn Asn  Thr Val Thr Cys Asn  Asp Tyr Thr Val Asn  Gln Glu Glu
    1070                1075                1080

Tyr Gly  Gly Ala Tyr Thr Ser  Arg Asn Arg Gly Tyr  Asn Glu Ala
    1085                1090                1095

Pro Ser  Val Pro Ala Asp Tyr  Ala Ser Val Tyr Glu  Glu Lys Ser
    1100                1105                1110

Tyr Thr  Asp Gly Arg Arg Glu  Asn Pro Cys Glu Phe  Asn Arg Gly
    1115                1120                1125

Tyr Arg  Asp Tyr Thr Pro Leu  Pro Val Gly Tyr Val  Thr Lys Glu
    1130                1135                1140

Leu Glu  Tyr Phe Pro Glu Thr  Asp Lys Val Trp Ile  Glu Ile Gly
    1145                1150                1155

Glu Thr  Glu Gly Thr Phe Ile  Val Asp Ser Val Glu  Leu Leu Leu
    1160                1165                1170

Met Glu  Glu
    1175

<210> SEQ ID NO 5
<211> LENGTH: 1181
<212> TYPE: PRT
<213> ORGANISM: Bacillus thuringiensis
<400> SEQUENCE: 5

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95
```

```
Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Ser Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Met Ala Gln Arg Ile Glu
            275                 280                 285

Gln Asn Ile Arg Gln Pro His Leu Met Asp Ile Leu Asn Ser Ile Thr
290                 295                 300

Ile Tyr Thr Asp Val His Arg Gly Phe Asn Tyr Trp Ser Gly His Gln
305                 310                 315                 320

Ile Thr Ala Ser Pro Val Gly Phe Ser Gly Pro Glu Phe Ala Phe Pro
                325                 330                 335

Leu Phe Gly Asn Ala Gly Asn Ala Ala Pro Pro Val Leu Val Ser Leu
            340                 345                 350

Thr Gly Leu Gly Ile Phe Arg Thr Leu Ser Ser Pro Leu Tyr Arg Arg
            355                 360                 365

Ile Ile Leu Gly Ser Gly Pro Asn Asn Gln Glu Leu Phe Val Leu Asp
370                 375                 380

Gly Thr Glu Phe Ser Phe Ala Ser Leu Thr Thr Asn Leu Pro Ser Thr
385                 390                 395                 400

Ile Tyr Arg Gln Arg Gly Thr Val Asp Ser Leu Asp Val Ile Pro Pro
                405                 410                 415

Gln Asp Asn Ser Val Pro Pro Arg Ala Gly Phe Ser His Arg Leu Ser
            420                 425                 430

His Val Thr Met Leu Ser Gln Ala Ala Gly Ala Val Tyr Thr Leu Arg
            435                 440                 445

Ala Pro Thr Phe Ser Trp Gln His Arg Ser Ala Glu Phe Asn Asn Ile
450                 455                 460

Ile Ala Ser Asp Ser Ile Thr Gln Ile Pro Ala Val Lys Gly Asn Phe
465                 470                 475                 480

Leu Phe Asn Gly Ser Val Ile Ser Gly Pro Gly Phe Thr Gly Gly Asp
                485                 490                 495

Leu Val Arg Leu Asn Ser Ser Gly Asn Asn Ile Gln Asn Arg Gly Tyr
            500                 505                 510
```

```
Ile Glu Val Pro Ile His Phe Pro Ser Thr Ser Thr Arg Tyr Arg Val
            515                 520                 525

Arg Val Arg Tyr Ala Ser Val Thr Pro Ile His Leu Asn Val Asn Trp
    530                 535                 540

Gly Asn Ser Ser Ile Phe Ser Asn Thr Val Pro Ala Thr Ala Thr Ser
545                 550                 555                 560

Leu Asp Asn Leu Gln Ser Ser Asp Phe Gly Tyr Phe Glu Ser Ala Asn
                565                 570                 575

Ala Phe Thr Ser Ser Leu Gly Asn Ile Val Gly Val Arg Asn Phe Ser
            580                 585                 590

Gly Thr Ala Gly Val Ile Ile Asp Arg Phe Glu Phe Ile Pro Val Thr
        595                 600                 605

Ala Thr Leu Glu Ala Glu Tyr Asn Leu Glu Arg Ala Gln Lys Ala Val
    610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Cys Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
        675                 680                 685

Phe Lys Asp Ile Asn Arg Gln Pro Glu Arg Gly Trp Gly Gly Ser Thr
    690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Val Tyr Leu Ile Arg Tyr
        755                 760                 765

Asn Ala Lys His Glu Thr Leu Asn Val Pro Gly Thr Gly Ser Leu Trp
    770                 775                 780

Pro Leu Ala Val Lys Ser Pro Ile Gly Arg Cys Gly Glu Pro Asn Arg
785                 790                 795                 800

Cys Ala Pro Arg Ile Glu Trp Lys Pro Asp Val Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Lys Ile Gly Asn Leu Glu
    850                 855                 860

Phe Leu Glu Glu Lys Leu Leu Gly Glu Ala Leu Ala Arg Val Lys
865                 870                 875                 880

Lys Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asp Ser Gln Tyr Asn Arg Leu Gln Thr Asp Thr Asn Ile Ala Met
        915                 920                 925

Ile His Ala Ala Asp Lys Arg Val His Arg Ile Arg Glu Ala Tyr Leu
```

```
                    930             935             940
Pro Glu Leu Ser Val Ile Pro Gly Val Asn Ala Ala Ile Phe Glu Glu
945                 950             955                 960

Leu Glu Gly Leu Ile Phe Thr Ala Phe Ser Leu Tyr Asp Ala Arg Asn
                965             970             975

Val Ile Lys Asn Gly Asp Phe Asn Tyr Gly Leu Ser Cys Trp Asn Val
            980             985             990

Lys Gly His Val Asp Val Glu Glu Gln Asn Asn His Arg Ser Val Leu
        995             1000            1005

Val Ile Pro Glu Trp Glu Ala Glu Val Ser Gln Glu Val Arg Val
    1010            1015            1020

Cys Pro Gly Arg Gly Tyr Ile Leu Arg Val Thr Ala Tyr Lys Glu
    1025            1030            1035

Gly Tyr Gly Glu Gly Cys Val Thr Ile His Glu Ile Glu Asp Asn
    1040            1045            1050

Thr Asp Glu Leu Lys Phe Ser Asn Cys Val Glu Glu Val Tyr
    1055            1060            1065

Pro Asn Asn Thr Val Thr Cys Asn Asp Tyr Thr Ala Thr Gln Glu
    1070            1075            1080

Glu Tyr Glu Gly Thr Tyr Thr Ser Arg Asn Arg Gly Tyr Asp Gly
    1085            1090            1095

Ala Tyr Glu Ser Asn Ser Ser Val Pro Ala Asp Tyr Ala Ser Ala
    1100            1105            1110

Tyr Glu Glu Lys Ala Tyr Thr Asp Gly Arg Arg Asp Asn Pro Cys
    1115            1120            1125

Glu Ser Asn Arg Gly Tyr Arg Asp Tyr Thr Pro Leu Pro Ala Gly
    1130            1135            1140

Tyr Val Thr Lys Glu Leu Glu Tyr Phe Pro Glu Thr Asp Lys Val
    1145            1150            1155

Trp Ile Glu Ile Gly Glu Thr Glu Gly Thr Phe Ile Val Asp Ser
    1160            1165            1170

Val Glu Leu Leu Leu Met Glu Glu
    1175            1180

<210> SEQ ID NO 6
<211> LENGTH: 1193
<212> TYPE: PRT
<213> ORGANISM: Artificial Sequence
<220> FEATURE:
<223> OTHER INFORMATION: Hybrid toxin

<400> SEQUENCE: 6

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
```

```
            100             105             110
Ser Phe Arg Glu Trp Glu Ala Asp Pro Thr Asn Pro Ala Leu Arg Glu
        115             120             125

Glu Met Arg Ile Gln Phe Asn Asp Met Asn Ser Ala Leu Thr Thr Ala
        130             135             140

Ile Pro Leu Phe Ala Val Gln Asn Tyr Gln Val Pro Leu Leu Ser Val
145             150             155             160

Tyr Val Gln Ala Ala Asn Leu His Leu Ser Val Leu Arg Asp Val Ser
                165             170             175

Val Phe Gly Gln Arg Trp Gly Phe Asp Ala Ala Thr Ile Asn Ser Arg
            180             185             190

Tyr Asn Asp Leu Thr Arg Leu Ile Gly Asn Tyr Thr Asp His Ala Val
        195             200             205

Arg Trp Tyr Asn Thr Gly Leu Glu Arg Val Trp Gly Pro Asp Ser Arg
    210             215             220

Asp Trp Ile Arg Tyr Asn Gln Phe Arg Arg Glu Leu Thr Leu Thr Val
225             230             235             240

Leu Asp Ile Val Ser Leu Phe Pro Asn Tyr Asp Ser Arg Thr Tyr Pro
                245             250             255

Ile Arg Thr Val Ser Gln Leu Thr Arg Glu Ile Tyr Thr Asn Pro Val
            260             265             270

Leu Glu Asn Phe Asp Gly Ser Phe Arg Gly Ser Ala Gln Gly Ile Glu
        275             280             285

Gly Ser Ile Arg Ser Pro His Leu Met Asp Ile Leu Asn Ser Ile Thr
    290             295             300

Ile Tyr Thr Asp Ala His Arg Gly Glu Tyr Tyr Trp Ser Gly His Gln
305             310             315             320

Ile Met Ala Ser Pro Val Gly Phe Ser Gly Pro Glu Phe Thr Phe Pro
                325             330             335

Leu Tyr Gly Thr Met Gly Asn Ala Ala Pro Gln Gln Arg Ile Val Ala
            340             345             350

Gln Leu Gly Gln Gly Val Tyr Arg Thr Leu Ser Ser Thr Leu Tyr Arg
        355             360             365

Arg Pro Phe Asn Ile Gly Ile Asn Asn Gln Gln Leu Ser Val Leu Asp
    370             375             380

Gly Thr Glu Phe Ala Tyr Gly Thr Ser Ser Asn Leu Pro Ser Ala Val
385             390             395             400

Tyr Arg Lys Ser Gly Thr Val Asp Ser Leu Asp Glu Ile Pro Pro Gln
                405             410             415

Asn Asn Asn Val Pro Pro Arg Gln Gly Phe Ser His Arg Leu Ser His
            420             425             430

Val Ser Met Phe Arg Ser Gly Phe Ser Asn Ser Ser Val Ser Ile Ile
        435             440             445

Arg Ala Pro Met Phe Ser Trp Ile His Arg Ser Ala Thr Leu Thr Asn
    450             455             460

Thr Ile Asp Pro Glu Arg Ile Asn Gln Ile Pro Leu Val Lys Gly Phe
465             470             475             480

Arg Val Trp Gly Gly Thr Ser Val Ile Thr Gly Pro Gly Phe Thr Gly
                485             490             495

Gly Asp Ile Leu Arg Arg Asn Thr Phe Gly Asp Phe Val Ser Leu Gln
            500             505             510

Val Asn Ile Asn Ser Pro Ile Thr Gln Arg Tyr Arg Leu Arg Phe Arg
        515             520             525
```

```
Tyr Ala Ser Ser Arg Asp Ala Arg Val Ile Val Leu Thr Gly Ala Ala
    530                 535                 540

Ser Thr Gly Val Gly Gly Gln Val Ser Val Asn Met Pro Leu Gln Lys
545                 550                 555                 560

Thr Met Glu Ile Gly Glu Asn Leu Thr Ser Arg Thr Phe Arg Tyr Thr
                565                 570                 575

Asp Phe Ser Asn Pro Phe Ser Phe Arg Ala Asn Pro Asp Ile Ile Gly
            580                 585                 590

Ile Ser Glu Gln Pro Leu Phe Gly Ala Gly Ser Ile Ser Ser Gly Glu
        595                 600                 605

Leu Tyr Ile Asp Lys Ile Glu Ile Ile Leu Ala Asp Ala Thr Phe Glu
    610                 615                 620

Ala Glu Ser Asp Leu Glu Arg Ala Gln Lys Ala Val Asn Ala Leu Phe
625                 630                 635                 640

Thr Ser Ser Asn Gln Ile Gly Leu Lys Thr Asp Val Thr Asp Tyr His
                645                 650                 655

Ile Asp Gln Val Ser Asn Leu Val Asp Cys Leu Ser Asp Glu Phe Cys
            660                 665                 670

Leu Asp Glu Lys Lys Glu Leu Ser Glu Lys Val Lys His Ala Lys Arg
        675                 680                 685

Leu Ser Asp Glu Arg Asn Leu Leu Gln Asp Pro Asn Phe Arg Gly Ile
    690                 695                 700

Asn Arg Gln Leu Asp Arg Gly Trp Arg Gly Ser Thr Asp Ile Thr Ile
705                 710                 715                 720

Gln Gly Gly Asp Asp Val Phe Lys Glu Asn Tyr Val Thr Leu Gln Gly
                725                 730                 735

Thr Phe Asp Glu Cys Tyr Pro Thr Tyr Leu Tyr Gln Pro Ile Asp Glu
            740                 745                 750

Ser Lys Leu Lys Ala Tyr Thr Arg Tyr Gln Leu Arg Gly Tyr Ile Glu
        755                 760                 765

Asp Ser Gln Asp Leu Glu Ile Tyr Leu Ile Arg Tyr Asn Ala Lys His
    770                 775                 780

Glu Thr Val Asn Val Pro Gly Thr Gly Ser Leu Trp Pro Pro Ser Ala
785                 790                 795                 800

Pro Ser Pro Ile Gly Lys Cys Gly Glu Pro Asn Arg Cys Ala Pro His
                805                 810                 815

Leu Glu Trp Asn Pro Asp Leu Asp Cys Ser Cys Arg Asp Gly Glu Lys
            820                 825                 830

Cys Ala His His Ser His His Phe Ser Leu Asp Ile Asp Val Gly Cys
        835                 840                 845

Thr Asp Leu Asn Glu Asp Leu Gly Val Trp Val Ile Phe Lys Ile Lys
    850                 855                 860

Thr Gln Asp Gly His Ala Arg Leu Gly Asn Leu Glu Phe Leu Glu Glu
865                 870                 875                 880

Lys Pro Leu Val Gly Glu Ala Leu Ala Arg Val Lys Arg Ala Glu Lys
                885                 890                 895

Lys Trp Arg Asp Lys Arg Glu Lys Leu Glu Trp Glu Thr Asn Ile Val
            900                 905                 910

Tyr Lys Glu Ala Lys Glu Ser Val Asp Ala Leu Phe Val Asn Ser Gln
        915                 920                 925

Tyr Asp Arg Leu Gln Ala Asp Thr Asn Ile Ala Met Ile His Ala Ala
    930                 935                 940
```

Asp Lys Arg Val His Ser Ile Arg Glu Ala Tyr Leu Pro Glu Leu Ser
945                 950                 955                 960

Val Ile Pro Gly Val Asn Ala Ala Ile Phe Glu Glu Leu Glu Gly Arg
                965                 970                 975

Ile Phe Thr Ala Phe Ser Leu Tyr Asp Ala Arg Asn Val Ile Lys Asn
                980                 985                 990

Gly Asp Phe Asn Asn Gly Leu Ser Cys Trp Asn Val Lys Gly His Val
            995                 1000                1005

Asp Val Glu Glu Gln Asn Asn His Arg Ser Val Leu Val Val Pro
    1010                1015                1020

Glu Trp Glu Ala Glu Val Ser Gln Glu Val Arg Val Cys Pro Gly
    1025                1030                1035

Arg Gly Tyr Ile Leu Arg Val Thr Ala Tyr Lys Glu Gly Tyr Gly
    1040                1045                1050

Glu Gly Cys Val Thr Ile His Glu Ile Glu Asn Asn Thr Asp Glu
    1055                1060                1065

Leu Lys Phe Ser Asn Cys Val Glu Glu Val Tyr Pro Asn Asn
    1070                1075                1080

Thr Val Thr Cys Asn Asp Tyr Thr Ala Thr Gln Glu Glu Tyr Glu
    1085                1090                1095

Gly Thr Tyr Thr Ser Arg Asn Arg Gly Tyr Asp Gly Ala Tyr Glu
    1100                1105                1110

Ser Asn Ser Ser Val Pro Ala Asp Tyr Ala Ser Ala His Glu Glu
    1115                1120                1125

Lys Ala Tyr Thr Asp Gly Arg Arg Asp Asn Pro Cys Glu Ser Asn
    1130                1135                1140

Arg Gly Tyr Gly Asp Tyr Thr Pro Leu Pro Ala Gly Tyr Val Thr
    1145                1150                1155

Lys Glu Leu Glu Tyr Phe Pro Glu Thr Asp Lys Val Trp Ile Glu
    1160                1165                1170

Ile Gly Glu Thr Glu Gly Thr Phe Ile Val Asp Ser Val Glu Leu
    1175                1180                1185

Leu Leu Met Glu Glu
    1190

<210> SEQ ID NO 7
<211> LENGTH: 881
<212> TYPE: PRT
<213> ORGANISM: Artificial Sequence
<220> FEATURE:
<223> OTHER INFORMATION: Hybrid toxin

<400> SEQUENCE: 7

Met Asp Ile Leu Asn Ser Ile Thr Ile Tyr Thr Asp Ala His Arg Gly
1               5                   10                  15

Glu Tyr Tyr Trp Ser Gly His Gln Ile Met Ala Ser Pro Val Gly Phe
                20                  25                  30

Ser Gly Pro Glu Phe Thr Phe Pro Leu Tyr Gly Thr Met Gly Asn Ala
            35                  40                  45

Ala Pro Gln Gln Arg Ile Val Ala Gln Leu Gly Gln Gly Val Tyr Arg
        50                  55                  60

Thr Leu Ser Ser Thr Leu Tyr Arg Arg Pro Phe Asn Ile Gly Ile Asn
65                  70                  75                  80

Asn Gln Gln Leu Ser Val Leu Asp Gly Thr Glu Phe Ala Tyr Gly Thr
                85                  90                  95

-continued

```
Ser Ser Asn Leu Pro Ser Ala Val Tyr Arg Lys Ser Gly Thr Val Asp
            100                 105                 110

Ser Leu Asp Glu Ile Pro Pro Gln Asn Asn Val Pro Pro Arg Gln
        115                 120                 125

Gly Phe Ser His Arg Leu Ser His Val Ser Met Phe Arg Ser Gly Phe
        130                 135                 140

Ser Asn Ser Ser Val Ser Ile Ile Arg Ala Pro Met Phe Ser Trp Ile
145                 150                 155                 160

His Arg Ser Ala Glu Phe Asn Asn Ile Ile Ala Ser Asp Ser Ile Thr
                165                 170                 175

Gln Ile Pro Leu Val Lys Ala His Thr Leu Gln Ser Gly Thr Thr Val
            180                 185                 190

Val Arg Gly Pro Gly Phe Thr Gly Gly Asp Ile Leu Arg Arg Thr Ser
        195                 200                 205

Gly Gly Pro Phe Ala Tyr Thr Ile Val Asn Ile Asn Gly Gln Leu Pro
        210                 215                 220

Gln Arg Tyr Arg Ala Arg Ile Arg Tyr Ala Ser Thr Thr Asn Leu Arg
225                 230                 235                 240

Ile Tyr Val Thr Val Ala Gly Glu Arg Ile Phe Ala Gly Gln Phe Asn
                245                 250                 255

Lys Thr Met Asp Thr Gly Asp Pro Leu Thr Phe Gln Ser Phe Ser Tyr
            260                 265                 270

Ala Thr Ile Asn Thr Ala Phe Thr Phe Pro Met Ser Gln Ser Ser Phe
        275                 280                 285

Thr Val Gly Ala Asp Thr Phe Ser Ser Gly Asn Glu Val Tyr Ile Asp
        290                 295                 300

Arg Phe Glu Leu Ile Pro Val Thr Ala Thr Leu Glu Ala Glu Tyr Asn
305                 310                 315                 320

Leu Glu Arg Ala Gln Lys Ala Val Asn Ala Leu Phe Thr Ser Thr Asn
                325                 330                 335

Gln Leu Gly Leu Lys Thr Asn Val Thr Asp Tyr His Ile Asp Gln Val
            340                 345                 350

Ser Asn Leu Val Thr Tyr Leu Ser Asp Glu Phe Cys Leu Asp Glu Lys
        355                 360                 365

Arg Glu Leu Ser Glu Lys Val Lys His Ala Lys Arg Leu Ser Asp Glu
        370                 375                 380

Arg Asn Leu Leu Gln Asp Ser Asn Phe Lys Asp Ile Asn Arg Gln Pro
385                 390                 395                 400

Glu Arg Gly Trp Gly Gly Ser Thr Gly Ile Thr Ile Gln Gly Gly Asp
                405                 410                 415

Asp Val Phe Lys Glu Asn Tyr Val Thr Leu Ser Gly Thr Phe Asp Glu
            420                 425                 430

Cys Tyr Pro Thr Tyr Leu Tyr Gln Lys Ile Asp Glu Ser Lys Leu Lys
        435                 440                 445

Ala Phe Thr Arg Tyr Gln Leu Arg Gly Tyr Ile Glu Asp Ser Gln Asp
        450                 455                 460

Leu Glu Ile Tyr Ser Ile Arg Tyr Asn Ala Lys His Glu Thr Val Asn
465                 470                 475                 480

Val Pro Gly Thr Gly Ser Leu Trp Pro Leu Ser Ala Gln Ser Pro Ile
                485                 490                 495

Gly Lys Cys Gly Glu Pro Asn Arg Cys Ala Pro His Leu Glu Trp Asn
            500                 505                 510

Pro Asp Leu Asp Cys Ser Cys Arg Asp Gly Glu Lys Cys Ala His His
```

```
                515                 520                 525
Ser His His Phe Ser Leu Asp Ile Asp Val Gly Cys Thr Asp Leu Asn
    530                 535                 540

Glu Asp Leu Gly Val Trp Val Ile Phe Lys Ile Lys Thr Gln Asp Gly
545                 550                 555                 560

His Ala Arg Leu Gly Asn Leu Glu Phe Leu Glu Lys Pro Leu Val
                565                 570                 575

Gly Glu Ala Leu Ala Arg Val Lys Arg Ala Glu Lys Lys Trp Arg Asp
            580                 585                 590

Lys Arg Glu Lys Leu Glu Trp Glu Thr Asn Ile Val Tyr Lys Glu Ala
        595                 600                 605

Lys Glu Ser Val Asp Ala Leu Phe Val Asn Ser Gln Tyr Asp Gln Leu
    610                 615                 620

Gln Ala Asp Thr Asn Ile Ala Met Ile His Ala Ala Asp Lys Arg Val
625                 630                 635                 640

His Ser Ile Arg Glu Ala Tyr Leu Pro Glu Leu Ser Val Ile Pro Gly
                645                 650                 655

Val Asn Ala Ala Ile Phe Glu Glu Leu Glu Gly Arg Ile Phe Thr Ala
            660                 665                 670

Phe Ser Leu Tyr Asp Ala Arg Asn Val Ile Lys Asn Gly Asp Phe Asn
        675                 680                 685

Asn Gly Leu Ser Cys Trp Asn Val Lys Gly His Val Asp Val Glu Glu
    690                 695                 700

Gln Asn Asn Gln Arg Ser Val Leu Val Val Pro Glu Trp Glu Ala Glu
705                 710                 715                 720

Val Ser Gln Glu Val Arg Val Cys Pro Gly Arg Gly Tyr Ile Leu Arg
                725                 730                 735

Val Thr Ala Tyr Lys Glu Gly Tyr Gly Glu Gly Cys Val Thr Ile His
            740                 745                 750

Glu Ile Glu Asn Asn Thr Asp Glu Leu Lys Phe Ser Asn Cys Val Glu
        755                 760                 765

Glu Glu Ile Tyr Pro Asn Asn Thr Val Thr Cys Asn Asp Tyr Thr Val
770                 775                 780

Asn Gln Glu Glu Tyr Gly Gly Ala Tyr Thr Ser Arg Asn Arg Gly Tyr
785                 790                 795                 800

Asn Glu Ala Pro Ser Val Pro Ala Asp Tyr Ala Ser Val Tyr Glu Glu
                805                 810                 815

Lys Ser Tyr Thr Asp Gly Arg Arg Glu Asn Pro Cys Glu Phe Asn Arg
            820                 825                 830

Gly Tyr Arg Asp Tyr Thr Pro Leu Pro Val Gly Tyr Val Thr Lys Glu
        835                 840                 845

Leu Glu Tyr Phe Pro Glu Thr Asp Lys Val Trp Ile Glu Ile Gly Glu
    850                 855                 860

Thr Glu Gly Thr Phe Ile Val Asp Ser Val Glu Leu Leu Leu Met Glu
865                 870                 875                 880

Glu

<210> SEQ ID NO 8
<211> LENGTH: 66
<212> TYPE: PRT
<213> ORGANISM: Sulfolobusacidocaldarius

<400> SEQUENCE: 8

Met Val Lys Val Lys Phe Lys Tyr Lys Gly Glu Glu Lys Glu Val Asp
```

```
1               5                   10                  15
Thr Ser Lys Ile Lys Lys Val Trp Arg Val Gly Lys Met Val Ser Phe
                20                  25                  30

Thr Tyr Asp Asp Asn Gly Lys Thr Gly Arg Gly Ala Val Ser Glu Lys
                35                  40                  45

Asp Ala Pro Lys Glu Leu Leu Asp Met Leu Ala Arg Ala Glu Arg Glu
                50                  55                  60

Lys Lys
65

<210> SEQ ID NO 9
<211> LENGTH: 66
<212> TYPE: PRT
<213> ORGANISM: Artificial Sequence
<220> FEATURE:
<223> OTHER INFORMATION: synNAPS

<400> SEQUENCE: 9

Met Val Lys Val Lys Phe Gly Pro Trp Gly Glu Glu Lys Glu Val Asp
1               5                   10                  15

Thr Ser Lys Ile Val Asp Val Trp Arg Trp Gly Lys Tyr Val Asp Phe
                20                  25                  30

Phe Tyr Asp Asp Asn Gly Lys Val Gly Ile Gly Ser Val Thr Glu Lys
                35                  40                  45

Asp Ala Pro Lys Glu Leu Leu Asp Met Leu Ala Arg Ala Glu Arg Glu
                50                  55                  60

Lys Lys
65

<210> SEQ ID NO 10
<211> LENGTH: 66
<212> TYPE: PRT
<213> ORGANISM: Artificial Sequence
<220> FEATURE:
<223> OTHER INFORMATION: synNAPS

<400> SEQUENCE: 10

Met Val Lys Val Lys Phe Lys Tyr Lys Gly Glu Glu Lys Glu Val Asp
1               5                   10                  15

Thr Ser Lys Ile Val Trp Ile Gly Arg Phe Gly Lys Ser Val Tyr Phe
                20                  25                  30

Arg Tyr Asp Asp Asn Gly Lys Thr Gly Ala Gly Arg Val Tyr Glu Lys
                35                  40                  45

Asp Ala Pro Lys Glu Leu Leu Asp Met Leu Ala Arg Ala Glu Arg Glu
                50                  55                  60

Lys Lys
65

<210> SEQ ID NO 11
<211> LENGTH: 66
<212> TYPE: PRT
<213> ORGANISM: Artificial Sequence
<220> FEATURE:
<223> OTHER INFORMATION: synNAPS

<400> SEQUENCE: 11

Met Val Lys Val Lys Phe Arg Trp Gly Gly Glu Glu Lys Glu Val Asp
1               5                   10                  15

Thr Ser Lys Ile Trp Tyr Val Ala Arg Val Gly Lys Trp Val Leu Phe
                20                  25                  30
```

Gly Tyr Asp Asp Asn Gly Lys Arg Gly Ala Gly Arg Val Arg Glu Lys
            35                  40                  45

Asp Ala Pro Lys Glu Leu Leu Asp Met Leu Ala Arg Ala Glu Arg Glu
        50                  55                  60

Lys Lys
65

<210> SEQ ID NO 12
<211> LENGTH: 66
<212> TYPE: PRT
<213> ORGANISM: Artificial Sequence
<220> FEATURE:
<223> OTHER INFORMATION: synNAPS

<400> SEQUENCE: 12

Met Val Lys Val Lys Phe Lys Tyr Lys Gly Glu Glu Lys Glu Val Asp
1               5                   10                  15

Thr Ser Lys Ile Ser Tyr Val Gln Arg Ala Gly Lys Ser Val Tyr Phe
            20                  25                  30

Asn Tyr Asp Asp Asn Gly Lys Thr Gly Gly Gly Arg Val Phe Glu Lys
            35                  40                  45

Asp Ala Pro Lys Glu Leu Leu Asp Met Leu Ala Arg Ala Glu Arg Glu
        50                  55                  60

Lys Lys
65

<210> SEQ ID NO 13
<211> LENGTH: 66
<212> TYPE: PRT
<213> ORGANISM: Artificial Sequence
<220> FEATURE:
<223> OTHER INFORMATION: synNAPS

<400> SEQUENCE: 13

Met Val Lys Val Lys Phe Val Leu Lys Gly Glu Glu Lys Glu Val Asp
1               5                   10                  15

Thr Ser Lys Ile Thr Tyr Val Ala Arg Tyr Gly Lys Phe Val Gln Phe
            20                  25                  30

Asp Tyr Asp Asp Asn Gly Lys Phe Gly Ala Gly Val Val Leu Glu Lys
            35                  40                  45

Asp Ala Pro Lys Glu Leu Leu Asp Met Leu Ala Arg Ala Glu Arg Glu
        50                  55                  60

Lys Lys
65

<210> SEQ ID NO 14
<211> LENGTH: 66
<212> TYPE: PRT
<213> ORGANISM: Artificial Sequence
<220> FEATURE:
<223> OTHER INFORMATION: synNAPS

<400> SEQUENCE: 14

Met Val Lys Val Lys Phe Met Arg Trp Gly Glu Glu Lys Glu Val Asp
1               5                   10                  15

Thr Ser Lys Ile Thr Tyr Val Thr Arg Trp Gly Lys Thr Val Ile Phe
            20                  25                  30

Tyr Tyr Asp Asp Asn Gly Lys Lys Gly His Gly Ser Val Leu Glu Lys
            35                  40                  45

```
Asp Ala Pro Lys Glu Leu Leu Asp Met Leu Ala Arg Ala Glu Arg Glu
         50                  55                  60

Lys Lys
65

<210> SEQ ID NO 15
<211> LENGTH: 66
<212> TYPE: PRT
<213> ORGANISM: Artificial Sequence
<220> FEATURE:
<223> OTHER INFORMATION: synNAPS

<400> SEQUENCE: 15

Met Val Lys Val Lys Phe Lys Val His Gly Lys Glu Lys Glu Val Asp
1               5                   10                  15

Thr Ser Lys Ile Leu Ala Val Ala Arg Trp Gly Lys Ala Val Ile Phe
            20                  25                  30

Ala Tyr Asp Asp Asn Gly Lys His Gly Arg Gly Gln Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 16
<211> LENGTH: 66
<212> TYPE: PRT
<213> ORGANISM: Artificial Sequence
<220> FEATURE:
<223> OTHER INFORMATION: synNAPS

<400> SEQUENCE: 16

Met Val Lys Val Lys Phe His Gly Arg Gly Glu Glu Lys Glu Val Asp
1               5                   10                  15

Thr Ser Lys Ile Phe Trp Val Tyr Arg Asp Gly Lys Arg Val Leu Phe
            20                  25                  30

Arg Tyr Asp Asp Asn Gly Lys Arg Gly Phe Gly Ser Val Pro Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 17
<211> LENGTH: 66
<212> TYPE: PRT
<213> ORGANISM: Artificial Sequence
<220> FEATURE:
<223> OTHER INFORMATION: synNAPS

<400> SEQUENCE: 17

Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ile Val Phe Phe
            20                  25                  30

Met Tyr Asp Asp Asn Gly Lys Gly Gly Phe Gly His Val Thr Glu Lys
        35                  40                  45

Asp Ala Pro Lys Glu Leu Leu Asp Met Leu Ala Arg Ala Glu Arg Glu
    50                  55                  60

Lys Lys
```

<210> SEQ ID NO 18
<211> LENGTH: 66
<212> TYPE: PRT
<213> ORGANISM: Artificial Sequence
<220> FEATURE:
<223> OTHER INFORMATION: synNAPS

<400> SEQUENCE: 18

Met Val Lys Val Lys Phe Leu Met Lys Gly Glu Glu Lys Glu Val Asp
1               5                   10                  15

Thr Ser Lys Ile Lys Trp Val Asn Arg His Gly Lys Tyr Val Ala Phe
            20                  25                  30

Tyr Tyr Asp Asp Asn Gly Lys Thr Gly Gly Gly Glu Val Arg Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 19
<211> LENGTH: 66
<212> TYPE: PRT
<213> ORGANISM: Artificial Sequence
<220> FEATURE:
<223> OTHER INFORMATION: synNAPS

<400> SEQUENCE: 19

Met Val Lys Val Lys Phe Gly Leu Gly Gly Glu Glu Lys Glu Val Asp
1               5                   10                  15

Thr Ser Lys Ile Arg Arg Val Leu Arg Leu Gly Lys Leu Val Ser Phe
            20                  25                  30

Thr Tyr Asp Asp Asn Gly Lys Ile Gly Leu Gly Asp Val His Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 20
<211> LENGTH: 66
<212> TYPE: PRT
<213> ORGANISM: Artificial Sequence
<220> FEATURE:
<223> OTHER INFORMATION: synNAPS

<400> SEQUENCE: 20

Met Val Lys Val Lys Phe Lys Leu Thr Gly Glu Glu Lys Glu Val Asp
1               5                   10                  15

Thr Ser Lys Ile Gln Trp Val Ala Arg Phe Gly Lys Phe Val Asp Phe
            20                  25                  30

Leu Tyr Asp Asp Asn Gly Lys Thr Gly Trp Gly Trp Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 21

-continued

```
<211> LENGTH: 66
<212> TYPE: PRT
<213> ORGANISM: Artificial Sequnece
<220> FEATURE:
<223> OTHER INFORMATION: synNAPS

<400> SEQUENCE: 21

Met Val Lys Val Lys Phe Lys Arg Trp Gly Glu Glu Lys Glu Val Asp
1               5                   10                  15

Thr Ser Lys Ile Leu His Val Leu Arg Val Gly Lys Tyr Val Arg Phe
            20                  25                  30

Ser Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 22
<211> LENGTH: 66
<212> TYPE: PRT
<213> ORGANISM: Artificial Sequence
<220> FEATURE:
<223> OTHER INFORMATION: synNAPS

<400> SEQUENCE: 22

Met Val Lys Val Lys Phe Lys Tyr Lys Gly Glu Glu Lys Glu Val Asp
1               5                   10                  15

Thr Ser Lys Ile Ile Phe Val Tyr Arg Phe Gly Lys Phe Val Met Phe
            20                  25                  30

Ile Tyr Asp Asp Asn Gly Lys Thr Gly His Gly Asp Val Arg Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 23
<211> LENGTH: 94
<212> TYPE: PRT
<213> ORGANISM: Artificial Sequence
<220> FEATURE:
<223> OTHER INFORMATION: synNAPS

<400> SEQUENCE: 23

Met Arg Gly Ser His His His His His His Gly Ser Val Lys Val Lys
1               5                   10                  15

Phe Gly Pro Trp Gly Glu Glu Lys Glu Val Asp Thr Ser Lys Ile Val
            20                  25                  30

Asp Val Trp Arg Trp Gly Lys Tyr Val Asp Phe Phe Tyr Asp Asp Asn
        35                  40                  45

Gly Lys Val Gly Ile Gly Ser Val Thr Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 24
<211> LENGTH: 94
```

```
<212> TYPE: PRT
<213> ORGANISM: Artificial Sequence
<220> FEATURE:
<223> OTHER INFORMATION: synNAPS

<400> SEQUENCE: 24

Met Arg Gly Ser His His His His His His Gly Ser Val Lys Val Lys
1               5                   10                  15

Phe Lys Tyr Lys Gly Glu Glu Lys Glu Val Asp Thr Ser Lys Ile Val
            20                  25                  30

Trp Ile Gly Arg Phe Gly Lys Ser Val Tyr Phe Arg Tyr Asp Asp Asn
        35                  40                  45

Gly Lys Thr Gly Ala Gly Arg Val Tyr Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 25
<211> LENGTH: 94
<212> TYPE: PRT
<213> ORGANISM: Artificial Sequence
<220> FEATURE:
<223> OTHER INFORMATION: synNAPS

<400> SEQUENCE: 25

Met Arg Gly Ser His His His His His His Gly Ser Val Lys Val Lys
1               5                   10                  15

Phe Arg Trp Gly Gly Glu Glu Lys Glu Val Asp Thr Ser Lys Ile Trp
            20                  25                  30

Tyr Val Ala Arg Val Gly Lys Trp Val Leu Phe Gly Tyr Asp Asp Asn
        35                  40                  45

Gly Lys Arg Gly Ala Gly Arg Val Arg Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 26
<211> LENGTH: 94
<212> TYPE: PRT
<213> ORGANISM: Artificial Sequence
<220> FEATURE:
<223> OTHER INFORMATION: synNAPS

<400> SEQUENCE: 26

Met Arg Gly Ser His His His His His His Gly Ser Val Lys Val Lys
1               5                   10                  15

Phe Lys Tyr Lys Gly Glu Glu Lys Glu Val Asp Thr Ser Lys Ile Ser
            20                  25                  30

Tyr Val Gln Arg Ala Gly Lys Ser Val Tyr Phe Asn Tyr Asp Asp Asn
        35                  40                  45

Gly Lys Thr Gly Gly Gly Arg Val Phe Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
```

<210> SEQ ID NO 27
<211> LENGTH: 94
<212> TYPE: PRT
<213> ORGANISM: Artificial Sequence
<220> FEATURE:
<223> OTHER INFORMATION: synNAPS

<400> SEQUENCE: 27

Met Arg Gly Ser His His His His His His Gly Ser Val Lys Val Lys
1               5                   10                  15

Phe Val Leu Lys Gly Glu Glu Lys Glu Val Asp Thr Ser Lys Ile Thr
            20                  25                  30

Tyr Val Ala Arg Tyr Gly Lys Phe Val Gln Phe Asp Tyr Asp Asp Asn
        35                  40                  45

Gly Lys Phe Gly Ala Gly Val Val Leu Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 28
<211> LENGTH: 94
<212> TYPE: PRT
<213> ORGANISM: Artificial Sequence
<220> FEATURE:
<223> OTHER INFORMATION: synNAPS

<400> SEQUENCE: 28

Met Arg Gly Ser His His His His His His Gly Ser Val Lys Val Lys
1               5                   10                  15

Phe Met Arg Trp Gly Glu Glu Lys Glu Val Asp Thr Ser Lys Ile Thr
            20                  25                  30

Tyr Val Thr Arg Trp Gly Lys Thr Val Ile Phe Tyr Tyr Asp Asp Asn
        35                  40                  45

Gly Lys Lys Gly His Gly Ser Val Leu Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 29
<211> LENGTH: 94
<212> TYPE: PRT
<213> ORGANISM: Artificial Sequence
<220> FEATURE:
<223> OTHER INFORMATION: synNAPS

<400> SEQUENCE: 29

Met Arg Gly Ser His His His His His His Gly Ser Val Lys Val Lys
1               5                   10                  15

Phe Lys Val His Gly Lys Glu Lys Glu Val Asp Thr Ser Lys Ile Leu
            20                  25                  30

Ala Val Ala Arg Trp Gly Lys Ala Val Ile Phe Ala Tyr Asp Asp Asn
        35                  40                  45

Gly Lys His Gly Arg Gly Gln Val Ser Glu Lys Asp Ala Pro Lys Glu
    50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 30
<211> LENGTH: 94
<212> TYPE: PRT
<213> ORGANISM: Artificial Sequence
<220> FEATURE:
<223> OTHER INFORMATION: synNAPS

<400> SEQUENCE: 30

Met Arg Gly Ser His His His His His Gly Ser Val Lys Val Lys
1               5                   10                  15

Phe Lys Val His Gly Lys Glu Lys Glu Val Asp Thr Ser Lys Ile Leu
                20                  25                  30

Ala Val Ala Arg Trp Gly Lys Ala Val Ile Phe Ala Tyr Asp Asp Asn
            35                  40                  45

Gly Lys His Gly Arg Gly Gln Val Ser Glu Lys Asp Ala Pro Lys Glu
        50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 31
<211> LENGTH: 94
<212> TYPE: PRT
<213> ORGANISM: Artificial Sequence
<220> FEATURE:
<223> OTHER INFORMATION: synNAPS

<400> SEQUENCE: 31

Met Arg Gly Ser His His His His His Gly Ser Val Lys Val Lys
1               5                   10                  15

Phe Ala Gln Gly Gly Glu Glu Lys Glu Val Asp Thr Ser Lys Ile Tyr
                20                  25                  30

Arg Val Pro Arg His Gly Lys Ile Val Phe Phe Met Tyr Asp Asp Asn
            35                  40                  45

Gly Lys Gly Gly Phe Gly His Val Thr Glu Lys Asp Ala Pro Lys Glu
        50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 32
<211> LENGTH: 94
<212> TYPE: PRT
<213> ORGANISM: Artificial Sequence
<220> FEATURE:
<223> OTHER INFORMATION: synNAPS

<400> SEQUENCE: 32

Met Arg Gly Ser His His His His His Gly Ser Val Lys Val Lys
1               5                   10                  15

Phe Leu Met Lys Gly Glu Glu Lys Glu Val Asp Thr Ser Lys Ile Lys
                20                  25                  30

Trp Val Asn Arg His Gly Lys Tyr Val Ala Phe Tyr Tyr Asp Asp Asn
            35                  40                  45

Gly Lys Thr Gly Gly Glu Val Arg Glu Lys Asp Ala Pro Lys Glu
 50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 33
<211> LENGTH: 94
<212> TYPE: PRT
<213> ORGANISM: Artificial Sequence
<220> FEATURE:
<223> OTHER INFORMATION: synNAPS

<400> SEQUENCE: 33

Met Arg Gly Ser His His His His His His Gly Ser Val Lys Val Lys
1               5                   10                  15

Phe Gly Leu Gly Gly Glu Lys Glu Val Asp Thr Ser Lys Ile Arg
            20                  25                  30

Arg Val Leu Arg Leu Gly Lys Leu Val Ser Phe Thr Tyr Asp Asp Asn
            35                  40                  45

Gly Lys Ile Gly Leu Gly Asp Val His Glu Lys Asp Ala Pro Lys Glu
 50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 34
<211> LENGTH: 94
<212> TYPE: PRT
<213> ORGANISM: Artificial Sequence
<220> FEATURE:
<223> OTHER INFORMATION: synNAPS

<400> SEQUENCE: 34

Met Arg Gly Ser His His His His His His Gly Ser Val Lys Val Lys
1               5                   10                  15

Phe Lys Leu Thr Gly Glu Glu Lys Glu Val Asp Thr Ser Lys Ile Gln
            20                  25                  30

Trp Val Ala Arg Phe Gly Lys Phe Val Asp Phe Leu Tyr Asp Asp Asn
            35                  40                  45

Gly Lys Thr Gly Trp Gly Trp Val Tyr Glu Lys Asp Ala Pro Lys Glu
 50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 35
<211> LENGTH: 94
<212> TYPE: PRT
<213> ORGANISM: Artificial Sequence
<220> FEATURE:
<223> OTHER INFORMATION: synNAPS

<400> SEQUENCE: 35

Met Arg Gly Ser His His His His His His Gly Ser Val Lys Val Lys

```
                  1               5                  10                  15
                Phe Lys Arg Trp Gly Glu Glu Lys Glu Val Asp Thr Ser Lys Ile Leu
                                20                  25                  30

His Val Leu Arg Val Gly Lys Tyr Val Arg Phe Ser Tyr Asp Asp Asn
                                35                  40                  45

Gly Lys Leu Gly Ala Gly Tyr Val Thr Glu Lys Asp Ala Pro Lys Glu
                                50                  55                  60

Leu Leu Asp Met Leu Ala Arg Ala Glu Arg Glu Lys Lys Leu Gly Ser
                65                  70                  75                  80

Gly Leu Asn Asp Ile Phe Glu Ala Gln Lys Ile Glu Trp His
                                85                  90

<210> SEQ ID NO 36
<211> LENGTH: 94
<212> TYPE: PRT
<213> ORGANISM: Artificial Sequence
<220> FEATURE:
<223> OTHER INFORMATION: synNAPS

<400> SEQUENCE: 36

Met Arg Gly Ser His His His His His His Gly Ser Val Lys Val Lys
1               5                   10                  15

Phe Lys Tyr Lys Gly Glu Glu Lys Glu Val Asp Thr Ser Lys Ile Ile
                20                  25                  30

Phe Val Tyr Arg Phe Gly Lys Phe Val Met Phe Ile Tyr Asp Asp Asn
                35                  40                  45

Gly Lys Thr Gly His Gly Asp Val Arg Glu Lys Asp Ala Pro Lys Glu
                50                  55                  60

Leu Leu Asp Met Leu Ala Arg Ala Glu Arg Glu Lys Lys Leu Gly Ser
65                  70                  75                  80

Gly Leu Asn Asp Ile Phe Glu Ala Gln Lys Ile Glu Trp His
                85                  90

<210> SEQ ID NO 37
<211> LENGTH: 11
<212> TYPE: PRT
<213> ORGANISM: Artificial Sequence
<220> FEATURE:
<223> OTHER INFORMATION: His-tag

<400> SEQUENCE: 37

Arg Gly Ser His His His His His His Gly Ser
1               5                   10

<210> SEQ ID NO 38
<211> LENGTH: 17
<212> TYPE: PRT
<213> ORGANISM: Artificial Sequence
<220> FEATURE:
<223> OTHER INFORMATION: Avidin-tag

<400> SEQUENCE: 38

Leu Gly Ser Gly Leu Asn Asp Ile Phe Glu Ala Gln Lys Ile Glu Trp
1               5                   10                  15

His

<210> SEQ ID NO 39
<211> LENGTH: 285
<212> TYPE: DNA
<213> ORGANISM: Artificial Sequence
<220> FEATURE:
```

<223> OTHER INFORMATION: synNAPS

<400> SEQUENCE: 39

```
atgagaggat cgcatcacca tcaccatcac ggatccgtca aggtgaaatt caaatataaa      60
ggcgaagaaa aagaagtgga cactagtaag atcgtgtgga ttgggcgttt cggcaaatcc     120
gtgtactttc gctacgacga caacggcaag accggcgccg gcagggtgta cgagaaagat     180
gccccgaaag agttattaga tatgttagcg cgtgcggaac gcgagaaaaa gcttggctcg     240
ggtctgaacg atatcttcga agctcagaaa atcgaatggc acgaa                    285
```

<210> SEQ ID NO 40
<211> LENGTH: 285
<212> TYPE: DNA
<213> ORGANISM: Artificial Sequence
<220> FEATURE:
<223> OTHER INFORMATION: synNAPS

<400> SEQUENCE: 40

```
atgagaggat cgcatcacca tcaccatcac ggatccgtca aggtgaaatt cgcccagggg      60
ggcgaagaaa aagaagtgga cactagtaag atctaccgcg ttccccgtca cggcaaaatc     120
gtgttctttta tgtacgacga caacggcaag ggggcttcg gccacgtgac cgagaaagat     180
gccccgaaag agttattaga tatgttagcg cgtgcggaac gcgagaaaaa gcttggctcg     240
ggtctgaacg atatcttcga agctcagaaa atcgaatggc acgaa                    285
```

<210> SEQ ID NO 41
<211> LENGTH: 285
<212> TYPE: DNA
<213> ORGANISM: Artificial Sequence
<220> FEATURE:
<223> OTHER INFORMATION: synNAPS

<400> SEQUENCE: 41

```
atgagaggat cgcatcacca tcaccatcac ggatccgtca aggtgaaatt caagcggtgg      60
ggcgaagaaa aagaagtgga cactagtaag atcctgcacg ttctccgtgt gggcaaatac     120
gtgcgcttta gctacgacga caacggcaag ctgggcgcgg gctacgtgac cgagaaagat     180
gccccgaaag agttattaga tatgttagcg cgtgcggaac gcgagaaaaa gcttggctcg     240
ggtctgaacg atatcttcga agctcagaaa atcgaatggc acgaa                    285
```

<210> SEQ ID NO 42
<211> LENGTH: 40
<212> TYPE: PRT
<213> ORGANISM: Artificial Sequence
<220> FEATURE:
<223> OTHER INFORMATION: synNAPS-1ABF

<400> SEQUENCE: 42

```
Gly Pro Trp Gly Glu Glu Lys Glu Val Asp Thr Ser Lys Ile Val Asp
1               5                   10                  15

Val Trp Arg Trp Gly Lys Tyr Val Asp Phe Phe Tyr Asp Asp Asn Gly
            20                  25                  30

Lys Val Gly Ile Gly Ser Val Thr
        35                  40
```

<210> SEQ ID NO 43
<211> LENGTH: 40
<212> TYPE: PRT
<213> ORGANISM: Artificial Sequence
<220> FEATURE:

<223> OTHER INFORMATION: synNAPS-2ABF

<400> SEQUENCE: 43

Lys Tyr Lys Gly Glu Glu Lys Glu Val Asp Thr Ser Lys Ile Val Trp
1               5                   10                  15

Ile Gly Arg Phe Gly Lys Ser Val Tyr Phe Arg Tyr Asp Asp Asn Gly
            20                  25                  30

Lys Thr Gly Ala Gly Arg Val Tyr
        35                  40

<210> SEQ ID NO 44
<211> LENGTH: 40
<212> TYPE: PRT
<213> ORGANISM: Artificial Sequence
<220> FEATURE:
<223> OTHER INFORMATION: synNAPS-3ABF

<400> SEQUENCE: 44

Arg Trp Gly Gly Glu Glu Lys Glu Val Asp Thr Ser Lys Ile Trp Tyr
1               5                   10                  15

Val Ala Arg Val Gly Lys Trp Val Leu Phe Gly Tyr Asp Asp Asn Gly
            20                  25                  30

Lys Arg Gly Ala Gly Arg Val Arg
        35                  40

<210> SEQ ID NO 45
<211> LENGTH: 40
<212> TYPE: PRT
<213> ORGANISM: Artificial Sequence
<220> FEATURE:
<223> OTHER INFORMATION: synNAPS-4ABF

<400> SEQUENCE: 45

Lys Tyr Lys Gly Glu Glu Lys Glu Val Asp Thr Ser Lys Ile Ser Tyr
1               5                   10                  15

Val Gln Arg Ala Gly Lys Ser Val Tyr Phe Asn Tyr Asp Asp Asn Gly
            20                  25                  30

Lys Thr Gly Gly Gly Arg Val Phe
        35                  40

<210> SEQ ID NO 46
<211> LENGTH: 40
<212> TYPE: PRT
<213> ORGANISM: Artificial Sequence
<220> FEATURE:
<223> OTHER INFORMATION: synNAPS-5ABF

<400> SEQUENCE: 46

Val Leu Lys Gly Glu Glu Lys Glu Val Asp Thr Ser Lys Ile Thr Tyr
1               5                   10                  15

Val Ala Arg Tyr Gly Lys Phe Val Gln Phe Asp Tyr Asp Asp Asn Gly
            20                  25                  30

Lys Phe Gly Ala Gly Val Val Leu
        35                  40

<210> SEQ ID NO 47
<211> LENGTH: 40
<212> TYPE: PRT
<213> ORGANISM: Artificial Sequence
<220> FEATURE:
<223> OTHER INFORMATION: synNAPS-6ABF

<400> SEQUENCE: 47

Met Arg Trp Gly Glu Glu Lys Glu Val Asp Thr Ser Lys Ile Thr Tyr
1               5                   10                  15

Val Thr Arg Trp Gly Lys Thr Val Ile Phe Tyr Tyr Asp Asp Asn Gly
            20                  25                  30

Lys Lys Gly His Gly Ser Val Leu
        35                  40

<210> SEQ ID NO 48
<211> LENGTH: 40
<212> TYPE: PRT
<213> ORGANISM: Artificial Sequence
<220> FEATURE:
<223> OTHER INFORMATION: synNAPS-7ABF

<400> SEQUENCE: 48

Lys Val His Gly Lys Glu Lys Glu Val Asp Thr Ser Lys Ile Leu Ala
1               5                   10                  15

Val Ala Arg Trp Gly Lys Ala Val Ile Phe Ala Tyr Asp Asp Asn Gly
            20                  25                  30

Lys His Gly Arg Gly Gln Val Ser
        35                  40

<210> SEQ ID NO 49
<211> LENGTH: 40
<212> TYPE: PRT
<213> ORGANISM: Artificial Sequence
<220> FEATURE:
<223> OTHER INFORMATION: synNAPS-8ABF

<400> SEQUENCE: 49

His Gly Arg Gly Glu Glu Lys Glu Val Asp Thr Ser Lys Ile Phe Trp
1               5                   10                  15

Val Tyr Arg Asp Gly Lys Arg Val Leu Phe Arg Tyr Asp Asp Asn Gly
            20                  25                  30

Lys Arg Gly Phe Gly Ser Val Pro
        35                  40

<210> SEQ ID NO 50
<211> LENGTH: 40
<212> TYPE: PRT
<213> ORGANISM: Artificial Sequence
<220> FEATURE:
<223> OTHER INFORMATION: synNAPS-9ABF

<400> SEQUENCE: 50

Ala Gln Gly Gly Glu Glu Lys Glu Val Asp Thr Ser Lys Ile Tyr Arg
1               5                   10                  15

Val Pro Arg His Gly Lys Ile Val Phe Phe Met Tyr Asp Asp Asn Gly
            20                  25                  30

Lys Gly Gly Phe Gly His Val Thr
        35                  40

<210> SEQ ID NO 51
<211> LENGTH: 40
<212> TYPE: PRT
<213> ORGANISM: Artificial Sequence
<220> FEATURE:
<223> OTHER INFORMATION: synNAPS-10ABF

<400> SEQUENCE: 51

Leu Met Lys Gly Glu Glu Lys Glu Val Asp Thr Ser Lys Ile Lys Trp
1               5                   10                  15

-continued

Val Asn Arg His Gly Lys Tyr Val Ala Phe Tyr Tyr Asp Asp Asn Gly
            20                  25                  30

Lys Thr Gly Gly Gly Glu Val Arg
        35                  40

<210> SEQ ID NO 52
<211> LENGTH: 40
<212> TYPE: PRT
<213> ORGANISM: Artificial Sequence
<220> FEATURE:
<223> OTHER INFORMATION: synNAPS-11ABF

<400> SEQUENCE: 52

Gly Leu Gly Gly Glu Glu Lys Glu Val Asp Thr Ser Lys Ile Arg Arg
1               5                   10                  15

Val Leu Arg Leu Gly Lys Leu Val Ser Phe Thr Tyr Asp Asp Asn Gly
            20                  25                  30

Lys Ile Gly Leu Gly Asp Val His
        35                  40

<210> SEQ ID NO 53
<211> LENGTH: 40
<212> TYPE: PRT
<213> ORGANISM: Artificial Sequence
<220> FEATURE:
<223> OTHER INFORMATION: synNAPS-12ABF

<400> SEQUENCE: 53

Lys Leu Thr Gly Glu Glu Lys Glu Val Asp Thr Ser Lys Ile Gln Trp
1               5                   10                  15

Val Ala Arg Phe Gly Lys Phe Val Asp Phe Leu Tyr Asp Asp Asn Gly
            20                  25                  30

Lys Thr Gly Trp Gly Trp Val Tyr
        35                  40

<210> SEQ ID NO 54
<211> LENGTH: 40
<212> TYPE: PRT
<213> ORGANISM: Artificial Sequence
<220> FEATURE:
<223> OTHER INFORMATION: synNAPS-13ABF

<400> SEQUENCE: 54

Lys Arg Trp Gly Glu Glu Lys Glu Val Asp Thr Ser Lys Ile Leu His
1               5                   10                  15

Val Leu Arg Val Gly Lys Tyr Val Arg Phe Ser Tyr Asp Asp Asn Gly
            20                  25                  30

Lys Leu Gly Ala Gly Tyr Val Thr
        35                  40

<210> SEQ ID NO 55
<211> LENGTH: 40
<212> TYPE: PRT
<213> ORGANISM: Artificial Sequence
<220> FEATURE:
<223> OTHER INFORMATION: synNAPS-14ABF

<400> SEQUENCE: 55

Lys Tyr Lys Gly Glu Glu Lys Glu Val Asp Thr Ser Lys Ile Ile Phe
1               5                   10                  15

Val Tyr Arg Phe Gly Lys Phe Val Met Phe Ile Tyr Asp Asp Asn Gly
            20                  25                  30

```
Lys Thr Gly His Gly Asp Val Arg
        35                  40

<210> SEQ ID NO 56
<211> LENGTH: 66
<212> TYPE: PRT
<213> ORGANISM: Artificial Sequence
<220> FEATURE:
<223> OTHER INFORMATION: synNAPS variant

<400> SEQUENCE: 56

Met Val Lys Val Lys Phe Ala Tyr Lys Gly Glu Glu Lys Glu Val Asp
1               5                   10                  15

Thr Ser Lys Ile Val Trp Ile Gly Arg Phe Gly Lys Ser Val Tyr Phe
            20                  25                  30

Arg Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 57
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 57

Met Val Lys Val Lys Phe Lys Ala Lys Gly Glu Glu Lys Glu Val Asp
1               5                   10                  15

Thr Ser Lys Ile Val Trp Ile Gly Arg Phe Gly Lys Ser Val Tyr Phe
            20                  25                  30

Arg Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 58
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 58

Met Val Lys Val Lys Phe Lys Tyr Ala Gly Glu Glu Lys Glu Val Asp
1               5                   10                  15

Thr Ser Lys Ile Val Trp Ile Gly Arg Phe Gly Lys Ser Val Tyr Phe
            20                  25                  30

Arg Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65
```

<210> SEQ ID NO 59
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 59

Met Val Lys Val Lys Phe Lys Tyr Lys Gly Glu Glu Lys Glu Val Asp
1               5                   10                  15

Thr Ser Lys Ile Ala Trp Ile Gly Arg Phe Gly Lys Ser Val Tyr Phe
            20                  25                  30

Arg Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 60
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 60

Met Val Lys Val Lys Phe Lys Tyr Lys Gly Glu Glu Lys Glu Val Asp
1               5                   10                  15

Thr Ser Lys Ile Val Ala Ile Gly Arg Phe Gly Lys Ser Val Tyr Phe
            20                  25                  30

Arg Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 61
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 61

Met Val Lys Val Lys Phe Lys Tyr Lys Gly Glu Glu Lys Glu Val Asp
1               5                   10                  15

Thr Ser Lys Ile Val Trp Ala Gly Arg Phe Gly Lys Ser Val Tyr Phe
            20                  25                  30

Arg Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 62
<211> LENGTH: 66
<212> TYPE: PRT

<213> ORGANISM: Artificial Sequence
<220> FEATURE:
<223> OTHER INFORMATION: synNAPS2 variant

<400> SEQUENCE: 62

```
Met Val Lys Val Lys Phe Lys Tyr Lys Gly Glu Glu Lys Glu Val Asp
1               5                   10                  15
Thr Ser Lys Ile Val Trp Ile Ala Arg Phe Gly Lys Ser Val Tyr Phe
            20                  25                  30
Arg Tyr Asp Asp Asn Gly Lys Thr Gly Ala Gly Arg Val Tyr Glu Lys
        35                  40                  45
Asp Ala Pro Lys Glu Leu Leu Asp Met Leu Ala Arg Ala Glu Arg Glu
    50                  55                  60
Lys Lys
65
```

<210> SEQ ID NO 63
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 63

```
Met Val Lys Val Lys Phe Lys Tyr Lys Gly Glu Glu Lys Glu Val Asp
1               5                   10                  15
Thr Ser Lys Ile Val Trp Ile Gly Arg Ala Gly Lys Ser Val Tyr Phe
            20                  25                  30
Arg Tyr Asp Asp Asn Gly Lys Thr Gly Ala Gly Arg Val Tyr Glu Lys
        35                  40                  45
Asp Ala Pro Lys Glu Leu Leu Asp Met Leu Ala Arg Ala Glu Arg Glu
    50                  55                  60
Lys Lys
65
```

<210> SEQ ID NO 64
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 64

```
Met Val Lys Val Lys Phe Lys Tyr Lys Gly Glu Glu Lys Glu Val Asp
1               5                   10                  15
Thr Ser Lys Ile Val Trp Ile Gly Arg Phe Gly Lys Ala Val Tyr Phe
            20                  25                  30
Arg Tyr Asp Asp Asn Gly Lys Thr Gly Ala Gly Arg Val Tyr Glu Lys
        35                  40                  45
Asp Ala Pro Lys Glu Leu Leu Asp Met Leu Ala Arg Ala Glu Arg Glu
    50                  55                  60
Lys Lys
65
```

<210> SEQ ID NO 65
<211> LENGTH: 66
<212> TYPE: PRT
<213> ORGANISM: Artificial Sequence
<220> FEATURE:
<223> OTHER INFORMATION: synNAPS2 variant

```
<400> SEQUENCE: 65

Met Val Lys Val Lys Phe Lys Tyr Lys Gly Glu Glu Lys Glu Val Asp
1               5                   10                  15

Thr Ser Lys Ile Val Trp Ile Gly Arg Phe Gly Lys Ser Val Ala Phe
            20                  25                  30

Arg Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 66
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 66

Met Val Lys Val Lys Phe Lys Tyr Lys Gly Glu Glu Lys Glu Val Asp
1               5                   10                  15

Thr Ser Lys Ile Val Trp Ile Gly Arg Phe Gly Lys Ser Val Tyr Phe
            20                  25                  30

Ala Tyr Asp Asp Asn Gly Lys Thr Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 67
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 67

Met Val Lys Val Lys Phe Lys Tyr Lys Gly Glu Glu Lys Glu Val Asp
1               5                   10                  15

Thr Ser Lys Ile Val Trp Ile Gly Arg Phe Gly Lys Ser Val Tyr Phe
            20                  25                  30

Arg Tyr Asp Asp Asn Gly Lys Ala Gly Ala Gly Arg Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 68
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 68

Met Val Lys Val Lys Phe Lys Tyr Lys Gly Glu Glu Lys Glu Val Asp
1               5                   10                  15
```

```
Thr Ser Lys Ile Val Trp Ile Gly Arg Phe Gly Lys Ser Val Tyr Phe
            20                  25                  30

Arg Tyr Asp Asp Asn Gly Lys Thr Gly Ala Gly Ala Val Tyr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 69
<211> LENGTH: 66
<212> TYPE: PRT
<213> ORGANISM: Artificial Sequence
<220> FEATURE:
<223> OTHER INFORMATION: synNAPS2 variant

<400> SEQUENCE: 69

Met Val Lys Val Lys Phe Lys Tyr Lys Gly Glu Glu Lys Glu Val Asp
1               5                   10                  15

Thr Ser Lys Ile Val Trp Ile Gly Arg Phe Gly Lys Ser Val Tyr Phe
            20                  25                  30

Arg Tyr Asp Asp Asn Gly Lys Thr Gly Ala Gly Arg Val Ala Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 70
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 70

Met Val Lys Val Lys Phe Ala Ala Gly Gly Glu Glu Lys Glu Val Asp
1               5                   10                  15

Thr Ser Lys Ile Tyr Arg Val Pro Arg His Gly Lys Ile Val Phe Phe
            20                  25                  30

Met Tyr Asp Asp Asn Gly Lys Gly Gly Phe Gly His Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 71
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 71

Met Val Lys Val Lys Phe Ala Gln Ala Gly Glu Glu Lys Glu Val Asp
1               5                   10                  15

Thr Ser Lys Ile Tyr Arg Val Pro Arg His Gly Lys Ile Val Phe Phe
            20                  25                  30
```

Met Tyr Asp Asp Asn Gly Lys Gly Gly Phe Gly His Val Thr Glu Lys
                35                  40                  45

Asp Ala Pro Lys Glu Leu Leu Asp Met Leu Ala Arg Ala Glu Arg Glu
    50                  55                  60

Lys Lys
65

<210> SEQ ID NO 72
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 72

Met Val Lys Val Lys Phe Ala Gln Gly Gly Glu Glu Lys Glu Val Asp
1               5                   10                  15

Thr Ser Lys Ile Ala Arg Val Pro Arg His Gly Lys Ile Val Phe Phe
                20                  25                  30

Met Tyr Asp Asp Asn Gly Lys Gly Gly Phe Gly His Val Thr Glu Lys
                35                  40                  45

Asp Ala Pro Lys Glu Leu Leu Asp Met Leu Ala Arg Ala Glu Arg Glu
    50                  55                  60

Lys Lys
65

<210> SEQ ID NO 73
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 73

Met Val Lys Val Lys Phe Ala Gln Gly Gly Glu Glu Lys Glu Val Asp
1               5                   10                  15

Thr Ser Lys Ile Tyr Ala Val Pro Arg His Gly Lys Ile Val Phe Phe
                20                  25                  30

Met Tyr Asp Asp Asn Gly Lys Gly Gly Phe Gly His Val Thr Glu Lys
                35                  40                  45

Asp Ala Pro Lys Glu Leu Leu Asp Met Leu Ala Arg Ala Glu Arg Glu
    50                  55                  60

Lys Lys
65

<210> SEQ ID NO 74
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 74

Met Val Lys Val Lys Phe Ala Gln Gly Gly Glu Glu Lys Glu Val Asp
1               5                   10                  15

Thr Ser Lys Ile Tyr Arg Val Ala Arg His Gly Lys Ile Val Phe Phe
                20                  25                  30

Met Tyr Asp Asp Asn Gly Lys Gly Gly Phe Gly His Val Thr Glu Lys
                35                  40                  45

Asp Ala Pro Lys Glu Leu Leu Asp Met Leu Ala Arg Ala Glu Arg Glu

Lys Lys
65

<210> SEQ ID NO 75
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 75

Met Val Lys Val Lys Phe Ala Gln Gly Gly Glu Glu Lys Glu Val Asp
1               5                   10                  15

Thr Ser Lys Ile Tyr Arg Val Pro Arg Ala Gly Lys Ile Val Phe Phe
            20                  25                  30

Met Tyr Asp Asp Asn Gly Lys Gly Gly Phe Gly His Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 76
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 76

Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ala Val Phe Phe
            20                  25                  30

Met Tyr Asp Asp Asn Gly Lys Gly Gly Phe Gly His Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 77
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 77

Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ile Val Ala Phe
            20                  25                  30

Met Tyr Asp Asp Asn Gly Lys Gly Gly Phe Gly His Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 78
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 78

```
Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ile Val Phe Phe
            20                  25                  30

Ala Tyr Asp Asp Asn Gly Lys Gly Gly Phe Gly His Val Thr Glu Lys
        35                  40                  45

Asp Ala Pro Lys Glu Leu Leu Asp Met Leu Ala Arg Ala Glu Arg Glu
    50                  55                  60

Lys Lys
65
```

<210> SEQ ID NO 79
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 79

```
Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ile Val Phe Phe
            20                  25                  30

Met Tyr Asp Asp Asn Gly Lys Ala Gly Phe Gly His Val Thr Glu Lys
        35                  40                  45

Asp Ala Pro Lys Glu Leu Leu Asp Met Leu Ala Arg Ala Glu Arg Glu
    50                  55                  60

Lys Lys
65
```

<210> SEQ ID NO 80
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 80

```
Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ile Val Phe Phe
            20                  25                  30

Met Tyr Asp Asp Asn Gly Lys Gly Gly Ala Gly His Val Thr Glu Lys
        35                  40                  45

Asp Ala Pro Lys Glu Leu Leu Asp Met Leu Ala Arg Ala Glu Arg Glu
    50                  55                  60

Lys Lys
65
```

<210> SEQ ID NO 81
<211> LENGTH: 66

<212> TYPE: PRT
<213> ORGANISM: Artificial Sequence
<220> FEATURE:
<223> OTHER INFORMATION: synNAPS9 variant

<400> SEQUENCE: 81

Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ile Val Phe Phe
            20                  25                  30

Met Tyr Asp Asp Asn Gly Lys Gly Gly Phe Gly Ala Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 82
<211> LENGTH: 66
<212> TYPE: PRT
<213> ORGANISM: Artificial Sequence
<220> FEATURE:
<223> OTHER INFORMATION: synNAPS9 variant

<400> SEQUENCE: 82

Met Val Lys Val Lys Phe Ala Gln Gly Gly Glu Glu Lys Glu Val Asp
1               5                   10                  15

Thr Ser Lys Ile Tyr Arg Val Pro Arg His Gly Lys Ile Val Phe Phe
            20                  25                  30

Met Tyr Asp Asp Asn Gly Lys Gly Gly Phe Gly His Val Ala Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 83
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 83

Met Val Lys Val Lys Phe Ala Arg Trp Gly Glu Glu Lys Glu Val Asp
1               5                   10                  15

Thr Ser Lys Ile Leu His Val Leu Arg Val Gly Lys Tyr Val Arg Phe
            20                  25                  30

Ser Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 84
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 84

Met Val Lys Val Lys Phe Lys Ala Trp Gly Glu Glu Lys Glu Val Asp
1               5                   10                  15

Thr Ser Lys Ile Leu His Val Leu Arg Val Gly Lys Tyr Val Arg Phe
            20                  25                  30

Ser Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 85
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 85

Met Val Lys Val Lys Phe Lys Arg Ala Gly Glu Glu Lys Glu Val Asp
1               5                   10                  15

Thr Ser Lys Ile Leu His Val Leu Arg Val Gly Lys Tyr Val Arg Phe
            20                  25                  30

Ser Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 86
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 86

Met Val Lys Val Lys Phe Lys Arg Trp Gly Glu Glu Lys Glu Val Asp
1               5                   10                  15

Thr Ser Lys Ile Ala His Val Leu Arg Val Gly Lys Tyr Val Arg Phe
            20                  25                  30

Ser Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 87
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 87

Met Val Lys Val Lys Phe Lys Arg Trp Gly Glu Glu Lys Glu Val Asp

```
1               5                   10                  15
Thr Ser Lys Ile Leu Ala Val Leu Arg Val Gly Lys Tyr Val Arg Phe
            20                  25                  30

Ser Tyr Asp Asp Asn Gly Lys Leu Gly Ala Gly Tyr Val Thr Glu Lys
                35                  40                  45

Asp Ala Pro Lys Glu Leu Leu Asp Met Leu Ala Arg Ala Glu Arg Glu
        50                  55                  60

Lys Lys
65
```

<210> SEQ ID NO 88
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 88

```
Met Val Lys Val Lys Phe Lys Arg Trp Gly Glu Glu Lys Glu Val Asp
1               5                   10                  15

Thr Ser Lys Ile Leu His Val Ala Arg Val Gly Lys Tyr Val Arg Phe
            20                  25                  30

Ser Tyr Asp Asp Asn Gly Lys Leu Gly Ala Gly Tyr Val Thr Glu Lys
                35                  40                  45

Asp Ala Pro Lys Glu Leu Leu Asp Met Leu Ala Arg Ala Glu Arg Glu
        50                  55                  60

Lys Lys
65
```

<210> SEQ ID NO 89
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 89

```
Met Val Lys Val Lys Phe Lys Arg Trp Gly Glu Glu Lys Glu Val Asp
1               5                   10                  15

Thr Ser Lys Ile Leu His Val Leu Arg Ala Gly Lys Tyr Val Arg Phe
            20                  25                  30

Ser Tyr Asp Asp Asn Gly Lys Leu Gly Ala Gly Tyr Val Thr Glu Lys
                35                  40                  45

Asp Ala Pro Lys Glu Leu Leu Asp Met Leu Ala Arg Ala Glu Arg Glu
        50                  55                  60

Lys Lys
65
```

<210> SEQ ID NO 90
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 90

```
Met Val Lys Val Lys Phe Lys Arg Trp Gly Glu Glu Lys Glu Val Asp
1               5                   10                  15

Thr Ser Lys Ile Leu His Val Leu Arg Val Gly Lys Ala Val Arg Phe
            20                  25                  30
```

```
Ser Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 91
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 91

Met Val Lys Val Lys Phe Lys Arg Trp Gly Glu Glu Lys Glu Val Asp
1               5                   10                  15

Thr Ser Lys Ile Leu His Val Leu Arg Val Gly Lys Tyr Val Ala Phe
            20                  25                  30

Ser Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 92
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 92

Met Val Lys Val Lys Phe Lys Arg Trp Gly Glu Glu Lys Glu Val Asp
1               5                   10                  15

Thr Ser Lys Ile Leu His Val Leu Arg Val Gly Lys Tyr Val Arg Phe
            20                  25                  30

Ala Tyr Asp Asp Asn Gly Lys Leu Gly Ala Gly Tyr Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 93
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 93

Met Val Lys Val Lys Phe Lys Arg Trp Gly Glu Glu Lys Glu Val Asp
1               5                   10                  15

Thr Ser Lys Ile Leu His Val Leu Arg Val Gly Lys Tyr Val Arg Phe
            20                  25                  30

Ser Tyr Asp Asp Asn Gly Lys Ala Gly Ala Gly Tyr Val Thr Glu Lys
        35                  40                  45
```

Asp Ala Pro Lys Glu Leu Leu Asp Met Leu Ala Arg Ala Glu Arg Glu
        50                  55                  60

Lys Lys
65

<210> SEQ ID NO 94
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 94

Met Val Lys Val Lys Phe Lys Arg Trp Gly Glu Glu Lys Glu Val Asp
1               5                   10                  15

Thr Ser Lys Ile Leu His Val Leu Arg Val Gly Lys Tyr Val Arg Phe
            20                  25                  30

Ser Tyr Asp Asp Asn Gly Lys Leu Gly Ala Gly Ala Val Thr Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 95
<211> LENGTH: 66
<212> TYPE: PRT
<213> ORGANISM: Artificial Sequence
<220> FEATURE:
<223> OTHER INFORMATION: synNAPS13 variant

<400> SEQUENCE: 95

Met Val Lys Val Lys Phe Lys Arg Trp Gly Glu Glu Lys Glu Val Asp
1               5                   10                  15

Thr Ser Lys Ile Leu His Val Leu Arg Val Gly Lys Tyr Val Arg Phe
            20                  25                  30

Ser Tyr Asp Asp Asn Gly Lys Leu Gly Ala Gly Tyr Val Ala Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 96
<211> LENGTH: 40
<212> TYPE: PRT
<213> ORGANISM: Artificial Sequence
<220> FEATURE:
<223> OTHER INFORMATION: synNAPS2 consensus binding domain
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

```
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 96

Xaa Xaa Xaa Gly Glu Glu Lys Glu Val Asp Thr Ser Lys Ile Xaa Trp
1               5                   10                  15

Xaa Xaa Arg Xaa Gly Lys Ser Val Tyr Phe Xaa Tyr Asp Asp Asn Gly
            20                  25                  30

Lys Xaa Gly Ala Gly Arg Val Xaa
        35                  40

<210> SEQ ID NO 97
<211> LENGTH: 40
<212> TYPE: PRT
<213> ORGANISM: Artificial Sequence
<220> FEATURE:
<223> OTHER INFORMATION: synNAPS9 consensus binding domain
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 97

Xaa Xaa Xaa Gly Glu Glu Lys Glu Val Asp Thr Ser Lys Ile Xaa Xaa
1               5                   10                  15

Val Xaa Arg Xaa Gly Lys Ile Val Xaa Phe Xaa Tyr Asp Asp Asn Gly
            20                  25                  30

Lys Xaa Gly Phe Gly Xaa Val Xaa
        35                  40
```

```
<210> SEQ ID NO 98
<211> LENGTH: 40
<212> TYPE: PRT
<213> ORGANISM: Artificial Sequence
<220> FEATURE:
<223> OTHER INFORMATION: synNAPS13 consensus binding domain
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 98

Xaa Xaa Xaa Gly Glu Glu Lys Glu Val Asp Thr Ser Lys Ile Xaa His
1               5                   10                  15

Val Xaa Arg Xaa Gly Lys Xaa Val Arg Phe Xaa Tyr Asp Asp Asn Gly
            20                  25                  30

Lys Leu Gly Xaa Gly Tyr Val Xaa
        35                  40
```

NON-ANTIBODY LIGANDS FOR DETECTING TARGET PROTEINS

This application is a § 371 of PCT/US2018/65440, filed, Dec. 13, 2018, and published Jun. 20, 2019 as WO2019/18721, which claims priority from U.S. Provisional Application No. 62/599,289, filed Dec. 15, 2017, both of which are incorporated herein by reference in their entirety.

FIELD OF THE INVENTION

The invention relates to synthetic non-antibody protein scaffolds that specifically bind to insecticidal proteins and are useful in differential detection or quantitation of target proteins of interest in complex mixtures. The invention further relates generally to diagnostic methods for reliably determining the presence and amount of certain target proteins of interest in a biological sample such as a transgenic plant sample containing a complex mixture of the target and non-target proteins, and to test kits providing the essential reagents for the diagnostic methods.

BACKGROUND

Transgenic crops consist of increasingly complex genetic modifications including multiple transgenes that confer different traits, also called "gene stacks" or "trait stacks." For example, many transgenic corn products currently on the market contain within the same plant multiple insecticidal proteins for controlling a broad spectrum of insect pests and multiple proteins that confer on the plant tolerance to a wide spectrum of chemical herbicides. Many of the transgenic proteins used to control insect pests, for example the crystal endotoxins from *Bacillus thuringiensis* (called Cry proteins) may be structurally closely related and have similar overall amino acid sequence identity or contain motifs or domains with significant identity to each other. In general, Cry proteins, for example, have three structural domains: the N-terminal domain I, from residues 1 to about 290, consists of 7 alpha helices, domain II, from about residues 291-500, contains three beta-sheets and the C-terminal domain III, from about residues 501-644, is a beta-sandwich. Most Cry proteins active against lepidopteran or coleopteran insects are formed in a crystalline matrix as 130-140 kDa or 60-70 kDa protoxins, respectively. In lepidopteran insects, the alkaline pH of the gut solubilizes the crystal and then gut proteases process the 130-140 kDa protoxin to toxic proteins of approximately 60-70 kDa. In coleopteran insects, the 60-70 kDa protoxins are processed to 55-67 kDa toxins. Examples of lepidopteran-active Cry proteins include Cry1A, Cry1B, Cry1C, Cry1D, Cry1E, Cry1F and Cry9. Examples of coleopteran-active Cry proteins include, Cry3A, Cry3B, Cry3C, Cry8, the binary Cry23-Cry37 and the binary Cry34-Cry35. Proteolytic processing of the Cry protein protoxin to an insecticidal toxin has been reported to proceed by removal of both N- and C-terminal amino acids with the exact location of processing being dependent on the specific Cry protein and the specific insect gut fluids involved (Ogiwara et al., 1992. J. Invert. Pathol. 60:121-126). This proteolytic activation of a Cry protoxin can play a significant role in determining its specificity Many successful attempts to create hybrid Cry proteins have been disclosed in the literature. For example, the silk moth (*Bombyx mori*) specificity domain from a Cry1Aa protein was moved to a Cry1Ac protein, thus imparting a new insecticidal activity to the resulting Cry1Aa-Cry1Ac chimeric protein (Ge et al. 1989, PNAS 86: 4037 4041). Thompson et al. 1996 and 1997 (U.S. Pat. Nos. 5,527,883 and 5,593,881) replaced the protoxin tail region of a wild-type Cry1F protein and Cry1C protein with the protoxin tail region of a Cry1Ab protein to make a Cry1F-Cry1Ab hybrid Cry protein and a Cry1C-Cry1Ab hybrid Cry protein, both having improved expression in certain expression host cells. Bosch et al. 1998 (U.S. Pat. No. 5,736,131), created new lepidopteran-active proteins by substituting domain III of a Cry1Ea protein and a Cry1Ab protein with domain III of Cry1Ca protein thus producing a Cry1E-Cry1C hybrid Cry protein called G27 and a Cry1Ab-Cry1C hybrid Cry protein called H04, both of which have a broader spectrum of lepidopteran activity than the wild-type Cry protein parent molecules. Malvar et al. 2001 (U.S. Pat. No. 6,242,241) combined domain I of a Cry1Ac protein with domains II and III and the protoxin tail of a Cry1F protein to create a Cry1Ac-Cry1F hybrid Cry protein with broader insecticidal activity than the parental wild-type Cry proteins. Bogdanova et al. 2011 (U.S. Pat. No. 8,034,997) combined domains I and II of a Cry1Ab protein with domain III of a Cry1Fa protein and added a Cry1Ac protein protoxin tail to create a new lepidopteran-active hybrid Cry protein called Cry1A.105. And, Hart et al. 2012 (U.S. Pat. No. 8,309,516) combined domains I and II of a modified Cry3A protein with domain III of a Cry1Ab protein and added a portion of a Cry1Ab protein protoxin tail to create a coleopteran-active hybrid Cry protein called FR8a (also called eCry3.1Ab). Most of the reported hybrid Cry proteins to date have used all or parts of the same classes of wild-type Cry proteins, such as Cry1Aa, Cry1Ab, Cry1Ac, Cry1C, Cry1F and Cry3A.

Several wild-type Cry proteins, for example Cry1Ab, Cry1Ac, Cry1C, Cry1F, Cry2A, Cry2Ba, Cry3A, Cry3B, Cry9C and Cry34-Cry35, as well as vegetative insecticidal proteins, such as Vip3A (See U.S. Pat. No. 5,877,012), have been expressed in transgenic crop plants, including corn, cotton, rice and soybean, some of which have been exploited commercially to control certain lepidopteran and coleopteran insect pests since as early as 1996. More recently, transgenic crop products, e.g. corn, containing engineered Cry proteins having one or more amino acids substituted, deleted or inserted, for example modified Cry3A (mCry3A; U.S. Pat. No. 7,230,167), and hybrid Cry proteins, for example, eCry3.1Ab and Cry1A.105 described above, have been introduced commercially.

The increasing use of recombinant DNA technology to produce transgenic plants for commercial and industrial use requires the development of diagnostic methods of analyzing transgenic plant lines. Such methods are needed to maintain transgenic plant varieties through successive generations of breeding, to monitor the presence of transgenic plants or plant parts in the environment or in biological samples derived from the transgenic plants, and to assist in the rapid creation and development of new transgenic plants with desirable or optimal phenotypes. Moreover, current guidelines for the safety assessment of transgenic plants from many countries' regulatory agencies requires characterization at the DNA and protein level to obtain and maintain regulatory approval. The increasing complexity of the genes and proteins stacked into a transgenic plant as described above make specific detection and quantitation of any one target protein within the complex mixture difficult, particularly when the stacked transgenic proteins are similar to each other, or similar to wild-type non-transgenic proteins in the environment, or similar to non-transgenic proteins endogenous to the transgenic plant.

Immunoassay is the current preferred method in the agricultural industry for detection and quantification of proteins introduced through genetic modification of plants. The crucial component of an immunoassay is an antibody with specificity for the target protein (antigen). Immunoassays can be highly specific and samples often need only a simple preparation before being analyzed. Moreover, immunoassays can be used qualitatively or quantitatively over a wide range of concentrations. Typically, immunoassays require separate tests for each protein of interest. The antibodies can be polyclonal, raised in animals, or monoclonal, produced by cell cultures. By their nature, a mixture of polyclonal antibodies will have multiple recognition epitopes, which can increase sensitivity, but it is also likely to reduce specificity, as the chances of sequence and structural homology with other proteins increases with the number of different antibody paratopes present. Monoclonal antibodies offer some advantages over polyclonal antibodies because they express uniform affinity and specificity against a single epitope or antigenic determinant and can be produced in vast quantities. However, there are intrinsic properties of all antibodies that limit their use for more demanding applications, such as differential detection and quantitation of single transgenic proteins in complex mixtures or similar transgenic or endogenous proteins. In addition, both polyclonal and monoclonal antibodies may require further purification steps to enhance the sensitivity and reduce backgrounds in assays.

Due to their limitations for use under certain conditions, an alternative to antibodies was developed using an evolved OB-fold protein (Pecorari and Alzari, 2016. U.S. Pat. No. 9,422,548). OB-fold proteins are any protein with an OB-fold topology as described by Murzin (1993, EMBO J. 12:861-867) and Arcus (2002, Curr. Opin. Struct. Biol. 12:794-801). For example, the OB-fold protein Sac7d, which is known to bind to DNA molecules in its native form, was evolved in vitro and shown by Pecorari and Alzari supra., to bind to proteins with high specificity and affinity Reengineering the natural binding site of Sac7d by randomization of the residues exposed to the solvent allows for the creation of libraries of so called Nanofitin® variants (Affilogic, Nantes, France) from the wild-type Sac7d proteins. These Nanofitin® variants have been shown to be useful as therapeutics.

Currently, making a valid identification of a transgenic plant product containing a transgenic protein or quantitating a transgenic protein in a commercial crop product depends on the accuracy of the immunoassay. Development of a successful immunoassay depends on certain characteristics of the antigen used for development of the antibody, i.e. size, hydrophobicity and the tertiary structure of the antigen and the quality and accuracy of the antibody. The specificity of antibodies must be checked carefully to elucidate any cross-reactivity with similar substances, which might cause false positive results. A current problem in the industry is that many of the antibodies in commercially available tests kits do not differentiate between similar transgenic proteins in various products or transgenic proteins from wild-type proteins, making differential product identification and quantitation difficult or impossible. For example, with many current commercial transgenic crop products using one or more of the same wild-type Cry proteins, for example Cry1Ab, Cry1Ac, Cry1F and Cry3, and with the introduction of crops expressing hybrid Cry proteins made of whole or parts of the same wild-type Cry proteins that are already in transgenic crop products, there is a continuing need to develop new and improved diagnostic methods to be able to distinguish wild-type Cry proteins from each other and from a hybrid Cry protein containing all or portions of that same wild-type Cry protein when they are together in complex biological samples, such as samples from transgenic plants, transgenic plant parts or transgenic microorganisms. Although non-antibody protein scaffolds show promise as ligands for use in biomedical therapeutics, it is not clear whether they can have functional utility in aiding to differentially detect highly similar transgenic insecticidal proteins in such a complex biological matrix as a transgenic plant or a sample from a transgenic plant.

SUMMARY OF THE DISCLOSURE

The present invention addresses the need for new and improved diagnostic methods by providing compositions useful in specific detection and differentiation of transgenic proteins. More particularly, the invention provides compositions, methods, assays and kits to specifically detect and differentiate transgenic wild-type insecticidal proteins from each other and from engineered hybrid proteins comprising all or part of a wild-type protein amino acid sequence in complex biological samples comprising both the wild-type protein and the hybrid protein, such as in transgenic plants, transgenic plant parts, or transgenic bacteria.

According to some aspects, the invention provides a synthetic non-antibody protein scaffold (synNAPS), or an antigen-binding fragment thereof, that binds to an insecticidal protein. Such synNAPS are useful for differential and specific detection or quantitation of a target transgenic insecticidal protein when the target protein is in the presence of one or more non-target transgenic insecticidal proteins.

In other aspects, the invention provides a synthetic non-antibody protein scaffold (synNAPS), or an antigen-binding fragment thereof, having a differential binding affinity to a target transgenic insecticidal protein when said target protein is in the presence of one or more non-target transgenic insecticidal proteins, wherein the target protein a) has at least 70% to at least 95% sequence identity across its entire length to one or more of the non-target proteins; or b) comprises a region that has at least 25% to at least 95% sequence identity to a region of one or more of the non-target proteins.

In other aspects, a synNAPS of the invention binds to or differentially detects or quantitates an insecticidal protein having an amino acid sequence that comprises any of SEQ ID NOs:1-7. In other aspects, the synNAPS has an amino acid sequence that comprises any of SEQ ID NOs:10-17, 19, 21, 24-31, 33 or 35.

In still other aspects of the invention, an amino acid sequence of a synNAPS of the invention has from at least 80% to at least 99% sequence identity to SEQ ID NO:10, SEQ ID NO:17 or SEQ ID NO:21 and wherein the amino acid sequence that has from at least 80% to at least 99% sequence identity to (a) SEQ ID NO:10 has a Tro (W) at a position corresponding to or at position 22 of SEQ ID NO:10, a Ser (S) at a position corresponding to or at position 29 of SEQ ID NO:10, a Tyr (Y) at a position corresponding to or at position 31 of SEQ ID NO:10 and a Arg (R) at a position corresponding to or at position 44 of SEQ ID NO:10; or (b) SEQ ID NO:17 has an Ile (I) at a position corresponding to or at position 29 of SEQ ID NO:17 and a Phe (F) at a position corresponding to or at position 42 of SEQ ID NO:17; or (c) SEQ ID NO:21 has a His (H) at a position corresponding to or at position 22 of SEQ ID NO:21, a Arg (R) at a position corresponding to or at position 31 of SEQ ID NO:21, a Leu (L) at a position corresponding to or at a position corresponding to or at position 40 of SEQ ID NO:21 and a Tyr (Y) at a position corresponding to or at position 44 of SEQ ID NO:21. In further aspects, the synNAPS has an amino acid sequence that comprises any of SEQ ID NOs:56-59, 61-63, 66, 67, 69-75, 77-79, 81-86, 88-90, 92 or 95.

In some aspects, the invention provides an antigen-binding fragment of a synNAPS of the invention. In other aspects, the antigen-binding fragment comprises at least about 14 to at least about 65 amino acids of any of SEQ ID NOs: 9-36. In other aspects, the antigen-binding fragment comprises any of SEQ ID NOs:96-98. In still other aspects, an antigen-binding fragment of a synNAPS of the invention comprises any of SEQ ID NOs:42-55.

In certain embodiments of the above described aspects of the invention, the target protein is a Cry1A protein, a mCry3A protein, an eCry3.1Ab protein or a hybrid Cry protein comprising domain I and domain II of a Cry1Ab protein.

In other embodiments of the above described aspects, the one or more non-target proteins are selected from the group consisting of a Cry1A protein, a Cry1B protein, a Cry1F protein Cry1I protein, a Cry1J protein, a hybrid Cry protein comprising domain I and domain II of a Cry1Ab protein, a hybrid Cry protein comprising domain III of a Cry1F protein, a modified Cry3A protein, a hybrid Cry3 protein comprising domain III of a Cry1Ab protein, and a Vip3 protein.

In other embodiments of the above described aspects of the invention, the target protein is a Cry1A protein, a mCry3A protein, an eCry3.1Ab protein or a hybrid Cry protein comprising domain I and domain II of a Cry1Ab protein and the one or more non-target proteins are selected from the group consisting of a Cry1A protein, a Cry1B protein, a Cry1F protein Cry1I protein, a Cry1J protein, a hybrid Cry protein comprising domain I and domain II of a Cry1Ab protein, a hybrid Cry protein comprising domain III of a Cry1F protein, a modified Cry3A protein, a hybrid Cry3 protein comprising domain III of a Cry1Ab protein, and a Vip3 protein. In some embodiments, the Cry1A protein is a Cry1Aa, a Cry1Ab or a Cry1Ai. In other embodiments the hybrid Cry protein is a Cry1Ab.1Ca protein or a Cry1A.105 protein.

In still other embodiments of the above described aspects, the target protein is a) a Cry1Ab and the non-target proteins include a mCry3A or an eCry3.1Ab; or b) is an mCry3A and the non-target proteins include a Cry1Ab or an eCry3.1Ab; or c) is an eCry3.1Ab and the non-target proteins include a Cry1Ab or an mCry3A; or d) is a Cry1Ab or a Cry1Ab.1Ca and the non-target proteins include a Cry1Aa or a Cry1Ai; or e) is a Cry1Ab or a Cry1Ai protein and the non-target proteins include a Cry1Aa or a Cry1Ab.1C; or f) is a Cry1Ab, a Cry1Ai or a Cry1Ab.Cry1C protein and the non-target protein is a Cry1Aa; or g) is a Cry1Ab protein or a Cry1Ab.Cry1C protein and the non-target proteins include a Cry1Aa or a Cry1Ai protein; or h) is a Cry1Aa or a Cry1Ai protein and the non-target proteins include a Cry1Ab protein or a Cry1Ab.1Ca protein.

In still other embodiments of the above described aspects of the invention, wherein the Cry1Ab protein comprises an amino acid sequence represented by SEQ ID NO:1, the mCry3A protein comprises an amino acid sequence represented by SEQ ID NO:2, the eCry3.1Ab protein comprises an amino acid sequence represented by SEQ ID NO:3, the Cry1Aa protein comprises an amino acid sequence represented by SEQ ID NO:4, the Cry1Ai protein comprises an amino acid sequence represented by SEQ ID NO:5, the Cry1Ab.1Ca protein comprises an amino acid sequence represented by SEQ ID NO:6 or the Cry1A.105 protein comprises an amino acid sequence represented by SEQ ID NO:7.

In another embodiment of the above described aspects, the synNAPS that binds specifically to Cry1Ab in the presence of mCry3A or eCry3.1Ab comprises SEQ ID NO:10 SEQ ID NO:11, SEQ ID NO:12 or SEQ ID NO:13. In another embodiment, the synNAPS that binds specifically to the mCry3A protein in the presence of Cry1Ab and eCry3.1Ab comprises SEQ ID NO:14, SEQ ID NO:15, SEQ ID NO:16 or SEQ ID NO:17. In another embodiment, the synNAPS that binds specifically to eCry3.1Ab in the presence of Cry1Ab and mCry3A comprises SEQ ID NO:21. In another embodiment, the synNAPS that binds to Cry1Ab or Cry1Ab.1Ca in the presence of Cry1Aa or Cry1Ai comprises SEQ ID NO:13. In another embodiment, the synNAPS that binds to eCry3.1Ab or mCry3A or Cry1Ai or Cry1Aa in the presence of Cry1Ab comprises SEQ ID NO:19.

In other embodiments of the above described aspects, the target protein and the non-target protein are in a biological sample from a transgenic plant or a transgenic microorganism. In one aspect of this embodiment, the transgenic plant is a corn plant, a soybean plant, a cotton plant, a canola plant, a wheat plant or a rice plant. In another aspect, the transgenic microorganism is a bacteria, yeast or virus. In still another aspect, the transgenic bacteria is *E. coli, Psuedomonas* sp. or *Bacillus* sp.

In another aspect, the invention provides a nucleic acid molecule encoding a synNAPS of the invention. In some embodiments of this aspect, the invention further provides a transgenic organism comprising the nucleic acid molecule. In some embodiments, the transgenic organism is a transgenic plant or a transgenic microorganism. In other embodiments, the transgenic plant is a corn plant, a soybean plant, a cotton plant, a canola plant, a wheat plant or a rice plant. In still other embodiments of this aspect, the microorganism is a bacteria, yeast or virus. In other embodiments, the bacteria is *E. coli, Pseudomonas* sp. or *Bacillus* sp.

In another aspect, the invention provides a composition comprising a first synNAPS of the invention and a second ligand, wherein the synNAPS and the second ligand function together in an immunoassay of a biological sample comprising a target protein and a non-target protein differentially detect or quantitate the target protein. In other aspects, the non-target protein comprises an amino acid sequence that has at least a contiguous 27% of the target protein's amino acid sequence.

In another aspect, the invention provides a diagnostic kit for differentially detecting a target insecticidal protein in a complex biological matrix which comprises the target insecticidal protein and a non-target insecticidal protein, wherein the kit comprises a first synNAPS of the invention and a second ligand different from the first synNAPS that function together in an immunoassay to differentially detect or quantitate the target insecticidal protein. In other aspects, the non-target protein comprises an amino acid sequence that has at least a contiguous 27% of the target protein's amino acid sequence.

According to other aspects of the invention there is provided methods for differentially detecting or quantitating a target insecticidal protein in a biological sample comprising the target protein and a non-target insecticidal protein, the method comprising (a) obtaining a biological sample comprising the target insecticidal protein and the non-target insecticidal protein; (b) performing an immunoassay on the biological sample, wherein the immunoassay comprises use of a first synNAPS of the invention and a second ligand different from the first synNAPS that function together in the immunoassay to differentially detect or quantitate the target insecticidal protein and not the non-target insecticidal protein, resulting in the differential detection or quantitation of the target insecticidal protein. In other aspects, the non-target protein comprises an amino acid sequence that has at least a contiguous 27% of the target protein's amino acid sequence. In other aspects, the second ligand is an antibody or a synNAPS of the invention.

According to another aspect, the invention provides an immunoassay method to differentially detect or quantitate a target insecticidal protein in a biological sample comprising the target protein and a non-target insecticidal protein, the method comprising: (a) coating a first solid surface with a first synNAPS of the invention that binds the target protein but does not bind the non-target protein and coating a second solid surface with a second binding protein that binds the non-target protein; (b) contacting the biological sample with the synNAPS under conditions effective to allow the formation of a target protein-synNAPS complex but does not allow the formation of a non-target protein-synNAPS complex, resulting in a target protein-depleted biological sample; (c) removing the target protein-depleted biological sample and contacting the target protein-depleted biological sample with the second binding protein under conditions effective to allow the formation of a non-target protein-second binding protein complex; (d) detecting or quantitating the target protein complex on the first solid surface; and (e) detecting or quantitating the non-target protein on the second solid surface. In other aspects, the non-target protein comprises an amino acid sequence that has at least a contiguous 27% of the target protein's amino acid sequence In some embodiments of the above described aspects, the immunoassay is an enzyme-linked immunosorbent assay (ELISA), a Western blot, immunochromatography or immunolocaliztion. In one aspect of this embodiment, the immunoassay is carried out on a solid surface. In another aspect, the solid surface is a mictrotiter dish. In another aspect of this embodiment, the second ligand is an antibody or a second synNAPS different from the first synNAPS. In another aspect of this embodiment, the first synNAPS is used as a coating ligand and the second ligand is used as a detecting ligand. In another aspect of this embodiment, the first synNAPS is used as a detecting ligand and the second ligand is used as a coating ligand.

In some embodiments of the above described aspects of the invention, the biological sample is a transgenic plant sample. In some aspects of this embodiment, the transgenic plant is a transgenic corn plant. In other aspects, the transgenic corn plant comprises a transgenic corn event selected from the group consisting of event Bt11, event MIR604, event 5307, event MON89034 and event MON810. In other aspects, the transgenic corn plant comprises event Bt11, MIR604, event 5307 and optionally event MON89034. In other aspects, biological sample comprises a Cry1Ab protein from event Bt11, a mCry3A from MIR604, and an eCry3.1Ab hybrid Cry protein from event 5307. In still other aspects, the Cry1Ab comprises SEQ ID NO:1, the eCry3.1Ab comprises SEQ ID NO:2, and the mCry3A comprises SEQ ID NO:3. In other aspects, the biological sample further comprises a Cry1A.105 hybrid Cry protein from event MON89034. In still other aspects, the Cry1A.105 comprises SEQ ID NO:7.

BRIEF DESCRIPTION OF THE SEQUENCES IN THE SEQUENCE LISTING

SEQ ID NO:1 is an amino acid sequence of a Cry1Ab insecticidal protein.
SEQ ID NO:2 is an amino acid sequence of an eCry3.1Ab hybrid insecticidal protein.
SEQ ID NO:3 is an amino acid sequence of a mCry3A insecticidal protein.
SEQ ID NO:4 is an amino acid sequence of a Cry1Aa insecticidal protein.
SEQ ID NO:5 is an amino acid sequence of an Cry1Ai insecticidal protein.
SEQ ID NO:6 is an amino acid sequence of a Cry1Ab.1Ca insecticidal protein.
SEQ ID NO:7 is an amino acid sequence of an Cry1A.105 insecticidal protein.
SEQ ID NO:8 is an amino acid sequence of a Sac7d wild type ligand.
SEQ ID NO:9 is an amino acid sequence of a synNAPS-1 ligand.
SEQ ID NO:10 is an amino acid sequence of a synNAPS-2 ligand.
SEQ ID NO:11 is an amino acid sequence of a synNAPS-3 ligand.
SEQ ID NO:12 is an amino acid sequence of a synNAPS-4 ligand.
SEQ ID NO:13 is an amino acid sequence of a synNAPS-5 ligand.
SEQ ID NO:14 is an amino acid sequence of a synNAPS-6 ligand.
SEQ ID NO:15 is an amino acid sequence of a synNAPS-7 ligand.
SEQ ID NO:16 is an amino acid sequence of a synNAPS-8 ligand.
SEQ ID NO:17 is an amino acid sequence of a synNAPS-9 ligand.
SEQ ID NO:18 is an amino acid sequence of a synNAPS-10 ligand.
SEQ ID NO:19 is an amino acid sequence of a synNAPS-11 ligand.
SEQ ID NO:20 is an amino acid sequence of a synNAPS-12 ligand.
SEQ ID NO:21 is an amino acid sequence of a synNAPS-13 ligand.
SEQ ID NO:22 is an amino acid sequence of a synNAPS-14 ligand.
SEQ ID NO:23 is an amino acid sequence of a synNAPS-1tag ligand.
SEQ ID NO:24 is an amino acid sequence of a synNAPS-2tag ligand.
SEQ ID NO:25 is an amino acid sequence of a synNAPS-3tag ligand.
SEQ ID NO:26 is an amino acid sequence of a synNAPS-4tag ligand.
SEQ ID NO:27 is an amino acid sequence of a synNAPS-5tag ligand.
SEQ ID NO:28 is an amino acid sequence of a synNAPS-6tag ligand.
SEQ ID NO:29 is an amino acid sequence of a synNAPS-7tag ligand.
SEQ ID NO:30 is an amino acid sequence of a synNAPS-8tag ligand.
SEQ ID NO:31 is an amino acid sequence of a synNAPS-9tag ligand.
SEQ ID NO:32 is an amino acid sequence of a synNAPS-10tag ligand.

SEQ ID NO:33 is an amino acid sequence of a synNAPS-11tag ligand.
SEQ ID NO:34 is an amino acid sequence of a synNAPS-12tag ligand.
SEQ ID NO:35 is an amino acid sequence of a synNAPS-13tag ligand.
SEQ ID NO:36 is an amino acid sequence of a synNAPS-14tag ligand.
SEQ ID NO:37 is an amino acid sequence of a His-tag of the invention.
SEQ ID NO:38 is an amino acid sequence of an avidin-tag of the invention.
SEQ ID NO:39 is a nucleotide sequence encoding SEQ ID NO:24.
SEQ ID NO:40 is a nucleotide sequence encoding SEQ ID NO:31.
SEQ ID NO:41 is a nucleotide sequence encoding SEQ ID NO:35.
SEQ ID NO:42 is an amino acid sequence of an antigen-binding fragment of synNAPS1.
SEQ ID NO:43 is an amino acid sequence of an antigen-binding fragment of synNAPS2.
SEQ ID NO:44 is an amino acid sequence of an antigen-binding fragment of synNAPS3.
SEQ ID NO:45 is an amino acid sequence of an antigen-binding fragment of synNAPS4.
SEQ ID NO:46 is an amino acid sequence of an antigen-binding fragment of synNAPS5.
SEQ ID NO:47 is an amino acid sequence of an antigen-binding fragment of synNAPS6.
SEQ ID NO:48 is an amino acid sequence of an antigen-binding fragment of synNAPS7.
SEQ ID NO:49 is an amino acid sequence of an antigen-binding fragment of synNAPS8.
SEQ ID NO:50 is an amino acid sequence of an antigen-binding fragment of synNAPS9.
SEQ ID NO:51 is an amino acid sequence of an antigen-binding fragment of synNAPS10.
SEQ ID NO:52 is an amino acid sequence of an antigen-binding fragment of synNAPS11.
SEQ ID NO:53 is an amino acid sequence of an antigen-binding fragment of synNAPS12.
SEQ ID NO:54 is an amino acid sequence of an antigen-binding fragment of synNAPS13.
SEQ ID NO:55 is an amino acid sequence of an antigen-binding fragment of synNAPS14.
SEQ ID NOs:56-69 are amino acid sequences of synNAPS2 variants.
SEQ ID NOs:70-82 are amino acid sequences of synNAPS9 variants.
SEQ ID NOs:83-95 are amino acid sequences of synNAPS13 variants.
SEQ ID NO:96 is a consensus sequence of a synNAPS2 antigen-binding fragment.
SEQ ID NO:97 is a consensus sequence of a synNAPS9 antigen-binding fragment.
SEQ ID NO:98 is a consensus sequence of a synNAPS13 antigen-binding fragment.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used in the description of the invention and in the appended claims have the same meaning as commonly understood by one of ordinary skill in the art to which this invention belongs. The terminology used in the description of the invention herein is for the purpose of describing particular embodiments only and is not intended to be limiting of the invention.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Definitions

As used herein, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art.

The term "antigen" as used herein means a protein that comprises an epitope that can be recognized and bound by a ligand, such as a synNAPS of the present invention or an antibody.

As used herein, the term "antigen-binding site" or "paratope" refers to the part(s) of a ligand of the invention that binds to and is complementary to all or part of a target protein antigen. In a synNAPS peptide it is referred to as the synNAPS antigen-binding site, and comprises the part of the synNAPS that binds to and is complementary to all or part of the target protein antigen. Where a target protein is large, a synNAPS of the invention may only bind to a particular part of the target protein, which part is termed an epitope.

The terms "comprises" or "comprising," when used in this specification, specify the presence of stated features, integers, steps, operations, elements, or components, but do not preclude the presence or addition of one or more other features, integers, steps, operations, elements, components or groups thereof.

As used herein, the transitional phrase "consisting essentially of (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

The term "contacting" refers to a combining action that brings a ligand of the invention into contact with the biological sample and more particularly to a combining action which brings the ligand into contact with a transgenic protein of the invention in a manner that a binding interaction will occur between the ligand and the transgenic protein present in the biological sample.

The term "cross-reactivity" refers to the ability of a ligand to bind to multiple proteins. Such proteins may be target and non-target proteins.

The term "Cry protein" as used herein refers to an insecticidal protein that is a globular protein molecule which under native conditions accumulates as a protoxin in crystalline form during sporulation phase of a *Bacillus* sp., for example *Bacillus thuringiensis*, growth cycle. The terms "Cry toxin" and "delta-endotoxin" can be used interchangeably with the term "Cry protein." Current nomenclature for Cry proteins and gene that encode the Cry proteins is based upon amino acid sequence homology (Crickmore et al. (1998) Microbiol. Mol. Biol. Rev. 62:807-813). In this art-recognized classification, each Cry protein is assigned a unique name incorporating a primary rank (an Arabic number), a secondary rank (an uppercase letter), a tertiary rank (a lowercase letter), and a quaternary rank (another Arabic number). For example, according to Crickmoe et al., two Cry proteins with <45% homology would be assigned a unique primary rank, e.g. Cry1 and Cry2. Two Cry proteins with >45% but <70% homology would receive the same primary rank but would be assigned a different secondary rank, e.g. Cry1A and Cry1B. Two Cry proteins with 70% to 95% homology would be assigned the same primary and secondary rank but would be assigned a different tertiary rank, e.g. Cry1Aa and Cry1Ab. And two Cry proteins with >95% but <100% homology would be assigned the same primary, secondary and tertiary rank, but would be assigned a different quaternary rank, e.g. Cry1Ab1 and Cry1Ab2.

A "Cry1Ab protein" as used herein means an insecticidal crystal protein derived from *Bacillus thuringiensis*, whether naturally occurring or synthetic, comprising an amino acid sequence that has at least 96% identity to the holotype Cry1Ab amino acid sequence according to Crickmore et al. (supra), and disclosed at the internet website "lifesci.sussex.ac.uk/home/Neil_Crickmore/Bt/" as Accession No. AAA22330. Examples of Cry1Ab proteins (with accession numbers) include without limitation, Cry1Ab1 (AAA22330), Cry1Ab2 (AAA22613), Cry1Ab3 (AAA22561), Cry1Ab4 (BAA00071), Cry1Ab5 (CAA28405), Cry1Ab6 (AAA22420), Cry1Ab7 (CAA31620), Cry1Ab8 (AAA22551), Cry1Ab9 (CAA38701), Cry1Ab10 (A29125), Cry1Ab11 (112419), Cry1Ab12 (AAC64003), Cry1Ab13 (AAN76494), Cry1Ab14 (AAG16877), Cry1Ab15 (AAO13302), Cry1Ab16 (AAK55546), Cry1Ab17 (AAT46415), Cry1Ab18 (AAQ88259), Cry1Ab19 (AAW31761), Cry1Ab20 (ABB72460), Cry1Ab21 (ABS18384), Cry1Ab22 (ABW87320), Cry1Ab23 (HQ439777), Cry1Ab24 (HQ439778), Cry1Ab25 (HQ685122), Cry1Ab26 (HQ847729), Cry1Ab27 (JN135249), Cry1Ab28 (JN135250), Cry1Ab29 (JN135251), Cry1Ab30 (JN135252), Cry1Ab31 (JN135253), Cry1Ab32 (JN135254), Cry1Ab33 (AAS93798), Cry1Ab34 (KC156668), Cry1Ab35 (KT692985), and Cry1Ab36 (KY440260).

The term "Cry3" as used herein refers to insecticidal proteins that share a high degree of sequence identity or similarity to previously described sequences categorized as Cry3 according to Crickmore et al. (supra), examples of which are disclosed at the internet website "lifesci.sussex.ac.uk/home/Neil_Crickmore/Bt/" and include (with accession numbers), Cry3Aa1 (AAA22336), Cry3Aa2 (AAA22541), Cry3Aa3 (Caa68482), Cry3Aa4 (AAA22542), Cry3Aa5 (AAA50255), Cry3Aa6 (AAC43266), Cry3Aa7 (CAB41411), Cry3Aa8 (AAS79487), Cry3Aa9 (AAW05659), Cry3Aa10 (AAU29411), Cry3Aa11 (AAW82872), Cry3Aa12 (ABY49136), Cry3Ba1 (CAA34983), Cry3Ba2 (CAA00645), Cry3Ba3 (JQ397327), Cry3Bb1 (AAA22334), Cry3Bb2 (AAA74198), Cry3Bb3 (115475), and Cry3Ca1 (CAA42469). A Cry3 protein that has been engineered by inserting, substituting or deleting amino acids is referred to herein as a "modified Cry3 protein" or "mCry3 protein." Such "modified Cry3 proteins" typically have enhanced activity against certain insect pests, e.g. corn rootworm (*Diabrotica* sp.), compared to a wild-type Cry3 protein from which the "modified Cry3 protein" is derived. An example of a "modified Cry3 protein" is the "mCry3A" represented by the amino acid sequence of SEQ ID NO:3. Other examples of "modified Cry3" proteins include without limitation the "mCry3A proteins" disclosed in U.S. Pat. No. 8,247,369, the "mCry3A proteins" disclosed in U.S. Pat. No. 9,109,231, and the "mCry3B proteins" disclosed in U.S. Pat. No. 6,060,594.

The term "eCry3.1Ab" refers to an engineered hybrid insecticidal protein comprising in an N-terminus to C-terminus direction an N-terminal region of a Cry3A protein fused to a C-terminal region of a Cry1Aa or a Cry1Ab protein as described in U.S. Pat. No. 8,309,516. An example of an "eCry3.1Ab protein" is represented by the amino acid sequence of SEQ ID NO:2.

As used herein, the term "differential binding affinity" refers to the binding properties of a ligand, for example a synNAPS of the invention, in which the ligand binds to a target transgenic protein when the target transgenic protein is in the presence of one or more non-target transgenic proteins, and does not bind to the one or more non-target transgenic proteins. For example, a synNAPS ligand of the invention may differentially bind to a target Cry1Ab transgenic insecticidal protein when the Cry1Ab transgenic protein is in the presence of one or more non-target transgenic proteins, including an eCry3.1Ab insecticidal protein or a mCry3A insecticidal protein. Or, for another example, a different synNAPS ligand of the invention may differentially bind to a target eCry3.1Ab transgenic protein when the eCry3.1Ab transgenic protein is in the presence of one or more non-target transgenic proteins including Cry1Ab or mCry3A.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another plant line, whether transgenic or non-transgenic. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Non-limiting examples of such transgenic events include "event Bt11" (also Bt11 event or just Bt11), "event 5307" (also 5307 event or just 5307), "event MIR162 (also MIR162 event or just MIR162), "event MIR604" (also MIR604 event or just MIR604), "event MON810" (also MON810 event or just MON810) and "event MON89034" (also MON89034 event or just MON89034. Thus for example, the term "event Bt11", "Bt11 event" or "Bt11" as used herein means the original Bt11 transformant and/or progeny of the Bt11 transformant, including any plant derived therefrom.

As used herein the term "hybrid Cry protein" is an engineered insecticidal protein that does not exist in nature and that comprises a portion of a first Cry protein and another portion of a second Cry portion different from the first Cry protein. Typically, a "hybrid Cry protein" will comprise at least a contiguous 27% of a parent Cry protein's amino acid sequence (either the first Cry protein or the second Cry protein). The 27% number is calculated by dividing the number of contiguous parent Cry protein amino acids in the hybrid Cry protein divided by the total number of amino acids in the hybrid Cry protein. For example, the hybrid Cry protein, eCry3.1Ab (SEQ ID NO:2) has 174 Cry1Ab amino acids (positions 480-653) and a total of 653 amino acids. Therefore, eCry3A.1Ab has at least a contiguous 27% of a Cry1Ab protein's amino acid sequence. Other examples of a hybrid Cry protein according to the present invention is represented by SEQ ID NO:6 and SEQ ID NO:7.

The term "isolated" nucleic acid molecule, polynucleotide or polypeptide is a nucleic acid molecule, polynucleotide or polypeptide that no longer exists in its natural environment. An isolated nucleic acid molecule, polynucleotide or polypeptide of the invention may exist in a purified form or may exist in a recombinant host such as in a transgenic bacterial cell or a transgenic plant. Thus, an "isolated polypeptide" encompasses a polypeptide that is expressed within a transgenic plant.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue "Highly related insecticidal proteins" as used herein refers to proteins that have at least 95% overall sequence identity or that have motifs in common that have at least 80% sequence identity. Examples of insecticidal proteins that are "highly related" include Cry1Ab (SEQ ID NO:1) and eCry3.1Ab (SEQ ID NO: 2), that have a motif in common that has at least 80% sequence identity, and eCry3.1Ab (SEQ ID NO: 2) and mCry3A (SEQ ID NO: 3) that have a motif that has at least 80% sequence identity.

The term "gene stack" or "protein stack" refers to the introduction of two or more genes into the genome of an organism or the presence of two or more transgenic proteins in a transgenic organism. For example, it may be desirable to stack several genes, such as Cry1Ab, Vip3, mCry3A and eCry3.1Ab, in a corn plant so that the transgenic corn plant is protected from a broad spectrum of insect pests due to the production of the stacked proteins.

The term "identical" or "substantially identical," in the context of two nucleic acid or protein sequences, refers to two or more sequences or subsequences that have at least 60%, preferably 80%, more preferably 90, even more preferably 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In an especially preferred embodiment, the sequences are substantially identical over the entire length of the coding regions. Furthermore, substantially identical nucleic acid or protein sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, Md. 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A "synthetic non-antibody protein scaffold" or "synNAPS," is a Nanofitin® (Affilogic, Nantes, France) that binds to an insecticidal protein and can differentially detect and/or quantitate certain target transgenic insecticidal proteins comprised in a complex biological matrix, such as a transgenic plant or part thereof, when the target protein is in the presence of other non-target transgenic proteins, including non-target proteins that are closely related to the target protein.

As used herein "variant synNAPS" or "mutant synNAPS" include, but are not limited to, synNAPS containing deletions, additions and/or substitutions in the amino acid sequence of the synNAPS. One class of substitutions is conserved amino acid substitutions in which a given amino acid in a synNAPS polypeptide is substituted for another amino acid of like characteristics. Typical conservative substitutions are replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in, for example, Bowie et al., Science 247:1306-1310 (1990). A "variant synNAPS" of the invention can be fully functional or can lack function in one or more activities, e.g. ability to bind another molecule. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, truncations or extensions, or a substitution, insertion, inversion, or deletion of a critical residue or in a critical region. Methods useful for the identification of residues or regions of a synNAPS of the invention that may be required for binding to an insecticidal protein antigen are known in the art, for example site-directed mutagenesis or single sequential amino acid substitution mutagenesis.

Further substitutions may be introduced at the amino acid locations demonstrating functional sensitivity to the initial substitutions. Alternatively, or additionally, a crystal structure of an antigen-synNAPS complex to identify contact points between the synNAPS and antigen. Such contact residues and neighboring residues may be targeted or eliminated as candidates for substitution. Variants may be screened to determine whether they contain the desired properties.

In certain embodiments, a synNAPS provided herein is altered to increase or decrease the extent to which the synNAPS binds to the target insecticidal protein or to extend the synNAPS' spectrum of binding. Such modulation of binding may be accomplished by adding, deleting and/or substituting amino acids in the synNAPS peptide, particularly in the binding region of the synNAPS peptide.

A "target protein" as used herein means a protein, typically a transgenic protein, which is intended to be selectively detected and bound by a particular ligand, such as by a synNAPS of the present invention, when the target protein is in a complex biological matrix.

As used herein, the term "transgenic protein" means a protein or peptide produced in a non-natural form, location, organism, and the like. Therefore, a "transgenic protein" may be a protein with an amino acid sequence identical to a naturally-occurring protein or it may be a protein having a non-naturally occurring amino acid sequence. For example, a Cry1Ab protein having an amino acid sequence that is identical to a wild-type Cry1Ab protein from *Bacillus thuringiensis*, the naturally occurring Cry1Ab-producing organism, is a "transgenic protein" when produced within a transgenic plant or bacteria.

A "wild-type Cry1Ab protein" means a naturally occurring Cry1Ab protein or a Cry1Ab protein with minimal amino acid additions or substitutions to a naturally occurring Cry1Ab amino acid sequence and having the same or similar insecticidal activity or spectrum as the naturally occurring Cry1Ab protein. A "wild-type Cry1Ab protein" can be either a full-length protein or the truncated toxin portion thereof. For example, without limitation, wild-type Cry1Ab proteins according to the present invention include the Cry1Ab protein of SEQ ID NO:1.

The invention encompasses compositions, methods, assays and kits useful in the specific differential detection of transgenic target proteins, e.g. transgenic insecticidal proteins, which may be wild-type proteins, e.g. insecticidal Cry proteins, or transgenic engineered hybrid proteins, e.g. hybrid insecticidal Cry proteins, which may comprise all or part of a wild-type protein amino acid sequence, in complex biological samples comprising both the target protein and one or more non-target proteins, such as in transgenic plants or transgenic bacteria. Any protein introduced into a plant via transgenic expression technology may be analyzed using compositions and methods of the invention. Proteins suitable for multiplex analysis according to the invention may confer an output trait that renders the transgenic plant superior to its non-transgenic counterpart. Non-limiting examples of desirable traits that may be conferred include herbicide tolerance, tolerance or resistance to insect pests, resistance to environmental stress, enhanced yield, improved nutritional value, improved shelf life, altered oil content, altered oil composition, altered sugar content, altered starch content, production of plant-based pharmaceuticals, production of industrial products (e.g. polyhydroxyalkanoates: macromolecule polyesters considered ideal for replacing petroleum-derived plastics) and potential for bioremediation. Moreover, the expression of one or more transgenic proteins within a single plant species may be analyzed using compositions and methods of the present disclosure. The addition or modulation of two or more genes or desired traits into a single species of interest is known as gene stacking. Furthermore, the expression of one or more transgenic proteins may be analyzed concurrently in the presently disclosed multiplex analyses.

Preference for the particular target proteins to be analyzed is at the discretion of the artisan. Such proteins may be, but are not limited to, those from plants, animals, bacteria, yeast, and the like and may be proteins either not found in a non-transformed cell or found in a transformed cell. Particularly suitable proteins that are expressed in transgenic plants are those that confer tolerance to herbicides, insects, or viruses, and genes that provide improved nutritional value, increased yields, drought tolerance, nitrogen utilization, production of useful industrial compounds, processing characteristics of the plant, or potential for bioremediation. Examples of useful proteins include the insecticidal Cry proteins and Vip proteins from *Bacillus thuringiensis*, or engineered proteins derived therefrom, for conferring insect resistance, and the 5'-enolpyruvyl-3'-phosphoshikimate synthase (EPSPS) gene and any variant thereof for conferring tolerance to glyphosate herbicides. As is readily understood by those skilled in the art, any protein conferring a desired trait may be expressed in a plant cell using recombinant DNA technology and therefore may be a target protein according to the invention.

More particularly, the invention is related to small peptide affinity ligands called synNAPS (synthetic non-antibody protein scaffold) useful for detection, capture, identification or quantification of transgenic insecticidal proteins in complex biological matrices, such as samples from transgenic plants or transgenic microorganisms. The synNAPS of the invention have a variable binding region that have a unique propensity to bind specifically to targeted proteins. synNAPS have similar properties to antibodies in their ability to recognize and bind to specific epitopes of a target protein, however, they are about 20 times smaller than antibodies which provides substantial advantages when used in specific applications. For example, they have greater flexibility to bind to the target protein because their size causes less steric hindrance, they have higher tolerance to changes in temperature and pH conditions and they can contain multi-specificity tags for chemical modification. In addition, synNAPS have been identified that can differentially bind to highly related target insecticidal proteins when the target proteins are in a complex biological matrix comprising both the target protein and non-target proteins. Antibodies were not able to be generated with this differential specificity. The synNAPS ligands were successfully used in immunodetection systems, such as ELISA and Western blot, and in downstream processing systems, such as affinity columns, to detect and quantitate target insecticidal proteins.

The invention provides synNAPS, compositions, diagnostic methods and kits useful in carrying out the diagnostic methods that allow for the specific differential detection of highly similar transgenic insecticidal proteins, for example Cry1Ab, mCry3A and eCry3.1Ab, in complex biological samples comprising the transgenic insecticidal protein. The current state of the art is such that commercially available immunoassays based on antibodies are not useful in differentially detecting a Cry1Ab protein from a hybrid Cry protein engineered using a significant amount of the Cry1Ab protein's amino acid sequence when the two proteins are in the same biological sample because there is high cross-reactivity of the antibodies between the two types of proteins. For example, an antibody raised against a wild-type Cry1Ab for use in a Cry1Ab-detecting immunoassay cross reacts with a hybrid Cry protein having as little as 27% of its amino acids derived from the wild-type Cry1Ab protein when the two proteins are in the same biological sample. Therefore, for example, the quantitation of the wild-type Cry1Ab in such a complex biological sample may be confounded by the presence of one or more non-target wild-type Cry proteins or non-target hybrid Cry proteins. Furthermore, using detection of expressed proteins for identity preservation of commercial transgenic plant products comprising a wild-type Cry1Ab and one or more hybrid Cry proteins of the present invention is difficult because of cross-reactivity of antibodies to both the Cry1Ab proteins and the hybrid Cry proteins in the transgenic plant products. The methods and compositions disclosed herein provide a solution to these problems and rely on the differential binding of synNAPS ligands alone or in combination with other synNAPS or with antibodies. For example, a first synNAPS ligand of the invention may be used as the capture ligand to bind and isolate a target insecticidal protein. The bound synNAPS-target protein complex is then detected with a second ligand, which can be a second synNAPS or an antibody, fused to a detectable label.

Diagnostic assays of the invention can be carried out in many different formats, examples of which include an enzyme-linked immunosorbent assay (ELISA) and a dipstick format, which is also called a lateral flow stick. In ELISA, the protein antigen-ligand reaction takes place on a solid phase, typically in wells on microtiter plates. Antigen and this first ligand, also called the coating ligand, react and produce a stable complex, which can be visualized by addition of a second ligand, also called the detecting ligand, linked to an enzyme. The first and second ligands may be synNAPS or a combination of synNAPS and antibodies. Addition of a substrate for that enzyme results in a color formation, which can be measured photometrically or recognized by eye.

Dipstick formats (lateral flow sticks) typically use paper strips or plastic paddles as support for the capture ligand and this is then the reaction site. The strip/paddle is dipped in vials containing the different biological samples. Each dip is followed by a rinsing step. The final reaction includes a color change in the vial, where the strip/paddle is placed. Recent development of dipstick format has led to lateral flow techniques where reactants are transported through the channels of a membrane by capillary forces. One single step is enough for performing the assay, and controls for reagent performance are included. Ligands specific to the foreign protein are coupled to a color reagent and incorporated into the lateral flow strip. When the lateral flow strip is placed in a small amount of a biological sample, for example an extract from plant tissue, that contains a transgenic protein, binding occurs between the coupled ligand and the transgenic protein. A sandwich is formed with some, but not all the ligand that is coupled to the color reagent. The membrane contains two capture zones, one captures the bound transgenic protein and the other captures color reagent. These capture zones display a reddish color when the sandwich and/or non-reacted colored reagents are captured in the specific zones on the membrane. The presence of a single line (control line) on the membrane indicates a negative sample and the presence of two lines indicates a positive sample.

A synNAPS ligand of the invention or an antibody ligand may have a detectable label or tag. Detectable labels suitable for use in the detection ligands of the present invention include any compound or composition having a moiety that is detectable by spectroscopic, photochemical, biochemical, immunochemical, electrical, optical, or chemical means. Such labels include, for example, an enzyme, oligonucleotide, nanoparticle chemiluminophore, fluorophore, fluorescence quencher, chemiluminescence quencher, or biotin. Thus for example, in an immunoassay employing an optical signal, the optical signal is measured as an analyte concentration dependent change in chemiluminescence, fluorescence, phosphorescence, electrochemiluminescence, ultraviolet absorption, visible absorption, infrared absorption, refraction, surface plasmon resonance. In an immunoassay employing an electrical signal, the electrical signal is measured as an analyte concentration dependent change in current, resistance, potential, mass to charge ratio, or ion count. In an immunoassay employing a change-of-state signal, the change of state signal is measured as an analyte concentration dependent change in size, solubility, mass, or resonance.

Useful labels according to the present disclosure include magnetic beads (e.g., DYNABEADS), fluorescent dyes (e.g., fluorescein, Texas Red, rhodamine, green fluorescent protein) and the like (see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., 3H, 125I, 35S, 14C, or 32P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to each ligand prior to, or during, or after contact with the biological sample. So-called "direct labels" are detectable labels that are directly attached to or incorporated into the detection ligand prior to use in the assay. Direct labels can be attached to or incorporated into the ligand by any of a number of means well known to those of skill in the art. In contrast, so-called "indirect labels" typically bind to each ligand at some point during the assay. Often, the indirect label binds to a moiety that is attached to or incorporated into the detection agent prior to use. Thus, for example, each ligand can be biotinylated before use in an assay. During the assay, an avidin-conjugated fluorophore can bind the biotin-bearing detection agent, to provide a label that is easily detected. One of the ligands can be labelled or "tagged" with an avidin-tag which then interacts with a second ligand labelled with biotin.

In another example of indirect labeling, polypeptides capable of specifically binding immunoglobulin constant regions, such as polypeptide A or polypeptide G, can also be used as labels for detection ligands. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). Such polypeptides can thus be labeled and added to the assay mixture, where they will bind to each ligand, as well as to the autoantibodies, labeling all and providing a composite signal attributable to analyte and autoantibody present in the sample.

Some labels useful in the present disclosure may require the use of an additional reagent(s) to produce a detectable signal. In an ELISA, for example, an enzyme label (e.g., beta-galactosidase) will require the addition of a substrate (e.g., X-gal) to produce a detectable signal. In immunoassays using an acridinium compound as the direct label, a basic solution and a source of hydrogen peroxide are added.

According to some embodiments, the invention encompasses a synthetic non-antibody protein scaffold (synNAPS), or an antigen-binding fragment thereof, that binds to an insecticidal protein and optionally comprises an amino acid tag. In other embodiments, the insecticidal protein comprises an amino acid sequence of any of SEQ ID NOs:1-7 or a ligand-binding fragment of any of SEQ ID NOs:1-7. In other embodiments, the synNAPS comprises any of SEQ ID NOs:9-36. In still other embodiments, the synNAPS comprises any of SEQ ID NOs:10-17, 19, 21, 24-31, 33 or 35.

In other embodiments, the invention encompasses a synNAPS that comprises an amino acid sequence that has from at least 80% to at least 99% sequence identity to SEQ ID NO:10, SEQ ID NO:17 or SEQ ID NO:21 and wherein the amino acid sequence that has from at least 80% to at least 99% sequence identity to (a) SEQ ID NO:10 has a Tro (W) at a position corresponding to or at position 22 of SEQ ID NO:10, a Ser (S) at a position corresponding to or at position 29 of SEQ ID NO:10, a Tyr (Y) at a position corresponding to or at position 31 of SEQ ID NO:10 and a Arg (R) at a position corresponding to or at position 44 of SEQ ID NO:10; or (b) SEQ ID NO:17 has an Ile (I) at a position corresponding to or at position 29 of SEQ ID NO:17 and a Phe (F) at a position corresponding to or at position 42 of SEQ ID NO:17; or (c) SEQ ID NO:21 has a His (H) at a position corresponding to or at position 22 of SEQ ID NO:21, a Arg (R) at a position corresponding to or at position 31 of SEQ ID NO:21, a Leu (L) at a position corresponding to or at a position corresponding to or at position 40 of SEQ ID NO:21 and a Tyr (Y) at a position corresponding to or at position 44 of SEQ ID NO:21. In further aspects, the synNAPS has an amino acid sequence that comprises any of SEQ ID NOs:56-59, 61-63, 66, 67, 69-75, 77-79, 81-86, 88-90, 92 or 95.

In some embodiments, the invention encompasses an antigen-binding fragment of a synNAPS of the invention. In still other embodiments, the antigen-binding fragment comprises at least about 14 to at least about 65 amino acids of any of SEQ ID NOs: 9-36. In other embodiments, the antigen-binding fragment comprises any SEQ ID NOs:42-55. In still other embodiments, the antigen-binding fragment comprises any of SEQ ID NOs:96-98.

In some embodiments, the invention encompasses a synNAPS that comprises an antigen-binding fragment of the invention. In other embodiments, the antigen-binding fragment comprises any SEQ ID NOs:42-55. In still other embodiments, the antigen-binding fragment comprises any of SEQ ID NOs:96-98

In some embodiments, a synNAPS of the invention, or an antigen-binding fragment thereof, has a differential binding affinity to a target transgenic insecticidal protein when the target protein is in the presence of one or more non-target transgenic insecticidal proteins. In other embodiments, the target protein a) has at least 70% to at least 95% sequence identity across its entire length to one or more of the non-target proteins; or b) comprises a region that has at least 25% to at least 95% sequence identity to a region of one or more of the non-target proteins. In other embodiments, the target protein comprises a region that has at least 27% sequence identity to a region of one or more of the non-target proteins. In other embodiments, the target protein comprises a region that has at least 50%, 60%, 70%, 80%, 90%, 91%, 92%, 93%, 94%, 95%, 96%, 97%, 98%, 99% or 100% sequence identity to a region of one or more of the non-target proteins.

In certain aspects of the above described embodiments of the invention, the target protein is a Cry1A protein, a mCry3A protein, an eCry3.1Ab protein or a hybrid Cry protein comprising domain I and domain II of a Cry1Ab protein.

In other aspects of the above described embodiments, the one or more non-target proteins are selected from the group consisting of a Cry1A protein, a Cry1B protein, a Cry1F protein Cry1I protein, a Cry1J protein, a hybrid Cry protein comprising domain I and domain II of a Cry1Ab protein, a hybrid Cry protein comprising domain III of a Cry1F protein, a modified Cry3A protein, a hybrid Cry3 protein comprising domain III of a Cry1Ab protein, and a Vip3 protein.

In other aspects of the above described embodiments of the invention, the target protein is a Cry1A protein, a mCry3A protein, an eCry3.1Ab protein or a hybrid Cry protein comprising domain I and domain II of a Cry1Ab protein and the one or more non-target proteins are selected from the group consisting of a Cry1A protein, a Cry1B protein, a Cry1F protein Cry1I protein, a Cry1J protein, a hybrid Cry protein comprising domain I and domain II of a Cry1Ab protein, a hybrid Cry protein comprising domain III of a Cry1F protein, a modified Cry3A protein, a hybrid Cry3 protein comprising domain III of a Cry1Ab protein, and a Vip3 protein. In some embodiments, the Cry1A protein is a Cry1Aa, a Cry1Ab or a Cry1Ai. In other embodiments the hybrid Cry protein is a Cry1Ab.1Ca protein or a Cry1A.105 protein.

In still other aspects of the above described embodiments, the target protein is a) a Cry1Ab and the non-target proteins include a mCry3A or an eCry3.1Ab; or b) is an mCry3A and the non-target proteins include a Cry1Ab or an eCry3.1Ab; or c) is an eCry3.1Ab and the non-target proteins include a Cry1Ab or an mCry3A; or d) is a Cry1Ab or a Cry1Ab.1Ca and the non-target proteins include a Cry1Aa or a Cry1Ai; or e) is a Cry1Ab or a Cry1Ai protein and the non-target proteins include a Cry1Aa or a Cry1Ab.1C; or f) is a Cry1Ab, a Cry1Ai or a Cry1Ab.Cry1C protein and the non-target protein is a Cry1Aa; or g) is a Cry1Ab protein or a Cry1Ab.Cry1C protein and the non-target proteins include a Cry1Aa or a Cry1Ai protein; or h) is a Cry1Aa or a Cry1Ai protein and the non-target proteins include a Cry1Ab protein or a Cry1Ab.1Ca protein.

In still other aspects of the above described embodiments of the invention, wherein the Cry1Ab protein comprises an amino acid sequence represented by SEQ ID NO:1, the mCry3A protein comprises an amino acid sequence represented by SEQ ID NO:3, the eCry3.1Ab protein comprises an amino acid sequence represented by SEQ ID NO:2, the Cry1Aa protein comprises an amino acid sequence represented by SEQ ID NO:4, the Cry1Ai protein comprises an amino acid sequence represented by SEQ ID NO:5, the Cry1Ab.1Ca protein comprises an amino acid sequence represented by SEQ ID NO:6 or the Cry1A.105 protein comprises an amino acid sequence represented by SEQ ID NO:7.

In other embodiments, the synNAPS that binds specifically to Cry1Ab in the presence of mCry3A or eCry3.1Ab comprises SEQ ID NO:10 SEQ ID NO:11, SEQ ID NO:12 or SEQ ID NO:13. In other embodiments, the synNAPS that binds specifically to the mCry3A protein in the presence of Cry1Ab and eCry3.1Ab comprises SEQ ID NO:14, SEQ ID NO:15, SEQ ID NO:16 or SEQ ID NO:17. In still other embodiments, the synNAPS that binds specifically to eCry3.1Ab in the presence of Cry1Ab and mCry3A comprises SEQ ID NO:21. In other embodiments, the synNAPS that binds to Cry1Ab or Cry1Ab.1Ca in the presence of Cry1Aa or Cry1Ai comprises SEQ ID NO:13. In further embodiments, the synNAPS that binds to eCry3.1Ab or mCry3A or Cry1Ai or Cry1Aa in the presence of Cry1Ab comprises SEQ ID NO:19.

In other embodiments, the target protein and the non-target protein are comprised in a biological sample from a transgenic plant or a transgenic microorganism. In other embodiments, the transgenic plant is a corn plant, a soybean plant, a cotton plant, a canola plant, a wheat plant or a rice plant. In other embodiments, the transgenic microorganism is a bacteria, yeast or virus. In still other embodiments, the transgenic bacteria is *E. coli, Psuedomonas* sp. or *Bacillus* sp.

In some embodiments, the invention encompasses a nucleic acid molecule encoding a synNAPS of the invention. In other embodiments, the synNAPS is selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36. In still other embodiments, a nucleic acid molecule of the invention encodes a synNAPS comprising an amino acid sequence of any of SEQ ID NOs:56-69, or SEQ ID NOs:70-82 or SEQ ID NOs:83-95.

In still other embodiments, the invention encompasses a nucleic acid molecule that encodes an antigen-binding fragment of a synNAPS of the invention. In other embodiments, the antigen-binding fragment comprises at least about 14 to at least about 65 amino acids of any of SEQ ID NOs:9-36, or SEQ ID NOs:56-69, or SEQ ID NOs:70-82 or SEQ ID NOs:83-95. In other embodiments, the antigen-binding fragment comprises any SEQ ID NOs:40-53. In still other embodiments, the antigen-binding fragment comprises any of SEQ ID NOs:96-98.

In some embodiments, the invention further encompasses a transgenic organism comprising a nucleic acid molecule of the invention. In other embodiments, the transgenic organism is a transgenic plant or a transgenic microorganism. In other embodiments, the transgenic plant is a corn plant, a soybean plant, a cotton plant, a canola plant, a wheat plant or a rice plant. In still other embodiments, the microorganism is a bacteria, yeast or virus. In other embodiments, the bacteria is *E. coli, Pseudomonas* sp. or *Bacillus* sp.

In another embodiment, the invention encompasses a composition comprising a first synNAPS of the invention and a second ligand, wherein the synNAPS and the second ligand function together in an immunoassay of a biological sample comprising a target protein and a non-target protein to differentially detect or quantitate the target protein. In other embodiments, the non-target protein comprises an amino acid sequence that has at least a contiguous 27% of the target protein's amino acid sequence.

In some embodiments, the invention encompasses a diagnostic kit for differentially detecting a target insecticidal protein in a complex biological matrix which comprises the target insecticidal protein and a non-target insecticidal protein, wherein the kit comprises a first synNAPS of the invention and a second ligand that function together in an immunoassay to differentially detect or quantitate the target insecticidal protein. In other embodiments, the non-target protein comprises an amino acid sequence that has at least a contiguous 27% of the target protein's amino acid sequence.

In some aspects of the above described embodiments, the immunoassay is an enzyme-linked immunosorbent assay (ELISA), a Western blot, immunochromatography or immunolocaliztion. In one aspect of this embodiment, the immunoassay is carried out on a solid surface. In another aspect, the solid surface is a mictrotiter dish. In another aspect of this embodiment, the second ligand is an antibody or a second synNAPS different from the first synNAPS. In another aspect of this embodiment, the first synNAPS is used as a coating ligand and the second ligand is used as a detecting ligand. In another aspect of this embodiment, the first synNAPS is used as a detecting ligand and the second ligand is used as a coating ligand.

In some aspects of the above described embodiments, the biological sample is a transgenic plant sample. In other aspects of this embodiment, the transgenic plant is a transgenic corn plant. In other aspects, the transgenic corn plant comprises a transgenic corn event selected from the group consisting of event Bt11, event MIR604, event 5307, event MON89034 and event MON810. In other aspects, the transgenic corn plant comprises event Bt11, MIR604, event 5307 and optionally event MON89034. In other aspects, biological sample comprises a Cry1Ab protein from event Bt11, a mCry3A from MIR604, and an eCry3.1Ab hybrid Cry protein from event 5307. In still other aspects, the Cry1Ab comprises SEQ ID NO:1, the eCry3.1Ab comprises SEQ ID NO:2, and the mCry3A comprises SEQ ID NO:3. In other aspects, the biological sample further comprises a Cry1A.105 hybrid Cry protein from event MON89034. In still other aspects, the Cry1A.105 comprises SEQ ID NO:7.

In other embodiments, the synNAPS is selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22.

In still other embodiments, the synNAPS is tagged in such a way so as to be detectable by an enzyme reaction. In one embodiment, the synNAPS is tagged with a His-tag or an avidin-tag. In another embodiment the synNAPS is labelled with both a His-tag and an avidin-tag. In another embodiment, the His-tag comprises SEQ ID NO:40. In other embodiments, the avidin-tag comprises SEQ ID NO:41. In another embodiment, the tagged synNAPS is selected from the group consisting of SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36.

In some embodiments, the invention encompasses a method for differentially detecting or quantitating a target insecticidal protein in a biological sample comprising the target protein and a non-target insecticidal protein, the method comprising (a) obtaining a biological sample comprising the target insecticidal protein and the non-target insecticidal protein; (b) performing an immunoassay on the biological sample, wherein the immunoassay comprises use of a first synNAPS of the invention and a second ligand that function together in the immunoassay to differentially detect or quantitate the target insecticidal protein and not the non-target insecticidal protein, resulting in the differential detection or quantitation of the target insecticidal protein. In other embodiments, the non-target protein has at least a contiguous 27% of the target protein's amino acid sequence.

In other embodiments, the invention encompasses an immunoassay method to differentially detect or quantitate a target insecticidal protein in a biological sample comprising the target protein and a non-target insecticidal protein, the method comprising: (a) coating a first solid surface with a synNAPS of the invention that binds to the target protein but does not bind to the non-target protein and coating a second solid surface with a second binding protein that binds to the non-target protein; (b) contacting the biological sample with the synNAPS under conditions effective to allow the formation of a target protein-synNAPS complex but does not allow the formation of a non-target protein-synNAPS complex, resulting in a target protein-depleted biological sample; (c) removing the target protein-depleted biological sample and contacting the target protein-depleted biological sample with the second binding protein under conditions effective to allow the formation of a non-target protein-second binding protein complex; (d) detecting or quantitating the target protein complex on the first solid surface; and (e) detecting or quantitating the non-target protein on the second solid surface. In other embodiments, the non-target protein has at least a contiguous 27% of the target protein's amino acid sequence.

In other embodiments, the immunoassay is an enzyme-linked immunosorbent assay (ELISA), a Western blot, immunochromatography or immunolocaliztion. In embodiments of this aspect, the immunoassay is carried out on a solid surface. In other embodiments, the solid surface is a mictrotiter dish. In other embodiments, the second ligand is an antibody or a second synNAPS different from the first synNAPS. In other embodiments, the first synNAPS is used as a coating ligand and the second ligand is used as a detecting ligand. In still other embodiments, the first synNAPS is used as a detecting ligand and the second ligand is used as a coating ligand. In other embodiments, the synNAPS is selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. In other embodiments, the synNAPS is tagged in such a way so as to be detectable by an enzyme reaction. In another embodiment, the synNAPS is tagged with a His-tag or an avidin-tag. In another embodiment the synNAPS is labelled with both a His-tag and an avidin-tag. In another embodiment, the His-tag comprises SEQ ID NO:40. In another embodiment, the avidin-tag comprises SEQ ID NO:41. In other embodiments, the tagged synNAPS is selected from the group consisting of SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36.

In further embodiment, the biological sample in which a target insecticidal protein is differentially detected or quantitated is a transgenic plant sample. In some embodiments, the transgenic plant is a transgenic corn plant. In other embodiments, the transgenic corn plant comprises a transgenic corn event selected from the group consisting of event Bt11, event MIR604, event 5307, event MON89034 and event MON810. In other embodiments, the transgenic corn plant comprises event Bt11, MIR604, event 5307 and optionally event MON89034. In other embodiments, biological sample comprises a Cry1Ab protein from event Bt11, a mCry3A from MIR604, and an eCry3.1Ab hybrid Cry protein from event 5307. In still other embodiments, the Cry1Ab comprises SEQ ID NO:1, the eCry3.1Ab comprises SEQ ID NO:2, and the mCry3A comprises SEQ ID NO:3. In other embodiments, the biological sample further comprises a Cry1A.105 hybrid Cry protein from event MON89034. In still other embodiment, the Cry1A.105 comprises SEQ ID NO:7.

Embodiments of this invention can be better understood by reference to the following examples. The foregoing and following description of embodiments of the invention and the various embodiments are not intended to limit the claims, but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims.

EXAMPLES

Example 1: Identification of Non-Antibody Ligand Candidates

This example describes the screening of ligand clone libraries to identify non-antibody polypeptide ligands that recognize and bind to insecticidal proteins. The insecticidal proteins Cry1Ab (SEQ ID NO:1), eCry3.1Ab (SEQ ID NO:2) and mCry3A (SEQ ID NO:3) are native and engineered proteins, respectively, which are composed of three domains typical of Bt Cry proteins. The three proteins have certain portions of their amino acid sequences in common. Particularly, eCry3.1Ab (SEQ ID NO:2) comprises domains I and II of mCry3A (SEQ ID NO:3) and domain III of Cry1Ab (SEQ ID NO:1). Therefore, Cry1Ab, amino acids 475-615 of SEQ ID NO:1, and eCry3.1Ab, amino acids 480-620 of SEQ ID NO:2, have regions with 100% identity. mCry3A and eCry3.1Ab also share a region with 100% identity, that being amino acids 10-468 of mCry3A (SEQ ID NO:3) and amino acids 23-481 of eCry3.1Ab (SEQ ID NO:2). Because of these regions of high identity, attempts to generate individual antibodies that would differentially bind to the each of the three target insecticidal proteins was not successful.

Combinatorial libraries of evolved polypeptides derived from a wild-type Sac7d OB-fold protein (SEQ ID NO:8), as described in U.S. Pat. No. 9,422,548, were screened to identify ligand candidates for the Cry1Ab, eCry3.1Ab and mCry3A proteins. Briefly, the process was divided into three steps, step 1—discovery, step 2—identification and step 3—verification. This differential screening method identifies potential ligand candidates that bind to amino acid sequences unique to each target protein or recognize target proteins due to unique conformational changes in regions the proteins have in common.

In step 1, several rounds of screening and enrichment of ligands present in libraries were carried out to identify ligand candidates that bind to the target proteins independently, i.e. not in presence of non-target proteins. Three selections, one for each target protein, were carried out in parallel with four rounds of selection via Ribosome Display with *E. coli* ligand clone libraries (See, for example, Mouratou et al. 2011. In Ribosome Display and Related Technologies, pp. 315-331, SpringerLink). ELISA was used to screen bacterial extracts of clones using standard procedures. In round 1 the ligand libraries were panned using a target protein. In subsequent rounds 2 to 4, the library resulting from round 1 was pre-panned with a non-target protein and then panned with a target protein. For example, to select anti-Cry1Ab ligands, round 1 panned with a Cry1Ab target protein and rounds 2 to 4 pre-panned with eCry3.1Ab, a non-target protein in this Cry1Ab selection and panned with the Cry1Ab target protein. After all rounds of each selection were completed, ligand clones with the required binding profiles were sequenced. This discovery step resulted in 37 unique ligand sequences in 7 distinct sequence families that bound Cry1Ab and not eCry3.1Ab, 22 unique ligand sequences in 10 sequence families that bound eCry3.1Ab and not Cry1Ab with but with no clear binding result on mCry3A. For mCry3A, there was a very low ELISA signal due to target integrity so 4 unique sequences from 4 different sequence families that bound mCry3A were identified.

For step 2, 12 anti-Cry1Ab clones, 14 anti-eCry3.1Ab clones, and 4 anti-mCry3A clones were selected from step 1. In this step, purified ligands were assessed for their binding affinity to individual targets and for absence of cross-reactivity between targets using art recognized Bio-Layer Interfermetry (ForteBio, Menlo Park, Calif.) (See also Shah and Duncan, 2014. J. Vis. Exp. 84:51383), which measures biomolecular interactions. The ligand-target association was measured on a range of target concentrations from about 15.6 nM to about 1 µM. The specific objective was to identify one or more ligands that recognized Cry1Ab but not eCry3.1Ab, one or more ligands that recognized mCry3A but not eCry3.1Ab and one or ligands that recognized mCry3A but not Cry1Ab or eCry3.1Ab. Results of this step identified 14 ligand candidates (defined herein as synthetic non-antibody protein scaffolds or "synNAPS") that had adequate affinity and specificity to the target insecticidal proteins; synNAPS-1 (SEQ ID NO:9), -2 (SEQ ID NO:10), -3 (SEQ ID NO:11), -4 (SEQ ID NO:12) and -5 (SEQ ID NO:13) selected with Cry1Ab, synNAPS-6 (SEQ ID NO:14), -7 (SEQ ID NO:15), -8 (SEQ ID NO:16), -9 (SEQ ID NO:17) selected with mCry3A, and synNAPS-10 (SEQ ID NO:18), -11 (SEQ ID NO:19), -12 (SEQ ID NO:20), -13 (SEQ ID NO:21) and -14 (SEQ ID NO:22) selected with eCry3.1Ab. An alignment of the synNAPS that bind to Cry1Ab, eCry3.1Ab and mCry3A is shown in Tables 1, 2 and 3, respectively.

TABLE 1

Sequence alignment of Cry1Ab-selected synNAPS.

| Pos | Sequence | SEQ ID NO: | Start | End | Length | Matches | % Matches |
|---|---|---|---|---|---|---|---|
| Ref 1 | synNAPS2 | 10 | 1 | 66 | 66 aa | | |
| 2 | synNAPS1 | 9 | 1 | 66 | 66 aa | 52 | 78 |
| 3 | synNAPS3 | 11 | 1 | 66 | 66 aa | 53 | 80 |
| 4 | synNAPS4 | 12 | 1 | 66 | 66 aa | 58 | 87 |
| 5 | synNAPS5 | 13 | 1 | 66 | 66 aa | 53 | 80 |

```
synNAPS2    1 MVKVKFKYKGEEKEVDTSKIVWIGRFGKSVYFRYDDNGKTGAGRVYEKDA
synNAPS1    1......GPW............DVW.W..Y.D.F......V.I.S.T....
synNAPS3    1......RWG............WYVA.V..W.L.G......R......R....
synNAPS4    1....................SYVQ.A......N........G...F....
synNAPS5    1......VL............TYVA.Y..F.Q.D......F...V.L....
synNAPS2   51 PKELLDMLARAEREKK
synNAPS1   51................
synNAPS3   51................
```

TABLE 1-continued

Sequence alignment of Cry1Ab-selected synNAPS.

| | |
|---|---|
| synNAPS4 | 51 . . . . . . . . . . . . . . . . |
| synNAPS5 | 51 . . . . . . . . . . . . . . . . |

TABLE 2

Sequence alignment of eCry3.1Ab-selected synNAPS.

| Pos | Sequence | SEQ ID NO: | Start | End | Length | Matches | % Matches |
|---|---|---|---|---|---|---|---|
| Ref 1 | synNAPS13 | 21 | 1 | 66 | 66 aa | | |
| 2 | synNAPS10 | 18 | 1 | 66 | 66 aa | 53 | 80 |
| 3 | synNAPS11 | 19 | 1 | 66 | 66 aa | 53 | 80 |
| 4 | synNAPS12 | 20 | 1 | 66 | 66 aa | 53 | 80 |
| 5 | synNAPS14 | 22 | 1 | 66 | 66 aa | 53 | 80 |

| | |
|---|---|
| synNAPS13 | 1 MVKVKFKRWGEEKEVDTSKILHVLRVGKYVRFSYDDNGKLGAGYVTEKDA |
| synNAPS10 | 1 . . . . . . LMK . . . . . . . . . . . KW.N.H . . . . A.Y . . . . . . T.G.E.R . . . . |
| synNAPS11 | 1 . . . . . . GLG . . . . . . . . . . . RR . . . L..L.S.T . . . . . . I.L.D.H . . . . |
| synNAPS12 | 1 . . . . . . . LT . . . . . . . . . . . QW.A.F..F.D.L . . . . . . T.W.W.Y . . . . |
| synNAPS14 | 1 . . . . . . . YK . . . . . . . . . . . IF.Y.F..F.M.I . . . . . . T.H.D.R . . . . |
| synNAPS13 | 51 PKELLDMLARAEREKK |
| synNAPS10 | 51 . . . . . . . . . . . . . . . . |
| synNAPS11 | 51 . . . . . . . . . . . . . . . . |
| synNAPS12 | 51 . . . . . . . . . . . . . . . . |
| synNAPS14 | 51 . . . . . . . . . . . . . . . . |

TABLE 3

Sequence alignment pf mCry3A-selected synNAPS.

| Pos | Sequence | SEQ ID NO: | Start | End | Length | Matches | % Matches |
|---|---|---|---|---|---|---|---|
| Ref 1 | synNAPS9 | 17 | 1 | 66 | 66 aa | | |
| 2 | synNAPS6 | 14 | 1 | 66 | 66 aa | 52 | 78 |
| 3 | synNAPS7 | 15 | 1 | 66 | 66 aa | 51 | 77 |
| 4 | synNAPS8 | 16 | 1 | 66 | 66 aa | 53 | 80 |

| | |
|---|---|
| synNAPS9 | 1 MVKVKFAQGGEEKEVDTSKIYRVPRHGKIVFFMYDDNGKGGFGHVTEKDA |
| synNAPS6 | 1 . . . . . . MRW . . . . . . . . . . . TY.T.W..T.I.Y . . . . . . K.H.S.L . . . . |
| synNAPS7 | 1 . . . . . . KVH.K . . . . . . . . . LA.A.W..A.I.A . . . . . . H.R.Q.S . . . . |
| synNAPS8 | 1 . . . . . . HGR . . . . . . . . . . . FW.Y.D..R.L.R . . . . . . R . . . S.P . . . . |
| synNAPS9 | 51 PKELLDMLARAEREKK |
| synNAPS6 | 51 . . . . . . . . . . . . . . . . |
| synNAPS7 | 51 . . . . . . . . . . . . . . . . |
| synNAPS8 | 51 . . . . . . . . . . . . . . . . |

In step 3, the 14 synNAPS identified in step 2 were tested in verification experiments. Accordingly, each synNAPS clone was constructed with an N-terminal His-tag (SEQ ID NO:37) and a C-terminal avidin-tag (SEQ ID NO:38). The 14 tagged synNAPS are disclosed as SEQ ID NOs:23-36. Each tagged synNAP was produced in an E. coli BirA strain (See, for example, Chapman-Smith and Cronan, 1999. Trends Biochem. Sci. 24:359-363) for in vivo biotinylation. High-binding 96-well plates (Nunc Maxisorp) were coated at 4° C. overnight with 1 µg/ml of Cry1Ab, eCry3.1Ab or mCry3A in 25 mM borate, 75 mM NaCl, pH 8.5 (100 µl/well). Plates were washed three times with phosphate buffered saline pH 7.3 (PBS) containing 0.05% Tween-20 (PBST). Each ligand in ELISA diluent (PBST containing 1% bovine serum albumin) was added to the plate (100 µl/well), incubated for 1 hr at room temperature (RT) with shaking, and washed five times. For detection through the biotin end of the synNAPS ligand, 1 µg/ml Streptavidin-alkaline phosphatase (Jackson ImmunoResearch Labs, West Grove, Pa.) in ELISA diluent was added to the plate, incubated for 1 hr at RT/shaking, and washed as before. Substrate p-nitrophenyl phosphate (SurModics, Eden Prairie, Minn.) was added (100 µl/well) and allowed to develop for 30 min at room temperature. The absorbance was measured at 405 nm using a microplate reader (BioTek Powerwave XS2, Winooski, Vt.). For detection using the HIS-tag end of the synNAPS ligand, 1/4000 dilution of RGS-His HRP conjugate (Qiagen) in ELISA diluent was added to the plate, incubated for 1 hr at RT/shaking, and washed as before. Substrate Tetramethylbenzidine (SurModics, Eden Prairie, Minn.) was added (100 µl/well) and allowed to develop for 15-30 min at room temperature with shaking. The reaction was stopped using 1 N HCl (100 µl/well) and absorbance was measured at 450 nm.

Based on the results of the step 3 verification experiments, synNAPS-2 (SEQ ID NO:10), which differentially binds to Cry1Ab, synNAPS-9 (SEQ ID NO:17), which differentially binds to mCry3A, and synNAPS-13 (SEQ ID NO:21), which differentially binds to eCry3.1Ab, were chosen for further experiments with transgenic plants.

Example 2. Screening Spectrum of Insecticidal Proteins

This example describes experiments to assess the binding properties of synNAPS against a wide spectrum of insecticidal proteins. The synNAPS were assessed for binding to wild-type and engineered hybrid insecticidal proteins, including a Cry1Aa, Cry1Ab, Cry1Ai, Cry1Ba, Cry1F, Cry1I, Cry1Jc, hybrid Cry1Ab.1Ca, hybrid eCry3.1Ab, hybrid Cry1Gb.Cry1Ig, hybrid Cry1Gb.1Fa, mCry3A and Vip3Aa protein, using the ELISA immunoassay described above. The proteins BSA and streptavidin-AP were used as negative controls. Briefly, the insecticidal proteins listed above were coated on 96-well plates overnight at a concentration of 500 ng/ml. 10 nM of each tagged synNAPS was mixed with 0.1 µg/ml streptavidin-alkaline phosphtase (SA-AP) was added to each well and incubated 1 hr at room temperature with shaking. The synNAPS-protein complexes were detected with pNPP and read at 405 nm after 15 min. Results are shown in Table 4, which indicate that synNAPS having at least 80% identity to synNAPS-2 (SEQ ID NO:10) bind to the target protein Cry1Ab but do not bind to the non-target proteins eCry3.1Ab or mCry3A, and that synNAPS having at least 77% identity to synNAPS-9 (SEQ ID NO:17) bind to the target protein mCry3A but do not bind to the non-target proteins Cry1Ab or eCry3.1Ab. The results further indicate that a) the target proteins for synNAPS-2 are Cry1Ab, Cry1Ai or a hybrid with domains I and II of Cry1Ab, e.g. Cry1Ab.1Ca and the non-target proteins include eCry3.1Ab, mCry3A, Cry1Aa, Cry1B, Cry1F, Cry1I, Cry1J, Cry1Gb.1Fa, Cry1Gb.1Ig, and Vip3; and b) the target proteins for synNAPS-3 are Cry1Ab or Cry1Ai and the non-target proteins include eCry3.1Ab, mCry3A, Cry1Aa, Cry1B, Cry1F, Cry1I, Cry1J, a hybrid Cry protein with domains I and II of Cry1Ab, e.g. Cry1Ab.1Ca, Cry1Gb.1Fa, Cry1Gb.1Ig, and Vip3; and c) the target proteins for synNAPS-4 are Cry1Ab, Cry1Ai and Cry1Ab.1Ca and the non-target proteins include eCry3.1Ab, mCry3A, Cry1Aa, Cry1B, Cry1F, Cry1I, Cry1J, Cry1Gb.1Fa, Cry1Gb.1Ig, and Vip3; and d) the target proteins for synNAPS-5 are Cry1Ab and Cry1Ab.1Ca and the non-target proteins include eCry3.1Ab, mCry3A, Cry1Aa, Cry1Ai, Cry1B, Cry1F, Cry1I, Cry1J, Cry1Gb.1Fa, Cry1Gb.1Ig, and Vip3; and e) the target protein for synNAPS-6, -7, 8, and -9 is mCry3A and the non-target proteins include eCry3.1Ab, Cry1Aa, Cry1Ab, Cry1Ai, Cry1B, Cry1F, Cry1I, Cry1J, Cry1Gb.1Fa, Cry1Gb.1Ig, and Vip3; and f) the target proteins for synNAPS-11 are mCry3A, eCry3.1Ab, Cry1Aa and Cry1Ai and the non-target proteins include Cry1Ab, Cry1B, Cry1F, Cry1I, Cry1J, Cry1Ab.1Ca, Cry1Gb.1Fa, Cry1Gb.1Ig, and Vip3; and g) the target protein for synNAPS-13 is eCry3.1Ab and the non-target proteins include mCry3A, Cry1Aa, Cry1Ab, Cry1Ai, Cry1B, Cry1F, Cry1I, Cry1J, Cry1Ab.1Ca, Cry1Gb.1Fa, Cry1Gb.1Ig, and Vip3. Results further demonstrate that none of the synNAPS bound to the wild-type Cry proteins Cry1I, Cry1F and Cry1Ba, the hybrid Cry protein Cry1Gb.1F, or the vegetative insecticidal protein, Vip3Aa (not shown in table).

TABLE 4

Results of synNAPS binding experiment with insecticidal proteins.

| Selection Protein | Ligand (synNAPS No.) | Binding to Insecticidal Protein (NB = No binding) | | | | | |
|---|---|---|---|---|---|---|---|
| | | Cry1Ab | mCry3A | eCry3.1Ab | Cry1Ai | Cry1Aa | Cry1Ab.1Ca |
| Cry1Ab | 1 | NB | NB | NB | NB | NB | NB |
| | 2 | 1.8 | NB | NB | 2.5 | NB | 1.0 |
| | 3 | 0.75 | NB | NB | 1.5 | NB | NB |
| | 4 | 1.75 | NB | NB | 2.6 | NB | 0.75 |
| | 5 | 1.1 | NB | NB | NB | NB | 1.6 |
| mCry3A | 6 | NB | 1.1 | NB | NB | NB | NB |
| | 7 | NB | 0.7 | NB | NB | NB | NB |
| | 8 | NB | 1.6 | NB | NB | NB | NB |
| | 9 | NB | 0.7 | NB | NB | NB | NB |
| eCry3.1Ab | 10 | NB | NB | NB | NB | NB | NB |
| | 11 | NB | 2.9 | 1.5 | 0.7 | 0.6 | NB |
| | 12 | NB | NB | NB | NB | NB | NB |
| | 13 | NB | NB | 0.8 | NB | NB | NB |
| | 14 | NB | NB | NB | NB | NB | NB |

Example 3. ELISA Development Using synNAPS

This example describes the development of ELISA methods to detect or quantitate target insecticidal proteins in a composition comprising the target protein and one or more non-target insecticidal proteins using synNAPS and antibody combinations. For this example, immunoassays in which a synNAPS of the invention was used as the coating ligand and an antibody used as the detecting ligand as well as immunoassays in which an antibody was used as a coating ligand and a synNAPS was used as the detecting ligand were evaluated for specificity and sensitivity compared to an ELISA method in which an antibody was used as the coating and detecting ligand.

svnNAPS-Antibody Assays

Pierce streptavidin high binding 96-well plates (ThermoFisher Scientific, Rockford, Ill.) were coated at 4° C. overnight with 100 µl/well 100 nM synNAPS-2, synNAPS-9 or synNAPS-13 in phosphate buffered saline pH 7.3 (PBS) containing 1% bovine serum albumin (ELISA diluent). Plates were washed three times with PBS containing 0.05% Tween-20 (PBST). Samples containing Cry1Ab, eCry3.1Ab and mCry3A or standards in ELISA diluent were added to the plate (100 µl/well), incubated for 1 hr at room temperature (RT) with shaking, and washed five times. 100 µl/well of HRP-MAb170 anti-mCry3A antibody or HRP-Mab70 anti-Cry1Ab antibody in ELISA diluent (1/10,000 dilution)

was added to the plate, incubated for 1 hr at RT/shaking, and washed as before. Substrate Tetramethylbenzidine (SurModics, Eden Prairie, Minn.) was added (100 μl/well) and allowed to develop for 15-30 min at room temperature with shaking. The reaction was stopped using 1 N HCl (100 μl/well). The absorbance was measured at 450 nm using a microplate reader (BioTek Powerwave XS2, Winooski, Vt.). The standard curve used a four-parameter curve fit to plot the concentrations versus the absorbance. Results in Table 5 indicated synNAPS of the invention can act as the coating or capture ligand in concert with an antibody acting as the detection ligand.

TABLE 5

Differential detection of target proteins with synNAPS.

| | Absorbance at protein concentration (ng/ml) | | |
|---|---|---|---|
| Ligand | Cry1Ab (10) | mCry3A (60) | eCry3.1Ab (40) |
| synNAPS-2 | 4.0 | 0.0 | 0.0 |
| synNAPS-9 | 0.0 | 2.0 | 0.0 |
| synNAPS-13 | 0.0 | 0.0 | 2.0 |

Antibody-synNAPS Assays

High-binding 96-well plates (Nunc Maxisorp) were coated at 4° C. overnight with 2 μg/ml MAb170 anti-mCry3A in 25 mM borate, 75 mM NaCl, pH 8.5 (100 μl/well). Plates were washed three times with phosphate buffered saline pH 7.3 (PBS) containing 0.05% Tween-20 (PBST). Samples containing Cry1Ab, eCry3.1Ab and mCry3A or standards in ELISA diluent (PBST containing 1% bovine serum albumin) were added to the plate (100 μl/well), incubated for 1 hr at room temperature (RT) with shaking, and washed five times. 100 μl/well of 10 nM synNAPS-13 plus 0.1 μg/ml Streptavidin-alkaline phosphatase (Jackson ImmunoResearch Labs, West Grove, Pa.) in ELISA diluent was added to the plate, incubated for 1 hr at RT/shaking, and washed as before. Substrate p-nitrophenyl phosphate (SurModics, Eden Prairie, Minn.) was added (100 μl/well) and allowed to develop for 30 min at room temperature. The absorbance was measured at 405 nm using a microplate reader (BioTek Powerwave XS2, Winooski, Vt.). The standard curve used a four-parameter curve fit to plot the concentrations versus the absorbance. Results indicated that eCry3.1Ab was differentially detected with an absorbance of 2.4 at protein concentration of 40 ng/ml demonstrating that there was no interference from the non-target proteins.

The results disclosed in this example demonstrate that synNAPS of the invention can be used as the capture ligand or the detecting ligand in immunoassays of complex biological samples. Quantitation of targets proteins using an ELISA method in which an antibody acts as the coating ligand and a synNAPS acts as the detecting ligand was comparable to an ELISA using antibodies as both the coting and detecting ligands. Quantitation of targets proteins using an ELISA method in which a synNAPS acts as the coating ligand and an antibody acts as the detecting ligand was results in good coorelation with an ELISA using antibodies as both the coting and detecting ligands, but had about a 5-fold lower sensitivity.

Example 4. Affinity Purification Using synNAPS

This example describes the use of synNAPS of the invention in an affinity purification method. Experiments were designed to test whether synNAPS-13, which was shown to bind differentially to eCry3.1Ab as described above, could be used to selectively purify a target protein, eCry3.1Ab, from a complex plant matrix containing the target protein and the non-target proteins Cry1Ab and mCry3A, which have regions of substantial identity to the target protein. Streptavidin T1 beads (Invitrogen Dynabeads MyOne), 0.1 ml, were washed 3× with PBS following manufacturer's procedure and resuspended in 0.5 ml 0.1% BSA in PBST. 20 ug synNAPS-13 was added and the mixture incubated about 1 hr at 4° C. with rotation. The beads were washed 3× with 0.1% BSA in PBST before adding 0.5 ml of leaf extract from transgenic corn expressing Cry1Ab, eCry3.1Ab and mCry3A and incubated for 30 m at RT with rotation. The supernatant was removed and saved for testing. The beads were washed as before and then eluted with 0.2 ml 0.1M Glycine pH 2.0. Eluate was added to a tube containing 20 μl 0.5M Tris pH 8.5 and volume brought up to 0.5 ml with PBS. Samples were taken from the original leaf extract (comprises all three proteins), the depleted supernatant (should comprise only Cry1Ab and mCry3A) and the eluate (should comprise only eCry3.1Ab) and tested in a Cry1Ab, an eCry3.1Ab and a mCry3A ELISA. Results, shown in Table 6, indicate that the synNAPS-13 ligand specifically detected and captured eCry3.1Ab from the transgenic corn leaf extract even when the target protein was in the presence of non-target proteins having regions of substantial identity in common with the target protein.

TABLE 6

Affinity purification of a target protein from a complex plant matrix.

| | Quantity of Protein (ng/ml) | | |
|---|---|---|---|
| Sample | eCry3.1Ab (target) | Cry1Ab (non-target) | mCry3A (non-target) |
| Extract | 174.6 | 112.8 | 153.5 |
| Supernatant 1 | 38.6 | 118.2 | 145.3 |
| Elution 1 | 75.7 | 0.0 | 0.0 |
| Elution 2 | 12.0 | 0.0 | 0.0 |
| Supernatant 2 | 12.9 | 113.4 | 130.6 |
| Elution 3 | 2.8 | 0.0 | 0.0 |
| Supernatant 3 | 4.7 | 88.3 | 124.0 |

Example 5. Dot Blot Assays Using synNAPS of the Invention

This example describes the use of synNAPS of the invention in dot blots to differentially detect target transgenic proteins. Previously it was demonstrated that synNAPS2, NsynNAPS9, and synNAPS13 could specifically bind native Cry1Ab, mCry3A, and eCry3.1Ab proteins, respectively. To investigate potential applications of synNAPS in Dot Blots, native Cry1Ab, mCry3A and eCry3.1Ab proteins were individually spotted onto nitrocellulose membrane strips at amounts of 9, 19, 38, 75, and 150 ng. After air drying for about 2 hours, the protein-spotted strips were blocked with blocking buffer of TBS, pH8.0 containing 3% non-fat milk for 30 minutes, and then incubated with respective synNAPS at a concentraton of 10 nM in the same blocking buffer overnight in a coldroom. After washing 3×10 min with TBST at room temperature, the strips were incubated with AP-streptavidin conjugate for 1 hour at room temperature. Detection was visualized by incubating strips in the BCIP/NBT liquid substrate for 1 min.

The results showed that the lowest level of detection of synNAPS2 was 75 ng of Cry1Ab and the lowest level of detection of synNAPS9 was 150 ng of mCry3A. Under these experimental conditions, no detection of eCry3.1Ab was observed at the different levels from 38 ng to 150 ng by using synNAPS13 suggesting that it has lower sensitivity than synNAPS2 and synNAPS in these types of dot blots.

Example 6. Identification of Key Functional Amino Acid Positions in synNAPS

This example describes the characterization of antigen binding sites of synNAPS ligands, synNAPS2, synNAPS9 and synNAPS13, with antigens Cry1Ab, mCry3A and eCry3.1Ab. Amino acid positions critical to functional binding for synNAPS2, synNAPS9 and synNAPS13 binding regions were identified by amino acid substitution mutagenesis at amino acid positions corresponding to amino acid positions 7, 8, 9, 21, 22, 23 or 24, 26, 29, 31, 33, 40, 42, 44 and 46 of SEQ ID NO:8. Binding affinity was determined for each variant synNAPS in ELISA. A substitution at a position that resulted in the abolishment of binding efficiency indicated that the position was critical for functional binding. A parental clone for each synNAPS, i.e. synNAPS2 (SEQ ID NO:10), synNAPS9 (SEQ ID NO:17) or synNAPS13 (SEQ ID NO:21), was used as a positive control.

Each synNAPS variant was constructed with an N-terminal His-tag (SEQ ID NO:37). Each tagged synNAPS variant was produced in E. coli. High-binding 96-well plates (Nunc Maxisorp) were coated at 4° C. overnight with 1 µg/ml of Cry1Ab, eCry3.1Ab or mCry3A in 25 mM borate, 75 mM NaCl, pH 8.5 (100 µl/well). Plates were washed three times with phosphate buffered saline pH 7.3 (PBS) containing 0.05% Tween-20 (PBST). Each ligand in ELISA diluent (PBST containing 1% bovine serum albumin) was added to the plate (100 µl/well), incubated for about 1 hr at room temperature (RT) with shaking, and washed five times. For detection, 1/4000 dilution of RGS-His HRP conjugate (Qiagen) in ELISA diluent was added to the plate, incubated for 1 hr at RT/shaking, and washed. Substrate Tetramethylbenzidine (SurModics, Eden Prairie, Minn.) was added (100 µl/well) and allowed to develop for 15-30 min at room temperature with shaking. The reaction was stopped using 1 N HCl (100 µl/well) and absorbance was measured at 450 nm.

Results of the ELISA for Cry1Ab binding, mCry3A binding and eCry3.1Ab binding are shown in Table 7, 8 and 9, respectively.

TABLE 7

Binding affinity of synNAPS2 variants to a Cry1Ab antigen

| synNAPS Variant | synNAPS SEQ ID NO: | Cry1Ab (SEQ ID NO: 1) Binding (OD 450 nm) | No Target |
|---|---|---|---|
| synNAPS2 | 10 | 4.0 | 0.0 |
| K7A | 56 | 4.0 | 0.0 |
| Y8A | 57 | 2.4 | 0.0 |
| K9A | 58 | 4.0 | 0.0 |
| V21A | 59 | 3.8 | 0.0 |
| W22A | 60 | 0.0 | 0.0 |
| I23A | 61 | 3.2 | 0.0 |
| G24A | 62 | 4.0 | 0.0 |
| F26A | 63 | 3.7 | 0.0 |
| S29A | 64 | 0.0 | 0.0 |
| Y31A | 65 | 0.0 | 0.0 |
| R33A | 66 | 2.2 | 0.0 |

TABLE 7-continued

Binding affinity of synNAPS2 variants to a Cry1Ab antigen

| synNAPS Variant | synNAPS SEQ ID NO: | Cry1Ab (SEQ ID NO: 1) Binding (OD 450 nm) | No Target |
|---|---|---|---|
| T40A | 67 | 4.0 | 0.0 |
| R44A | 68 | 0.0 | 0.0 |
| Y46A | 69 | 3.5 | 0.0 |

Results of the synNAPS2 mutations demonstrate that mutating an amino acid position of a synNAPS ligand that binds to a Cry1Ab antigen that corresponds to amino acid positions 22, 29, 31 and 44 of SEQ ID NO:10 completely knocks out Cry1Ab binding. Specifically, mutating W22A, S29A, Y31A and R44A of SEQ ID NO:10 knocks out Cry1Ab binding of synNAPS2 (SEQ ID NO:10). Mutations at an amino acid position corresponding to amino acid positions 8, 21, 23, 26, 33 and 46 reduce binding affinity to Cry1Ab from about 5% to about 50%. Specifically, the mutations Y8A, V21A, I23A, F26A, R33A and Y46A of SEQ ID NO:10 reduced a synNAPS2 ligand binding affinity to Cry1Ab from about 5% to about 50% of the binding affinity of SEQ ID NO:10.

TABLE 8

Binding affinity of synNAPS9 variants to a mCry3A antigen.

| synNAPS Mutant | synNAPS SEQ ID NO: | mCry3A (SEQ ID NO: 2) Binding (OD 450 nm) | No Target |
|---|---|---|---|
| synNAPS9 | 17 | 2.5 | 0.0 |
| Q8A | 70 | 2.8 | 0.0 |
| G9A | 71 | 1.5 | 0.0 |
| Y21A | 72 | 1.8 | 0.0 |
| R22A | 73 | 1.0 | 0.0 |
| P24A | 74 | 0.5 | 0.0 |
| H26A | 75 | 1.8 | 0.0 |
| I29A | 76 | 0.0 | 0.0 |
| F31A | 77 | 1.4 | 0.0 |
| M33A | 78 | 2.8 | 0.0 |
| G40A | 79 | 1.7 | 0.0 |
| F42A | 80 | 0.2 | 0.0 |
| H44A | 81 | 2.1 | 0.2 |
| T46A | 82 | 2.8 | 0.0 |

Results of the synNAPS9 mutations demonstrate that mutating an amino acid position of a synNAPS ligand that binds to a mCry3A antigen that corresponds to amino acid positions 24, 29 and 42 of SEQ ID NO:17 completely or nearly completely knocks out mCry3A binding. Specifically, mutating P24A, I29A and F42A of SEQ ID NO:17 knocks out or nearly knocks out mCry3A binding of synNAPS9 (SEQ ID NO:17). Mutations at an amino acid position corresponding to amino acid positions 9, 21, 22 26, 31, 40 and 44 reduce binding affinity to mCry3A from about 16% to about 60%. Specifically, the mutations G9A, Y21A, H26A, F31A, G40A and H44A of SEQ ID NO:17 reduced a synNAPS9 ligand binding affinity to mCry3A from about 16% to about 60% of the binding affinity of SEQ ID NO:17. In addition, Mutations at amino acid positions corresponding to amino acid positions 8, 33 and 46 of SEQ ID NO:17 increased binding affinity of a synNAPS13 ligand. Specifically, the mutations Q8A, M33A and T46A of SEQ ID NO:17 increased the binding affinity to mCry3A to about 112% of that of SEQ ID NO:17.

TABLE 9

Binding affinity of synNAPS13 variants to an eCry3.1Ab antigen.

| | | Binding (OD 450 nm) | |
|---|---|---|---|
| synNAPS Variant | synNAPS SEQ ID NO: | eCry3.1Ab (SEQ ID NO: 3) | No Target |
| synNAPS13 | 21 | 4.1 | 0.0 |
| K7A | 83 | 3.0 | 0.0 |
| R8A | 84 | 2.4 | 0.0 |
| W9A | 85 | 1.0 | 0.0 |
| L21A | 86 | 1.8 | 0.0 |
| H22A | 87 | 0.0 | 0.0 |
| L24A | 88 | 1.1 | 0.0 |
| V26A | 89 | 1.8 | 0.0 |
| Y29A | 90 | 2.6 | 0.0 |
| R31A | 91 | 0.0 | 0.0 |
| S33A | 92 | 4.1 | 0.0 |
| L40A | 93 | 0.5 | 0.0 |
| Y44A | 94 | 0.4 | 0.0 |
| T46A | 95 | 4.1 | 0.0 |

Results of the synNAPS13 mutations demonstrate that mutating an amino acid position of a synNAPS ligand that binds to an eCry3.1Ab antigen that corresponds to amino acid positions 22, 31, 40 and 44 of SEQ ID NO:21 completely or nearly completely knocks out eCry3.1Ab binding. Specifically, mutating H22A, R31A, L40A and Y44A of SEQ ID NO:21 knocks out or nearly knocks out eCry3.1Ab binding of synNAPS13 (SEQ ID NO:21). Mutations at an amino acid position corresponding to amino acid positions, 7, 8, 9, 21, 24 26 and 29 reduce binding affinity to eCry3.1Ab from about 27% to about 76%. Specifically, the mutations K7A, R8A, W9A, L21A, L24A, V26A and Y29A of SEQ ID NO:21 reduced a synNAPS13 ligand binding affinity to eCry3.1Ab from about 27% to about 76% of the binding affinity of SEQ ID NO:21.

The results also demonstrate that certain amino acid positions in the binding domain are critical to full functionality of multiple synNAPS ligands. A summary of the data across synNAPS is shown in Table 10, where "++" means equal binding to non-mutated synNAPS, "+" means reduced binding compared to non-mutated synNAPS, and "–" means no binding compared to non-mutated synNAPS.

TABLE 10

Summary of binding affinity of different synNAPS.

| Mutated Position Amino Acid | Binding Affinity Compared to Non-mutated synNAPS | | |
|---|---|---|---|
| | synNAPS2-Cry1Ab (SEQ ID NO: 10) | synNAPS9-mCry3A (SEQ ID NO: 17) | synNAPS13-eCry3.1Ab (SEQ ID NO: 21) |
| X9A | ++ | + | + |
| X21A | ++ | + | + |
| X22A | — | — | + |
| X24A | ++ | + | — |
| X29A | — | ++ | — |
| X31A | — | — | + |
| X40A | ++ | — | + |
| X44A | — | — | ++ |

Results indicate that (a) an amino acid position corresponding to amino acid position 22 and 31 of SEQ ID NO:10, SEQ ID NO:17 and SEQ ID NO:21 moderates antigen binding (i.e. positions 22 and 31 moderate binding of a synNAPS ligand to Cry1Ab, mCry3A and eCry3.1Ab); (b) an amino acid position corresponding to amino acid position 44 of SEQ ID NO:10 and SEQ ID NO:17 moderates antigen binding (i.e. position 44 moderates binding of a synNAPS to Cry1Ab and mCry3A); (c) an amino acid position corresponding to amino acid position 29 of SEQ ID NO:10 and SEQ ID NO:21 moderates antigen binding (i.e. position 29 moderates binding of a synNAPS to Cry1Ab and eCry3.1Ab); (d) an amino acid position corresponding to amino acid position 9, 21, 24 or 40 of SEQ ID NO:17 or SEQ ID NO:21 moderates antigen binding (i.e. positions 9, 21, 24 and 40 moderate binding of a synNAPS to mCry3A and eCry3.1Ab).

Example 7. Expression of synNAPS in Plant Cells

This example describes the expression of a synNAPS ligand in plant cells. For this example, an expression cassette was made comprising a cestrum (CMP) promoter (U.S. Pat. No. 7,166,770) operably linked to a synNAPS-13 coding sequence which was operably linked to a NOS terminator. The resulting expression cassette was cloned into a binary vector and transformed into *Agrobacterium* strain EHA101 for delivery to plant cells. Leaves from three plants each of corn, soybean and tobacco were infiltrated with the *Agrobacterium* containing the expression vector). The infiltrated plants were placed in a tray and maintained in the growth chamber at 25° C. with a photoperiod of 16 hours light and 8 hours dark. After 4 days, the tissue was sampled, extracted in PBST and tested in a direct binding assay against Cry1Ab, eCry3.1Ab and mCry3A using an ELISA described above. Extract with synNAPS-13 added at 1 nM was used as a positive control. Absorbance was read at A405. Results indicated that no extract from corn, soybean or tobacco detected Cry1Ab or mCry3A. However, extracts from all three plant species detected eCry3.1Ab, indicating that functional synNAPS-13 can be produced in corn, soybean or tobacco plants.

What is claimed is:

1. A synthetic non-antibody protein scaffold (synNAPS), wherein the synNAPS comprises SEQ ID NO: 21, 83, 92, or 95.

2. The synNAPS of claim 1, wherein the synNAPS comprises SEQ ID NO:21.

3. The synNAPS of claim 1, wherein the synNAPS comprises SEQ ID NO:92.

4. The synNAPS of claim 1, wherein the synNAPS comprises SEQ ID NO:83.

5. The synNAPS of claim 1, wherein the synNAPS comprises SEQ ID NO:95.

* * * * *

UNITED STATES PATENT AND TRADEMARK OFFICE
CERTIFICATE OF CORRECTION

| | |
|---|---|
| PATENT NO. | : 11,714,090 B2 |
| APPLICATION NO. | : 16/771302 |
| DATED | : August 1, 2023 |
| INVENTOR(S) | : Yarnall et al. |

It is certified that error appears in the above-identified patent and that said Letters Patent is hereby corrected as shown below:

On the Title Page

Item (12), should read: Yarnall et al.

Item (72), Inventors: Michele Yarnell, should be corrected to Michele Yarnall

Signed and Sealed this
Twentieth Day of August, 2024

Katherine Kelly Vidal
*Director of the United States Patent and Trademark Office*